(12) United States Patent
Chittoor et al.

(10) Patent No.: US 11,692,182 B2
(45) Date of Patent: Jul. 4, 2023

(54) RNA-GUIDED DNA NUCLEASES AND USES THEREOF

(71) Applicant: Monsanto Technology LLC, St. Louis, MO (US)

(72) Inventors: Jaishree Chittoor, Wildwood, MO (US); Ervin Nagy, Lake Saint Louis, MO (US); Keith H. Turner, Saint Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 470 days.

(21) Appl. No.: 15/766,662

(22) PCT Filed: Oct. 7, 2016

(86) PCT No.: PCT/US2016/056115
§ 371 (c)(1),
(2) Date: Apr. 6, 2018

(87) PCT Pub. No.: WO2017/062855
PCT Pub. Date: Apr. 13, 2017

(65) Prior Publication Data
US 2018/0362943 A1 Dec. 20, 2018

Related U.S. Application Data

(60) Provisional application No. 62/239,678, filed on Oct. 9, 2015.

(51) Int. Cl.
| | |
|---|---|
| C12N 15/82 | (2006.01) |
| C12N 9/22 | (2006.01) |
| C12N 5/04 | (2006.01) |
| C12N 15/10 | (2006.01) |
| C12N 15/90 | (2006.01) |
| C12N 15/63 | (2006.01) |
| C12N 15/11 | (2006.01) |

(52) U.S. Cl.
CPC .............. *C12N 9/22* (2013.01); *C12N 5/04* (2013.01); *C12N 15/102* (2013.01); *C12N 15/11* (2013.01); *C12N 15/111* (2013.01); *C12N 15/63* (2013.01); *C12N 15/8213* (2013.01); *C12N 15/90* (2013.01); *C12N 15/902* (2013.01); *C07K 2319/09* (2013.01); *C07K 2319/60* (2013.01); *C12N 2310/20* (2017.05); *C12N 2510/00* (2013.01); *C12N 2800/80* (2013.01)

(58) Field of Classification Search
CPC ........................................................ C12N 9/22
USPC ......................................................... 435/468
See application file for complete search history.

(56) References Cited

U.S. PATENT DOCUMENTS

| | | | |
|---|---|---|---|
| 4,186,183 | A | 1/1980 | Steck et al. |
| 4,217,344 | A | 8/1980 | Vanlerberghe et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,774,085 | A | 9/1988 | Fidler |
| 4,837,028 | A | 6/1989 | Allen |
| 4,897,355 | A | 1/1990 | Eppstein et al. |
| 4,946,787 | A | 8/1990 | Eppstein et al. |
| 5,049,386 | A | 9/1991 | Eppstein et al. |
| 5,106,739 | A | 4/1992 | Comai et al. |
| 5,322,938 | A | 6/1994 | McPherson et al. |
| 5,352,605 | A | 10/1994 | Fraley et al. |
| 5,359,142 | A | 10/1994 | McPherson et al. |
| 5,378,619 | A | 1/1995 | Rogers |
| 5,530,196 | A | 6/1996 | Fraley et al. |
| 5,580,859 | A | 12/1996 | Felgner et al. |
| 5,589,466 | A | 12/1996 | Felgner et al. |
| 5,593,972 | A | 1/1997 | Weiner et al. |
| 5,641,876 | A | 6/1997 | McElroy et al. |
| 5,837,848 | A | 11/1998 | Ely et al. |
| 5,850,019 | A | 12/1998 | Maiti et al. |
| 6,051,753 | A | 4/2000 | Comai et al. |
| 6,140,078 | A | 10/2000 | Sanders et al. |
| 6,175,060 | B1 | 1/2001 | Lefebvre et al. |
| 6,177,611 | B1 | 1/2001 | Rice |
| 6,232,526 | B1 | 5/2001 | McElroy et al. |
| 6,252,138 | B1 | 6/2001 | Karimi et al. |
| 6,294,714 | B1 | 9/2001 | Matsunaga et al. |
| 6,426,446 | B1 | 7/2002 | McElroy et al. |

(Continued)

FOREIGN PATENT DOCUMENTS

| | | |
|---|---|---|
| CN | 104854241 A | 8/2015 |
| CN | 105916987 A | 8/2016 |

(Continued)

OTHER PUBLICATIONS

GenBank Accession WP_001271093, published online May 29, 2013.*

(Continued)

*Primary Examiner* — Li Zheng
(74) *Attorney, Agent, or Firm* — Morrison & Foerster LLP

(57) ABSTRACT

Provided herein are systems, methods, and compositions for the modification of target DNA sequences. More particularly, systems, methods, and compositions for cleaving a target DNA in eukaryotic cells with a guide RNA capable of hybridizing with a target sequence and an RNA-guided DNA nuclease are provided. Also provided are vectors and vector systems which encode one or more components of a CRISPR complex, as well as methods for the design and use of such vectors. Also provided are methods for identifying and validating novel CRISPR systems.

32 Claims, 10 Drawing Sheets
Specification includes a Sequence Listing.

(56) References Cited

U.S. PATENT DOCUMENTS

| | | | |
|---|---|---|---|
| 6,429,357 B1 | 8/2002 | McElroy et al. | |
| 6,429,362 B1 | 8/2002 | Crane | |
| 6,433,252 B1 | 8/2002 | Kriz et al. | |
| 6,437,217 B1 | 8/2002 | McElroy et al. | |
| 6,635,806 B1 | 10/2003 | Kriz et al. | |
| 7,151,204 B2 | 12/2006 | Houmard et al. | |
| 9,121,022 B2 | 9/2015 | Sammons et al. | |
| 2010/0093617 A1 | 4/2010 | Barrangou | |
| 2014/0068797 A1* | 3/2014 | Doudna | C12N 15/90 800/18 |
| 2014/0315985 A1 | 10/2014 | May et al. | |
| 2015/0059010 A1 | 2/2015 | Cigan et al. | |
| 2017/0321198 A1* | 11/2017 | Severinov | C12N 15/85 |

FOREIGN PATENT DOCUMENTS

| | | |
|---|---|---|
| EP | 3 009 511 A2 | 4/2016 |
| WO | WO 91/16024 A1 | 10/1991 |
| WO | WO 91/17424 A1 | 11/1991 |
| WO | 2010075424 A2 | 7/2010 |
| WO | WO 2011/112570 A1 | 9/2011 |
| WO | WO 2013/176772 A1 | 11/2013 |
| WO | 2015131101 A1 | 9/2015 |
| WO | 2015148863 A2 | 10/2015 |
| WO | WO 2015/153791 A1 | 10/2015 |
| WO | WO 2016/196738 A1 | 12/2016 |
| WO | WO 2016/196782 A1 | 12/2016 |
| WO | WO 2016/205749 A1 | 12/2016 |
| WO | WO 2017/106569 A1 | 6/2017 |
| WO | WO 2017/143071 A1 | 8/2017 |

OTHER PUBLICATIONS

GenBank AHDH01000058.1 (published online Aug. 2012) (Year: 2012).*
GenBank Accession WP_001271093.1 (Year: 2013).*
GenBank Accession WP_016119566.1 (Year: 2013).*
GenBank Accession WP_016106885.1 (Year: 2013).*
GenBank AUBP01000009.1 (available online 2013) (Year: 2013).*
Ahmad et al., "Antibody-mediated Specific Binding and Cytotoxicity of Liposome-entrapped Doxorubicin to Lung Cancer Cells in Vitro," *Cancer Research*, 52:4817-4820 (1992).
Anderson et al., "Human gene therapy," *Science*, 256(5058):808-813 (1992).
Behr, J., "Gene Transfer with Synthetic Cationic Amphiphiles: Prospects for Gene Therapy," *Bioconjugate Chem.*, 5(5):382-389 (1994).
Bevan et al., "Structure and transcription of the nopaline synthase gene region of T-DNA," *Nucleic Acids Research*, 11(2):369-385 (1983).
Bland et al., "CRISPR Recognition Tool (CRT): a tool for automatic detection of clustered regularly interspaced palindromic repeats," *BMC Bioinformatics*, 8:209 (2007).
Callis et al., "Heat Inducible Expression of a Chimeric Maize hsp70CAT Gene in Maize Protoplasts," *Plant Physiol*, 88:965-968 (1988).
Chan et al., "'Deadman' and 'Passcode' microbial kill switches for bacterial containment," *Nature Chemical Biology*, 12:82-86 (2016) doi:10.1038/nchembio.1979.
Chandler et al., "Two Regulatory Genes of the Maize Anthocyanin Pathway are Homologous: Isolation of B Utilizing R Genomic Sequences," *The Plant Cell*, 1(12):1175-1183 (1989).
Chen et al., "A highly sensitive selection method for directed evolution of homing endonucleases," *Nucleic Acids Research*, 33(18):e154 (2005).
Cho et al., "Lipid-Like Nanoparticles for Small Interfering RNA Delivery to Endothelial Cells," *Advanced Functional Materials*, 19:3112-3118 (2009).
Chylinski et al., "The tracrRNA and Cas9 families of type II CRISPR-Cas immunity systems," *RNA Biology*, 10(5):726-737 (2013).
Crystal, R.G., "Transfer of Genes to Humans: Early Lessons and Obstacles to Success," *Science*, 270(5235):404-410 (1995).
Depicker et al., "Nopaline synthase: transcript mapping and DNA sequence," *Journal of Molecular and Applied Genetics*, 1(6):561-573 (1982).
Dey et al., "Toward a "structural BLAST": Using structural relationships to infer function," *Protein Science*, 22:359-366 (2013).
Dumitrache et al., "Trex2 Enables Spontaneous Sister Chromatid Exchanges Without Facilitating DNA Double-Strand Break Repair," *Genetics*, 188(4):787-797 (2011).
Ebert et al, "Identification of an essential upstream element in the nopaline synthase promoter by stable and transient assays," *PNAS USA*, 84:5745-5749 (1987).
El-Andaloussi et al., "Exosome-mediated delivery of siRNA in vitro and in vivo," *Nature Protocols*, 7:2112-2126 (2012).
Finn et al., "Pfam: the protein families database," *Nucleic Acids Research*, 42:D222-D230 (2014).
Gao et al., "Cationic liposome-mediated gene transfer," *Gene Therapy*, 2(10):710-722 (1995).
GenBank Accession V00087.
Geissmann, Q., "OpenCFU, a New Free and Open-Source Software to Count Cell Colonies and Other Circular Objects," *PLoS One*, 8(2):e54072 (2013).
Guo et al., "Directed evolution of an enhanced and highly efficient FokI cleavage domain for zinc finger nucleases," *J. Mol. Biol.*, 400:96-107 (2010).
Hsu et al., "DNS targeting specificity of RNA-guided Cas9 nucleases," *Nature Biotechnology*, 31:827-832 (2013).
Karvelis et al., "Rapid characterization of CRISPR-Cas9 protospacer adjacent motif sequence elements," *Genome Biology*, 16:253 (2015).
Kleinstiver et al., "Engineered CRISPR-Cas9 nucleases with altered PAM specificities," *Nature*, 523:481-485 (2015).
Kremer et al., "Adenovirus and adeno-associated virus mediated gene transfer," *British Medical Bulletin*, 51(1):31-44 (1995).
Kuhlemeier et al., "The Pea rbcS-3 A Promoter Mediates Light Responsiveness but Not Organ Specificity," *The Plant Cell*, 1(4):471-478 (1989).
Lawton et al., "Expression of a soybean β-conclycinin gene under the control of the Cauliflower Mosaic $_{35}$S and $_{19}$S promoters in transformed petunia tissues," *Plant Molecular Biology*, 9(4):315-324 (1987).
Lewis et al., "Efficient delivery of siRNA for inhibition of gene expression in postnatal mice," *Nature Genetics*, 32:107-108 (2002).
Marcotte et al., "Abseisic Acid-Responsive Sequences from the Em Gene of Wheat," *The Plant Cell*, 1:969-976 (1989).
Miller, A.D., "Human gene therapy comes of age," *Nature*, 357:455-460 (1992).
Nabel et al., "Direct gene transfer for immunotherapy and immunization," *TIBTech*, 11:211-215 (1993).
Odell et al., "Identification of DNA sequences required for activity of the cauliflower mosaic virus 35S promoter," *Nature*, 313:810-812 (1985).
Reich et al., "Small interfering RNA (siRNA) targeting VEGF effectively inhibits ocular neovascularization in a mouse model," *Molecular Vision*, 9:210-216 (2003).
Remy et al., "Gene Transfer with a Series of Lipophilic DNA-Binding Molecules," *Bioconjugate Chemistry*, 5(6):647-654 (1994).
Schnäffner et al., "Maize rbcS Promoter Activity Depends on Sequence Elements Not Found in Dicot rbcS Promoters," *The Plant Cell*, 3:997-1012 (1991).
Schroeder et al., "Lipid-based nanotherapeutics for siRNA delivery," *J Intern Med*, 267(1):9-21 (2010).
Shen et al., "Gene silencing by adenovirus-delivered siRNA," *FEBS Letters*, 539:111-114 (2003).
Shmakov et al., "Discovery and Functional Characterization of Diverse Class 2 CRISPR-Cas Systems," *Molecular Cell*, 60:385-397 (2015).
Siebertz et al., "cis-Analysis of the Wound-Inducible Promoter wun1 in Transgenic Tobacco Plants and Histochemical Localization of Its Expression," *The Plant Cell*, 1:961-968 (1989).
Simeoni et al., "Insight into the mechanism of the peptide-based gene delivery system MPG: implications for delivery of siRNA into mammalian cells," *Nucleic Acids Research*, 31(11):2717-2724 (2003).

(56) References Cited

OTHER PUBLICATIONS

Sørensen et al., "Gene silencing by systemic delivery of synthetic siRNAs in adult mice," *J Mol Biol*, 327(4):761-766 (2003).
Takebe et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat," *Mol Cell Biol*, 8(1):466-472, 1988.
Thompson et al., "CLUSTAL W: improving the sensitivity of progressive multiple sequence alignment through sequence weighting, position-specific gap penalties and weight matrix choice," *Nucleic Acids Research*, 22(22):4673-4680 (1994).
Van Brunt, J., "Molecular Farming: Transgenic Ammals as Bioreactors," *Nature Biotechnology*, 6:1149-1154 (1988).
Vigne et al., "Third-generation adenovectors for gene therapy," *Restorative Neurology and Neuroscience*, 8:35-36 (1995).
Wang et al., "Restriction-ligation-free (RLF) cloning: a high-throughput cloning method by in vivo homologous recombination of PCR products," *Genetics and Molecular Research*, 14(4):12306-12315 (2015).
Xia et al., "siRNA-mediated gene silencing in vitro and in vivo," *Nature Biotechnology*, 20:1006-1010 (2002).
Yang et al., "Maize sucrose synthase-1 promoter directs phloem cell-specific expression of *Gus* gene in transgenic tobacco plants," *PNAS*, 87(11):4144-4148 (1990).
Yu et al., "Progress towards gene therapy for HIV infection," *Gene Therapy*, 1:13-26 (1994).
Zetsche et al., "Cpf1 is a single RNA-guided endonuclease of a class 2 CRISPR-Cas system," *Cell*, 163(3):759-771 (2015).
Zhu et al., "Efficiency and inheritance of targeted mutagenesis in maize using CRISPR-Cas9," *J Genetics and Genomics*, 43:25-36 (2016).
International Search Report dated Feb. 23, 2017 in International Application No. PCT/US2016/054968.
Anonymous: "Hit details UniParc-UPI0002719910," Uniprot, pp. 1-3 (2012) <https://www.uniprot.org/uniparc/UPI0002719910>.
Communication Pursuant to Article 94(3) EPC dated Aug. 26, 2020, in European Patent Application No. 16854482.3.
Extended European Search Report dated Jul. 17, 2019, in European Patent Application No. 16854482.3.
Partial European Search Report dated Mar. 26, 2019, in European Patent Application No. 16854482.3.
Tian et al., "A novel thermal Cas12b from a hot spring bacterium with high target mismatch tolerance and robust DNA cleavage efficiency," *International Journal of Biological Macromolecules*, 147:376-384 (2020).
International Search Report and Written Opinion, dated Mar. 13, 2017, for PCT Application No. PCT/US2016/056115, filed Oct. 7, 2016, 17 pages.

* cited by examiner

Blue-white selection in *E.coli*

Vector construct with region of interest (ROI)

Vector construct with target and LacZ reporter

Co-transform into *E. coli* blue-white colony selection

Sequence analysis of white ROI colonies

In vitro cutting assay

Vector construct with region of interest (ROI) and transform into *E. coli*

Purify the novel endonuclease from *E. coli*

*In* vitro digestion of DNA fragment containing the target sequence

DNA fragment length analysis by gel electrophoresis

DNA sequence analysis

In planta cutting assay

Clone genes of interest (RGEN protein, guideRNA) into plant expression vectors

Transform plant expression vectors, ds oligo, and (optionally) plasmid DNA containing target sequence into plant cell Analysis for RNA guided DSB induced in plant cell chromosome or co-transformed plasmid by PCR and/or sequencing

RNA-GUIDED DNA NUCLEASES AND USES THEREOF

CROSS-REFERENCE TO RELATED APPLICATIONS AND INCORPORATION OF SEQUENCE LISTING

This application claims priority to U.S. Provisional Patent Application No. 62/239,678 entitled NOVEL RNA-GUIDED DNA NUCLEASES AND USES THEREOF filed Oct. 9, 2015, which is incorporated in its entirety. The sequence listings contained in the files "P34351US00_SEQ.txt", which is 515,465 bytes in size (measured in operating system MS Windows) and created on Oct. 9, 2015 and filed with U.S. Provisional Patent Application No. 62/239,678 on Oct. 9, 2015, is incorporated by reference in their entirety herein. A computer readable form of a sequence listing is filed with this application by electronic submission and is incorporated into this application by reference in its entirety. The sequence listing is contained in the file named P34351WO00.txt, which is 3,098,529 bytes in size (measured in operating system MS Windows) and created on Oct. 7, 2016.

BACKGROUND

CRISPRs (Clustered Regularly Interspaced Short Palindromic Repeats) are loci found in the genomes of bacteria and archaea that contain multiple short direct repeats. CRISPR RNAs (crRNAs) associate with CRISPR-associated (Cas) effector proteins to form CRISPR-Cas systems that recognize foreign nucleic acids. CRISPRs systems are part of the adaptive immune system of bacteria and archaea, protecting them against invading nucleic acids, such as viruses, by cleaving the foreign DNA in a sequence-dependent manner. Immunity is acquired by integrating of short fragments of the invading DNA, known as spacers, between two adjacent repeats at the proximal end of a CRISPR locus. The CRISPR arrays are transcribed during subsequent encounters with invasive nucleic acids and are processed into small interfering CRISPR RNAs (crRNAs) of approximately 40 nt in length, which associate with the trans-activating CRISPR RNA (tracrRNA) to guide the CRISPR associated nuclease to the invasive nucleic acid. The CRISPR/Cas9 effector complex cleaves homologous double-stranded DNA sequences known as protospacers in the invading DNA. A prerequisite for cleavage is the presence of a conserved protospacer-adjacent motif (PAM) downstream of the target DNA, which, for Cas9, usually has the sequence 5'-NGG-3' but less frequently NAG. Specificity is provided by a "seed sequence" in the crRNA which is located approximately 12 bases upstream of the PAM, which must be capable of hybridizing with the target sequence. Cpf1, a type V Cas effector protein, acts in a similar manner to Cas9, but Cpf1 does not require a tracrRNA.

CRISPR-Cas systems are dived into two classes: Class 1 CRISPR systems, subdivided into types I, III, and IV, and Class 1 systems utilize multiple Cas proteins with a crRNA to form a complex; and Class 2 CRISPR systems, subdivided into types II and V, utilize a single Cas protein with a crRNA to form a complex capable of sequence specific genome modification.

BRIEF DESCRIPTION

Several embodiments relate to a recombinant nucleic acid comprising a heterologous promoter operably linked to a polynucleotide encoding a CRISPR enzyme, wherein the CRISPR enzyme comprises an amino acid sequence selected from the group consisting of SEQ ID NOs: 1-36, 73 and 75-87 or a fragment thereof. Several embodiments relate to a recombinant nucleic acid comprising a heterologous promoter operably linked to a polynucleotide encoding a CRISPR enzyme, wherein the CRISPR enzyme has a sequence homology or identity of at least 80%, at least 85%, at least 90%, at least 95%, at least 96%, at least 97%, at least 98%, or at least 99% with a CRISPR enzyme comprising an amino acid sequence selected from SEQ ID NOs: 1-36, 73 and 75-87. In some embodiments, a vector comprising a recombinant nucleic acid comprising a heterologous promoter operably linked to a polynucleotide encoding CRISPR enzyme with an amino acid sequence selected from the group consisting of SEQ ID NOs: 1-36, 73 and 75-87 are provided. In some embodiments, a vector comprising a recombinant nucleic acid comprising a heterologous promoter operably linked to a polynucleotide encoding CRISPR enzyme, wherein the CRISPR enzyme has a sequence homology or identity of at least 80%, at least 85%, at least 90%, at least 95%, at least 96%, at least 97%, at least 98%, or at least 99% with a CRISPR enzyme comprising an amino acid sequence selected from SEQ ID NOs: 1-36, 73 and 75-87 are provided.

Several embodiments relate to a cell comprising a recombinant nucleic acid comprising a heterologous promoter operably linked to a polynucleotide encoding a CRISPR enzyme, wherein the CRISPR enzyme comprises an amino acid sequence selected from the group consisting of SEQ ID NOs: 1-36, 73 and 75-87 or a fragment thereof. Several embodiments relate to a cell comprising a recombinant nucleic acid comprising a heterologous promoter operably linked to a polynucleotide encoding a CRISPR enzyme, wherein the CRISPR enzyme has a sequence homology or identity of at least 80%, at least 85%, at least 90%, at least 95%, at least 96%, at least 97%, at least 98%, or at least 99% with a CRISPR enzyme comprising an amino acid sequence selected from SEQ ID NOs: 1-36, 73 and 75-87. In some embodiments, the recombinant nucleic acid is expressed transiently in the cell. In some embodiments, the recombinant nucleic acid is integrated into a genome of the cell. In some embodiments, the recombinant nucleic acid is integrated into a B chromosome of the cell. In some embodiments, the cell is a prokaryotic cell. In some embodiments, the cell is a eukaryotic cell. In some embodiments, the eukaryotic cell is a plant cell. In some embodiments, the eukaryotic cell is a algal cell. In some embodiments, the eukaryotic cell is a mammalian cell.

In one aspect, the present disclosure provides a system for sequence-specific modification of a target nucleic acid sequence comprising (a) a guide RNA or a DNA molecule encoding a guide RNA, where the guide RNA is specific for a target nucleic acid sequence, and (b) a polynucleotide encoding an CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87.

In one aspect, the present disclosure provides a method for sequence-specific modification of a target nucleic acid sequence in a cell comprising providing to the cell a nucleic acid-targeting system comprising (a) a guide RNA or a DNA molecule encoding a guide RNA, wherein the guide RNA is specific for a target nucleic acid sequence, and (b) a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87 or a polynucleotide encoding the CRISPR enzyme.

In one aspect, the present disclosure provides a method for sequence-specific modification of a target nucleic acid sequence in a cell comprising providing to a cell (a) a guide RNA specific for a target nucleic acid sequence in a cell, and (b) an a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87 or polynucleotide encoding the CRISPR enzyme, wherein the target nucleic acid sequence is modified.

In an aspect, the present disclosure provides a eukaryotic cell containing a target nucleic acid sequence that has been modified with sequence specificity by a method for sequence-specific modification of a target nucleic acid sequence in a cell comprising providing to a cell (a) a guide RNA specific for a target nucleic acid sequence in a cell, and (b) an a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87 or polynucleotide encoding the CRISPR enzyme, where the target nucleic acid sequence is modified.

In an aspect, the present disclosure provides a method of selectively modulating transcription of at least one target DNA in a eukaryotic cell comprising contacting the eukaryotic cell with: (a) a guide RNA or a DNA encoding a guide RNA where the guide RNA further comprises: (i) a first segment comprising a nucleotide sequence that is complementary to the target DNA; and (ii) a second segment that interacts with an RNA-guided DNA nuclease; and (b) an polynucleotide encoding a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87, where components (a) and (b) are located on same or different vectors, where the guide RNA and the RNA-guided DNA nuclease form a complex in the eukaryotic cell, and where the complex selectively modulates transcription of the target DNA.

Several embodiments relate to a method of identifying a CRISPR enzyme from a bacterial genome. In some embodiments, a polynucleotide encoding a CRISPR enzyme is identified based on its association within the bacterial genome with a type II CRISPR repeat. In certain aspects, the polynucleotide encoding the CRISPR enzyme is further identified by association within the bacterial genome with a Cast, a Cas2, or a Cast and a Cas2 but not Cas5 or Cas3. In some embodiments, the polynucleotide encoding the CRISPR enzyme is located in the same operon as the CRISPR locus. In other embodiments, the polynucleotide encoding the CRISPR enzyme is located within 2 kilobases of the CRISPR loci. In some embodiments, a polynucleotide encoding the CRISPR enzyme is identified by the presence of one or more pfam domains identified in Table 1. In some embodiments, a polynucleotide encoding a CRISPR enzyme provided herein can be identified by the presence of one or more, two or more, three or more, four or more, five or more, six or more, seven or more, eight or more, nine or more, or ten or more Pfam domains identified in Table 1. For more information regarding Pfam domains, see pfam.xfam.org; and Finn et al., Nucleic Acids Research (2014) 42: D222-230. In some embodiments, the bacterial genome is selected from the group consisting of: *Lysinibacillus* sp., *Brevibacillus* sp., *Sphingobium* sp., *Undibacterium* sp., *Bacillus* sp., *Chryseobacterium* sp., *Sphingomonas* sp., and *Labrys* sp. In some embodiments, the bacterial genome is selected from the group consisting of: *Brevibacillus laterosporus*; *Bacillus thuringiensis*; *Enterococcus faecalis*; *Brevibacillus brevis*; *Undibacterium pigrum*; *Novosphingobium rosa*; *Labrys methylaminiphilus*; *Brevibacillus parabrevis*.

Several embodiments relate to a method of enhancing recombination at selected genomic loci, comprising providing to a plant cell at least one nucleic acid-targeting system that introduces genome modification in a first genomic locus, thereby inducing recombination between the first genomic locus and a second genomic locus, wherein the at least one nucleic acid-targeting system does not introduce a genome modification at the second genomic locus, and selecting at least one plant cell comprising a recombination event between the first genomic locus and the second genomic locus. Several embodiments relate to a method of enhancing recombination at selected genomic loci, comprising providing to a plant cell at least one nucleic acid-targeting system that introduces genome modification at a first genomic locus and a second genomic locus, thereby inducing recombination between the first genomic locus and the second genomic locus, and selecting at least one plant cell comprising a recombination event between the first genomic locus and the second genomic locus. Several embodiments relate to a method of enhancing recombination at selected genomic loci, comprising providing to a cell a first nucleic acid-targeting system that introduces a genome modification at a first genomic locus and a second nucleic acid-targeting system that introduces a genome modification at a second genomic locus, thereby inducing recombination between the first genomic locus and the second genomic locus, and selecting at least one progeny comprising a recombination event between the first genomic locus and the second genomic locus. In some embodiments the first and second genomic loci are in cis. In some embodiments, the first and second genomic loci are in trans. In some embodiments, the first and second genomic loci are homologs. In some embodiments, the first and second genomic loci are paralogs. In some embodiments, the first and second genomic loci are homeologs. In some embodiments, the first and second genomic loci are identical. In some embodiments, the first genomic locus and the second genomic locus are on homologous chromosomes. In some embodiments, the first genomic locus and the second genomic locus are on non-homologous chromosomes. In some embodiments, the first genomic locus and the second genomic locus are on homologous chromosomes. In some embodiments, the first and second genomic loci share at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity. In some embodiments, the first genomic locus and the second genomic locus are located on homologous chromosomes. In some embodiments, the first genomic locus and the second genomic locus are located on non-homologous chromosomes. In some embodiments, the genome modification is a double strand break (DSB). In some embodiments, the genome modification is a single strand break. In some embodiments, the genome modification occurs at the beginning of meiosis. In some embodiments, the recombination is asymmetric. In some embodiments, the recombination is symmetric. In some embodiments, the first target sequence and/or the second target sequence is genic. In some embodiments, the first target sequence and/or the second target sequence is within an intergenic region. In some embodiments, the first target sequence is in a genomic locus that is homologous to at least about 100 bp, at least about 150 bp, at least about 200 bp, at least about 250 bp, at least about 300 bp, at least about 350 bp, at least about 400 bp, at least about 450 bp, at least about 500 bp, at least about 600 bp, at least about 700 bp, at least about 800 bp, at least about 900 bp, or at least about 1000 bp of a genomic locus containing the second target sequence. In some embodiments, the first target sequence is in a genomic locus that is homologous to at least about 100 bp, at least about 150 bp, at least about 200 bp, at least about 250 bp, at least about 300 bp, at least about 350 bp, at least about 400 bp, at least about 450 bp, at least about 500 bp, at least about 600 bp, at least about 700 bp, at least about 800 bp, at least about 900 bp, or at least about 1000 bp of a genomic locus containing the second target sequence, wherein the genomic locus containing the first target sequence and the genomic locus containing the second target sequence are in corresponding positions in the genome. In some embodiments, the first target sequence is in a genomic locus that is homologous to at least about 100 bp, at least about 150 bp, at least about 200 bp, at least about 250 bp, at least about 300 bp, at least about 350 bp, at least about 400 bp, at least about 450 bp, at least about 500 bp, at least about 600 bp, at least about 700 bp, at least about 800 bp, at least about 900 bp, or at least about 1000 bp of a genomic locus containing the second target sequence, wherein the genomic locus containing the first target sequence and the genomic locus containing the second target sequence are not in corresponding positions in the genome. In some embodiments, the first target sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the second target sequence. In some embodiments, one or more of the first genomic locus and the second genomic locus comprise one or more genomic regions selected independently from the group consisting of a gene, an array of tandemly duplicated genes, an enhancer, a suppressor, a promoter, a termination sequence, a splice acceptor sequence, a splice donor sequence, an intron, an exon, an siRNA, and a quantitative trait locus (QTL). In some embodiments, progeny of the one plant cell comprising the recombination event between the first genomic locus and the second genomic locus exhibit resistance to one or more diseases selected from Anthracnose Stalk Rot (*Colletotrichum graminicola*), Fusarium Ear Rot (*Fusarium verticillioides*), Fusarium Stalk Rot (*Fusarium* spp.), Gibberella Ear Rot (*Gibberella moniliformis*), Gibberella Stalk Rot (*Gibberella zeae*), Goss's Wilt and Leaf Blight (*Clavibacter michiganensis*), Gray Leaf Spot (*Cercospora zeae-maydis, C. zeina*), Northern Corn Leaf Blight (*Exserohilum turcicum*), Sudden death syndrome (*Fusarium solani* f. sp. *glycines*), Asian soybean rust (*Phakopsora pachyrhizi*), Phytophthora root and stem rot (*Phytophthora sojae*), Root-knot Nematode (*Meloidogyne* spp.), Soybean Cyst Nematode (*Heterodera glycines*), Reniform nematode (*Rotylenchulus reniformis*), Root-knot nematode (*Meloidogyne incognita*), Fusarium wilt (*Fusarium oxysporurn* f. sp. *vasinfectum*), Verticillium wilt (*Verticillium dahlia*), Fusarium head blight (*Fusarium graminearum*), Fusarium seedling blight (*Fusarium* spp., *Septoria nodorum*), Fusarium Leaf Blotch (*Monographella nivalis*), and Stem Rust (*Puccinia graminis*). In some embodiments, the plant is a maize plant. In some embodiments, the plant is a soybean plant. In some embodiments, the plant is a cotton plant. In some embodiments, the plant is a wheat plant. In some embodiments, the plant is a sorghum plant. In some embodiments, the plant is a canola plant. In some embodiments, the nucleic acid-targeting system comprising (a) comprises a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87 one or more and (b) a guide RNA capable of hybridizing with a target sequence. In some embodiments, the nucleic acid-targeting system further comprises a tracrRNA. In some embodiments, the nucleic acid-targeting system further comprises a divalent cation. In some embodiments, the nucleic acid-targeting system further comprises $Mg^{2+}$. In some embodiments, the nuclease activity of the CRISPR enzyme is inactivated. In some embodiments, the nucleic acid-targeting system further comprises a CRISPR enzyme with a heterologous functional domain. Several embodiments relate to a plant, plant cell or a seed of a plant produced by according to the aforementioned methods.

Several embodiments relate to a method of introgressing a genomic locus of interest into a selected germplasm, comprising generating a plant cell comprising a first parental genome comprising the genomic locus of interest and a second parental genome comprising the selected germplasm, providing to the plant cell a first nucleic acid-targeting system that introduces genome modification in the first parental genome at a target sequence adjacent to the genomic locus of interest, thereby inducing recombination between the first parental genome and the second parental genome, and selecting at least one progeny comprising at least one recombinant chromosome comprising the selected germplasm and the genomic locus of interest. Several embodiments relate to a method of introgressing a genomic locus of interest into a selected germplasm, comprising generating a plant cell comprising a first parental genome comprising the genomic locus of interest and a second parental genome comprising the selected germplasm, providing to the plant cell a first nucleic acid-targeting system that introduces genome modification in the first parental genome at a target sequence adjacent to the genomic locus of interest and a genome modification at a target site in the second parental genome, thereby inducing recombination between the first parental genome and the second parental genome, and selecting at least one progeny comprising at least one recombinant chromosome comprising the selected germplasm and the genomic locus of interest. Several embodiments relate to a method of introgressing a genomic locus of interest into a selected germplasm, comprising generating a plant cell comprising a first parental genome comprising the genomic locus of interest and a second parental genome comprising the selected germplasm, providing to the plant cell a first nucleic acid-targeting system that introduces genome modification in the first parental genome at a target sequence adjacent to the genomic locus of interest and a second nucleic acid-targeting system that introduces a genome modification in the first parental genome at a second target sequence adjacent to the genomic locus, wherein the second target sequence is on opposite side of the genome genomic locus of interest from the target sequence of the first nucleic acid-targeting system, thereby inducing recombination between the first parental genome and the second parental genome, and selecting at least one plant cell comprising at least one recombinant chromosome comprising the selected germplasm and the genomic locus of interest. Several embodiments relate to a method of introgressing a genomic locus of interest into a selected germplasm, comprising generating a plant cell comprising a first parental genome comprising the genomic locus of interest and a second parental genome comprising the selected germplasm, providing to the plant cell a first nucleic acid-targeting system that introduces genome modification in the first parental genome at a target sequence adjacent to the genomic locus of interest and a genome modification at a target site in the second parental genome and further introducing into the plant cell a second nucleic acid-targeting system that introduces a genome modification in the first parental genome at a second target sequence adjacent to the genomic locus, wherein the second target sequence is on opposite side of the genome genomic locus of interest from the target sequence of the first nucleic acid-targeting system, thereby inducing recombination between the first parental genome and the second parental genome, and selecting at least one plant cell comprising at least one recombinant chromosome comprising the selected germplasm and the genomic locus of interest. In some embodiments, the second nucleic acid-targeting system introduces a genome modification at a target sequence in the second parental genome. In some embodiments, the recombination is asymmetric. In some embodiments, the recombination is symmetric. In some embodiments, the genomic locus of interest comprises one or more genomic regions selected independently from the group consisting of a gene, an array of tandemly duplicated genes, a multigene family, an enhancer, a suppressor, a promoter, a termination sequence, a splice acceptor sequence, a splice donor sequence, an intron, an exon, an siRNA, a sequence encoding a non-coding RNA, a microRNA, a transgene, and a quantitative trait locus (QTL). In some embodiments, the genome modification is a double strand break (DSB). In some embodiments, the genome modification is a single strand break. In some embodiments, the genome modification is a recombinase-mediated DNA exchange reaction. In some embodiments, the genome modification is a transposase-mediated DNA exchange reaction. In some embodiments, the genome modification occurs at the beginning of meiosis. In some embodiments, the target sequence is genic. In some embodiments, the target sequence is within an intergenic region. In some embodiments, the target sequence is in a genomic locus of the first parental genome that is homologous to at least about 100 bp, at least about 150 bp, at least about 200 bp, at least about 250 bp, at least about 300 bp, at least about 350 bp, at least about 400 bp, at least about 450 bp, at least about 500 bp, at least about 600 bp, at least about 700 bp, at least about 800 bp, at least about 900 bp, or at least about 1000 bp of a genomic locus of the second parental genome. In some embodiments, the target sequence is in a genomic locus of the first parental genome that is homologous to at least about 100 bp, at least about 150 bp, at least about 200 bp, at least about 250 bp, at least about 300 bp, at least about 350 bp, at least about 400 bp, at least about 450 bp, at least about 500 bp, at least about 600 bp, at least about 700 bp, at least about 800 bp, at least about 900 bp, or at least about 1000 bp of a genomic locus of the second parental genome, wherein the genomic locus of the first parental genome and the genomic locus of the second parental genome are located in corresponding positions. In some embodiments, the target sequence is in a genomic locus of the first parental genome that is homologous to at least about 100 bp, at least about 150 bp, at least about 200 bp, at least about 250 bp, at least about 300 bp, at least about 350 bp, at least about 400 bp, at least about 450 bp, at least about 500 bp, at least about 600 bp, at least about 700 bp, at least about 800 bp, at least about 900 bp, or at least about 1000 bp of a genomic locus of the second parental genome, wherein the genomic locus of the first parental genome and the genomic locus of the second parental genome are not located in corresponding positions, leading to asymmetric recombination. In some embodiments, the first parental genome and the second parental genome are not sexually compatible. In some embodiments, the first parental genome and the second parental genome are different species. In some embodiments, the first parental genome is *Triticum aestivum* (wheat) and the second parental genome is selected from *Aegilops ovate, Ae. biuncialis, Ae. triuncialis, Ae. quarrosa, Secale cereal, Triticum dicoccoides, Triticum dicoccum* and *Triticum durum*. In some embodiments, the first parental genome is selected from *Aegilops ovate, Ae. biuncialis, Ae. triuncialis, Ae. quarrosa, Secale cereal, Triticum dicoccoides, Triticum dicoccum* and *Triticum durum* and the second parental genome is *Triticum aestivum* (wheat). In some embodiments, the first parental genome is *Gossypium hirsutum* (cotton) and the second parental genome is selected from *G. sturtii, G. davidsonii, G. arboretum* and *G. raimondii*. In some embodiments, the first parental genome is selected from *G. sturtii, G. davidsonii, G. arboretum* and *G. raimondii* and the second parental genome is *Gossypium hirsutum* (cotton). In some embodiments, the first parental genome and/or the second parental genome are haploid. In some embodiments, the first parental genome and/or the second parental genome are diploid. In some embodiments, the genomic locus of interest is Rp1 disease resistance locus. In some embodiments, the genomic locus of interest is Rpp1 disease resistance locus. In some embodiments, the genomic locus of interest is Rps1 disease resistance locus. In some embodiments, the genomic locus of interest is Rhg1 disease resistance locus. In some embodiments, the genomic locus of interest is Rgh4 disease resistance locus. In some embodiments, the plant is a maize plant. In some embodiments, the plant is a soybean plant. In some embodiments, the plant is a cotton plant. In some embodiments, the plant is a wheat plant. In some embodiments, the plant is a sorghum plant. In some embodiments, the plant is a canola plant. In some embodiments, the nucleic acid-targeting system comprising (a) comprises a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87 one or more and (b) a guide RNA capable of hybridizing with a target sequence. In some embodiments, the nucleic acid-targeting system further comprises a tracrRNA. In some embodiments, the nucleic acid-targeting system further comprises a divalent cation. In some embodiments, the nucleic acid-targeting system further comprises $Mg2+$. In some embodiments, the nuclease activity of the CRISPR enzyme is inactivated. In some embodiments, the nucleic acid-targeting system further comprises a CRISPR enzyme with a heterologous functional domain Several embodiments relate to a plant, plant cell or a seed of a plant produced by according to the aforementioned methods.

Several embodiments relate to a method of removing linkage drag, comprising generating a plant cell comprising a first parental genome and a second parental genome, wherein the first parental genome comprises a genomic locus of interest linked in cis to an undesirable genomic locus, providing to the cell a first nucleic acid-targeting system that introduces a genome modification between the genomic locus of interest and the undesirable genomic locus, thereby inducing recombination between the first parental genome and the second parental genome and unlinking the genomic locus of interest and the undesirable locus, and selecting at least one progeny comprising the genomic locus of interest. Several embodiments relate to a method of removing linkage drag, comprising generating a plant cell comprising a first parental genome and a second parental genome, wherein the first parental genome comprises a genomic locus of interest linked in cis to an undesirable genomic locus, providing to the cell a first nucleic acid-targeting system that introduces a first genome modification between the genomic locus of interest and the undesirable genomic locus and a second genome modification on opposite side of the undesirable genomic locus from the first genome modification, thereby inducing recombination between the first parental genome and the second parental genome and removing the undesirable locus while maintaining the germplasm of the first parental genome distal to the second genome modification, and selecting at least one progeny comprising the genomic locus of interest. In some embodiments, the second nucleic acid-targeting system introduces a genome modification at a target sequence in the second parental genome. In some embodiments, the recombination is asymmetric. In some embodiments, the recombination is symmetric. In some embodiments, the genomic locus of interest comprises one or more genomic regions selected independently from the group consisting of a gene, an array of tandemly duplicated genes, a multigene family, an enhancer, a suppressor, a promoter, a termination sequence, a splice acceptor sequence, a splice donor sequence, an intron, an exon, an siRNA, a sequence encoding a non-coding RNA, a microRNA, a transgene, and a quantitative trait locus (QTL). In some embodiments, the genome modification is a double strand break (DSB). In some embodiments, the genome modification is a single strand break. In some embodiments, the genome modification is a recombinase-mediated DNA exchange reaction. In some embodiments, the genome modification is a transposase-mediated DNA exchange reaction. In some embodiments, the genome modification occurs at the beginning of meiosis. In some embodiments, the first parental genome and the second parental genome are not sexually compatible. In some embodiments, the first parental genome and the second parental genome are different species. In some embodiments, the first parental genome is *Triticum aestivum* (wheat) and the second parental genome is selected from *Aegilops ovate, Ae. biuncialis, Ae. triuncialis, Ae. quarrosa, Secale cereal, Triticum dicoccoides, Triticum dicoccum* and *Triticum durum*. In some embodiments, the first parental genome is selected from *Aegilops ovate, Ae. biuncialis, Ae. triuncialis, Ae. quarrosa, Secale cereal, Triticum dicoccoides, Triticum dicoccum* and *Triticum durum* and the second parental genome is *Triticum aestivum* (wheat). In some embodiments, the first parental genome is *Gossypium hirsutum* (cotton) and the second parental genome is selected from *G. sturtii, G. davidsonii, G. arboretum* and *G. raimondii*. In some embodiments, the first parental genome is selected from *G. sturtii, G. davidsonii, G. arboretum* and *G. raimondii* and the second parental genome is *Gossypium hirsutum* (cotton). In some embodiments, the first parental genome and/or the second parental genome are haploid. In some embodiments, the first parental genome and/or the second parental genome are diploid. In some embodiments, the genomic locus of interest is Rp1 disease resistance locus. In some embodiments, the genomic locus of interest is Rpp1 disease resistance locus. In some embodiments, the genomic locus of interest is Rps1 disease resistance locus. In some embodiments, the genomic locus of interest is Rhg1 disease resistance locus. In some embodiments, the genomic locus of interest is Rhg4 disease resistance locus. In some embodiments, the plant is a maize plant. In some embodiments, the plant is a soybean plant. In some embodiments, the plant is a cotton plant. In some embodiments, the plant is a wheat plant. In some embodiments, the plant is a sorghum plant. In some embodiments, the plant is a canola plant. In some embodiments, the nucleic acid-targeting system comprising (a) comprises a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87 one or more and (b) a guide RNA capable of hybridizing with a target sequence. In some embodiments, the nucleic acid-targeting system further comprises a tracrRNA. In some embodiments, the nucleic acid-targeting system further comprises a divalent cation. In some embodiments, the nucleic acid-targeting system further comprises Mg2+. In some embodiments, the nuclease activity of the CRISPR enzyme is inactivated. In some embodiments, the nucleic acid-targeting system further comprises a CRISPR enzyme with a heterologous functional domain Several embodiments relate to a plant, plant cell or a seed of a plant produced by according to the aforementioned methods.

Several embodiments relate to a method of coupling genomic loci in repulsion, comprising generating a plant cell comprising a first parental genome comprising a first genomic locus and a second parental genome comprising a second genomic locus, wherein the first genomic locus and the second genetic locus are in repulsion, providing to the cell a first nucleic acid-targeting system that introduces a genome modification adjacent to the first genomic locus, thereby inducing recombination between the first parental genome and the second parental genome, and selecting at least one plant cell comprising the first genomic locus and the second genomic locus on the same chromosome. In some embodiments, the first genomic locus and the second genomic locus are located on homologous chromosomes. In some embodiments, the first parental genome and the second parental genome are not sexually compatible. In some embodiments, the first parental genome and the second parental genome are different species. In some embodiments, the first genomic locus of interest and/or the second genomic locus of interest comprises one or more genomic regions selected independently from the group consisting of a gene, an array of tandemly duplicated genes, an enhancer, a suppressor, a promoter, a termination sequence, a splice acceptor sequence, a splice donor sequence, an intron, an exon, an siRNA, and a quantitative trait locus (QTL). In some embodiments, the first parental genome and/or the second parental genome are haploid. In some embodiments, the first parental genome and/or the second parental genome are diploid. In some embodiments, the first parental genome is *Triticum aestivum* (wheat) and the second parental genome is selected from *Aegilops ovate, Ae. biuncialis, Ae. triuncialis, Ae. quarrosa, Secale cereal, Triticum dicoccoides, *Triticum dicoccum* and *Triticum durum*. In some embodiments, the first parental genome is selected from *Aegilops ovate, Ae. biuncialis, Ae. triuncialis, Ae. quarrosa, Secale cereal, Triticum dicoccoides, Triticum dicoccum* and *Triticum durum* and the second parental genome is *Triticum aestivum* (wheat). In some embodiments, the first parental genome is *Gossypium hirsutum* (cotton) and the second parental genome is selected from *G. sturtii, G. davidsonii, G. arboretum* and *G. raimondii*. In some embodiments, the first parental genome is selected from *G. sturtii, G. davidsonii, G. arboretum* and *G. raimondii* and the second parental genome is *Gossypium hirsutum* (cotton). In some embodiments, the genomic locus of interest is Rp1 disease resistance locus. In some embodiments, the first genomic locus of interest and/or the second genomic locus of interest is Rpp1 disease resistance locus. In some embodiments, the first genomic locus of interest and/or the second genomic locus of interest is Rps1 disease resistance locus. In some embodiments, the first genomic locus of interest and/or the second genomic locus of interest Rhg1 disease resistance locus. In some embodiments, the first genomic locus of interest and/or the second genomic locus of interest Rhg4 disease resistance locus. In some embodiments, the first genomic locus of interest is Rhg1 and the second genomic locus of interest Rhg4. In some embodiments, the plant is a maize plant. In some embodiments, the plant is a soybean plant. In some embodiments, the plant is a cotton plant. In some embodiments, the plant is a wheat plant. In some embodiments, the plant is a sorghum plant. In some embodiments, the plant is a canola plant. In some embodiments, the nucleic acid-targeting system comprising (a) comprises a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87 one or more and (b) a guide RNA capable of hybridizing with a target sequence. In some embodiments, the nucleic acid-targeting system further comprises a tracrRNA. In some embodiments, the nucleic acid-targeting system further comprises a divalent cation. In some embodiments, the nucleic acid-targeting system further comprises Mg2+. In some embodiments, the nuclease activity of the CRISPR enzyme is inactivated. In some embodiments, the nucleic acid-targeting system further comprises a CRISPR enzyme with a heterologous functional domain Several embodiments relate to a plant, plant cell or a seed of a plant produced by according to the aforementioned methods.

Several embodiments relate to a method of generating a new array of tandemly duplicated genes, comprising contacting a cell with a nucleic acid-targeting system that cleaves at least one target sequence in a first array of tandemly duplicated genes thereby inducing asymmetric recombination with a homologous sequence of a second array of tandemly duplicated genes and selecting at least one progeny comprising a new array of tandemly duplicated genes. In some embodiments, the first and second arrays of tandemly duplicated genes are identical. In other embodiments, the first and second arrays of tandemly duplicated genes are different. In some embodiments, the asymmetric recombination generates two new arrays of tandemly duplicated genes, depending on the recombination site. In some embodiments, the asymmetric recombination results in a deletion in at least one of the tandemly duplicated genes. In some embodiments, the cell is a plant cell. In a further embodiment, the plant cell is obtained from a plant selected from an inbred plant or a hybrid plant. In other embodiments, the cell is a mammalian cell.

DETAILED DESCRIPTION

Figure 1:
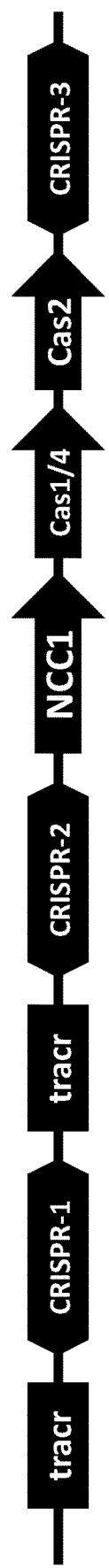
FIG. 1. is an illustration of the genomic region comprising the NCC1 operon with the relative order and orientation of two predicted tracrRNAs ('tracr'), and three separate CRISPR loci (CRISPR-1, CRISPR-2, and CRISPR-3). The NCC1 operon comprises the NCC1 gene (SEQ ID NO: 73), one gene encoding a Cas1 Cas4 fusion, and one gene encoding Cas2.

Unless defined otherwise, all technical and scientific terms used herein have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of the present disclosure employs, unless otherwise indicated, conventional techniques of biochemistry, chemistry, molecular biology, microbiology, cell biology, genomics, plant breeding, and biotechnology, which are within the skill of the art. See Green and Sambrook, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)); Harlow and Lane, eds. (1988) ANTIBODIES, A LABORATORY MANUAL; ANIMAL CELL CULTURE (R. I. Freshney, ed. (1987)); RECOMBINANT PROTEIN PURIFICATION: PRINCIPLES AND METHODS, 18-1142-75, GE Healthcare Life Sciences; C. N. Stewart, A. Touraev, V. Citovsky, T. Tzfira eds. (2011) PLANT TRANSFORMATION TECHNOLOGIES (Wiley-Blackwell); and R. H. Smith (2013) PLANT TISSUE CULTURE. TECHNIQUES AND EXPERIMENTS (Academic Press, Inc.).

Any references cited herein are incorporated by reference in their entireties.

As used herein, the singular form "a," "an," and "the" include plural references unless the context clearly dictates otherwise. For example, the term "a compound" or "at least one compound" may include a plurality of compounds, including mixtures thereof. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule.

As used herein, the term "about" indicates that a value includes the inherent variation of error for the method being employed to determine a value, or the variation that exists among experiments.

As used herein, the terms "CRISPR enzyme" and "CRISPR effector protein" are generally used interchangeably and refer by analogy to novel genome modification enzymes that utilize RNAs capable of hybridizing with a specific target sequence to guide the genome modification enzyme to the target site where it exerts its activity. In some embodiments, the novel RNA-guided genome modification enzymes are RNA-guided endonuclease (RGENs).

As used herein, "encoding" refers either to a polynucleotide (DNA or RNA) encoding for the amino acids of a polypeptide or a DNA encoding for the nucleotides of an RNA. As used herein, "coding sequence" and "coding region" are used interchangeably and refer to a polynucleotide that encodes a polypeptide. The boundaries of a coding region are generally determined by a translation start codon at its 5' end and a translation stop codon at its 3' end.

As used herein, an "endogenous" molecule is one that is normal present in a particular cell at a particular developmental stage under particular environmental conditions.

As used herein, an "expression cassette" refers to a polynucleotide sequence which may or may not be operably linked to one or more expression elements such as an enhancer, a promoter, a leader, an intron, a 5' untranslated region (UTR), a 3' UTR, or a transcription termination sequence. In some embodiments, an expression cassette comprises at least a first polynucleotide sequence capable of initiating transcription of an operably linked second polynucleotide sequence and optionally a transcription termination sequence operably linked to the second polynucleotide sequence.

As used herein, the term "gene" means a locatable region of genomic sequence corresponding to a unit of inheritance. A gene may include regulatory regions, such as promoters, enhancers, 5'-untranslated regions, intron regions, exon regions, 3'-untranslated regions, transcribed regions, and other functional sequence regions that may exist as native genes or transgenes in a plant or a mammalian genome. Depending upon the circumstances, the term "target gene" can refer to the full-length nucleotide sequence of a gene targeted for binding and/or cleavage or the nucleotide sequence of a portion of a gene targeted for binding and/or cleavage. A target gene can be an endogenous gene or a transgene.

As used herein, the term "genomic locus" refers to a specific location on a chromosome. A genomic locus may comprise a single nucleotide, a few nucleotides, a large number of nucleotides, a gene, a portion of a gene, a gene cluster, a multigene family or array of genes in a genomic region.

As used herein, the term "homologous recombination" refers to the exchange of nucleotide sequences at a conserved region shared by two genomic loci or by a donor DNA and a target site. Homologous recombination includes symmetric homologous recombination and asymmetric homologous recombination. Asymmetric homologous recombination may also be referred to as unequal recombination.

As used herein, the term "identity" when used in relation to nucleic acids, describes the degree of similarity between two or more nucleotide sequences. The percentage of "sequence identity" between two sequences can be determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. (1994) Nucl. Acids Res., 22: 4673-4680).

As used herein, a "non-coding sequence" can encode a functional RNA (e.g. transfer RNA, ribosomal RNA, microRNA, Piwi-interacting RNA), a promoter, an intron, an untranslated region of an mRNA (e.g., a 5' untranslated region or a 3' untranslated region), a pseudogene, a repeat sequence, or a transposable element. Non-coding sequences do not encode functional polypeptides.

As used herein, the terms "nucleic acid," "polynucleotide," and "oligonucleotide are used interchangeably and refer to deoxyribonuclotides (DNA), ribonucleotides (RNA), and functional analogues thereof, such as complementary DNA (cDNA) in linear or circular conformation. Nucleic acid molecules provided herein can be single stranded or double stranded. Nucleic acid molecules comprise the nucleotide bases adenine (A), guanine (G), thymine (T), cytosine (C). Uracil (U) replaces thymine in RNA molecules. Analogues of the natural nucleotide bases, as well as nucleotide bases that are modified in the base, sugar, and/or phosphate moieties are also provided herein. The symbol "N" can be used to represent any nucleotide base (e.g., A, G, C, T, or U). As used herein, "complementary" in reference to a nucleic acid molecule or nucleotide bases refers to A being complementary to T (or U), and G being complementary to C. Two complementary nucleic acid molecules are capable of hybridizing with each other under appropriate conditions. In an aspect of the present disclosure, two nucleic acid sequences are homologous if they have at least 70%, at least 75%, at least 80%, at least 85%, at least 90%, at least 95%, at least 96%, at least 97%, at least 98%, at least 99% or 100% sequence identity with each other.

As used herein, "operably linked" means that the operably linked nucleic acid sequences exhibit their desired function. For example, in an aspect of this disclosure, a provided DNA promoter sequence can initiate transcription of an operably linked DNA sequence into RNA. A nucleic acid sequence provided herein can be upstream or downstream of a physically or operably linked nucleic acid sequence. In an aspect, a first nucleic acid molecule provided herein is both physically linked and operably linked to a second nucleic acid molecule provided herein. In another aspect, a first nucleic acid molecule provided herein is neither physically linked nor operably linked to a second nucleic acid molecule provided herein. As used herein, "upstream" means the nucleic acid sequence is positioned before the 5' end of a linked nucleic acid sequence. As used herein, "downstream" means the nucleic acid sequence is positioned after the 3' end of a linked nucleic acid sequence.

As used herein, the term "plant" refers to any photosynthetic, eukaryotic, unicellular or multicellular organism of the kingdom Plantae and includes a whole plant or a cell or tissue culture derived from a plant, comprising any of: whole plants, plant components or organs (e.g., leaves, stems, roots, etc.), plant tissues, seeds, plant cells, protoplasts and/or progeny of the same. A progeny plant can be from any filial generation, e.g., F1, F2, F3, F4, F5, F6, F7, etc. A "plant cell" is a biological cell of a plant, taken from a plant or derived through culture from a cell taken from a plant. The term plant encompasses monocotyledonous and dicotyledonous plants. The methods, systems, and compositions described herein are useful across a broad range of plants. Suitable plants in which the methods, systems, and compositions disclosed herein can be used include, but are not limited to, cereals and forage grasses (e.g., alfalfa, rice, maize, wheat, barley, oat, sorghum, pearl millet, finger millet, cool-season forage grasses, and bahiagrass), oilseed crops (e.g., soybean, oilseed brassicas including canola and oilseed rape, sunflower, peanut, flax, sesame, and safflower), legume grains and forages (e.g., common bean, cowpea, pea, faba bean, lentil, tepary bean, Asiatic beans, pigeonpea, vetch, chickpea, lupine, alfalfa, and clovers), temperate fruits and nuts (e.g., apple, pear, peach, plums, berry crops, cherries, grapes, olive, almond, and Persian walnut), tropical and subtropical fruits and nuts (e.g., citrus including limes, oranges, and grapefruit; banana and plantain, pineapple, papaya, mango, avocado, kiwifruit, passionfruit, and persimmon), vegetable crops (e.g., solanaceous plants including tomato, eggplant, and peppers; vegetable brassicas;

radish, carrot, cucurbits, alliums, asparagus, and leafy vegetables), sugar cane, tubers (e.g., beets, parsnips, potatoes, turnips, sweet potatoes), and fiber crops (sugarcane, sugar beet, stevia, potato, sweet potato, cassava, and cotton), plantation crops, ornamentals, and turf grasses (tobacco, coffee, cocoa, tea, rubber tree, medicinal plants, ornamentals, and turf grasses), and forest tree species.

As used herein, "plant genome" refers to a nuclear genome, a mitochondrial genome, or a plastid (e.g., chloroplast) genome of a plant cell. In some embodiments, a plant genome may comprise a parental genome contributed by the male and a parental genome contributed by the female. In some embodiments, a plant genome may comprise only one parental genome.

As used herein, "polynucleotide" refers to a nucleic acid molecule containing multiple nucleotides and generally refers both to "oligonucleotides" (a polynucleotide molecule of 18-25 nucleotides in length) and polynucleotides of 26 or more nucleotides. Aspects of this disclosure include compositions including oligonucleotides having a length of 18-25 nucleotides (e. g., 18-mers, 19-mers, 20-mers, 21-mers, 22-mers, 23-mers, 24-mers, or 25-mers), or medium-length polynucleotides having a length of 26 or more nucleotides (e. g., polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e. g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

As used herein, terms "polypeptide", "peptide" and "protein" are used interchangeably to refer to a polymer of amino acid residues. The term also applies to amino acid polymers in which one or more amino acids are chemical analogues or modified derivatives of a corresponding naturally-occurring amino acids.

As used herein, "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

As used herein, "promoter" refers to a nucleic acid sequence located upstream or 5' to a translational start codon of an open reading frame (or protein-coding region) of a gene and that is involved in recognition and binding of RNA polymerase I, II, or III and other proteins (trans-acting transcription factors) to initiate transcription. In some embodiments described herein, the promoter is a plant promoter. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, plant part, or cell type, a promoter may display "enhanced" expression, i.e., a higher level of expression, in one cell type, tissue, or plant part of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners. In an aspect, a promotor provided herein is a constitutive promoter. In another aspect, a promoter provided herein is a regulatable promoter. In an aspect, a promoter provided herein is located within a sequence of interest. In another aspect, a promoter provided herein is not located within a sequence of interest. A number of promoters that are active in plant cells have been described in the literature. Such promoters would include but are not limited to the nopaline synthase (NOS) (Ebert et al., 1987) and octopine synthase (OCS) promoters that are carried on Ti plasmids of *Agrobacterium tumefaciens*, the caulimovirus promoters such as the cauliflower mosaic virus (CaMV) 19S (Lawton et al., Plant Molecular Biology (1987) 9: 315-324) and 35S promoters (Odell et al., Nature (1985) 313: 810-812), the Figwort mosaic virus (FMV) 35S promoter (U.S. Pat. Nos. 6,051,753; 5,378,619), and the enhanced CaMV35S promoter (e35S). Additional promoters that can find use are the sucrose synthase promoter (Yang and Russell, Proceedings of the National Academy of Sciences, USA (1990) 87: 4144-4148), the R gene complex promoter (Chandler et al., Plant Cell (1989) 1: 1175-1183), and the chlorophyll a/b binding protein gene promoter, PC1SV (U.S. Pat. No. 5,850,019), and AGRtu.nos (GenBank Accession V00087; Depicker et al., Journal of Molecular and Applied Genetics (1982) 1: 561-573; Bevan et al., 1983) promoters. A variety of other plant gene promoters that are regulated in response to environmental, hormonal, chemical, and/or developmental signals, also can be used for expression of heterologous genes in plant cells, including, for instance, promoters regulated by (1) heat (Callis et al., Plant Physiology, (1988) 88: 965-968), (2) light (e.g., pea RbcS-3A promoter, Kuhlemeier et al., Plant Cell, (1989) 1: 471-478; maize RbcS promoter, Schaffner et al., Plant Cell (1991) 3: 997-1012); (3) hormones, such as abscisic acid (Marcotte et al., Plant Cell, (1989) 1: 969-976), (4) wounding (e.g., Siebertz et al., Plant Cell, (1989) 961-968); or other signals or chemicals. Tissue specific promoters are also known. In some embodiments, a promoter is capable of causing sufficient expression to result in the production of an effective amount of the gene product of interest. Examples describing such promoters include without limitation U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No.

6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429, 357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252, 138 (pathogen inducible promoters), U.S. Pat. No. 6,175, 060 (phosphorus deficiency inducible promoters), U.S. Pat. No. 6,635,806 (gamma-coixin promoter), and U.S. patent application Ser. No. 09/757,089 (maize chloroplast aldolase promoter). In some embodiments, promoter hybrids can be constructed to enhance transcriptional activity (U.S. Pat. No. 5,106,739). In some embodiments, promoter hybrids can be constructed to combine a desired transcriptional activity, transcriptional inducibility, transcriptional tissue specificity, and/or transcriptional developmental specificity. Promoters that function in plants include but are not limited to promoters that are inducible, viral, synthetic, constitutive, temporally regulated, spatially regulated, and spatio-temporally regulated. Other promoters that are tissue-enhanced, tissue-specific, or developmentally regulated are also known in the art and envisioned to have utility in the practice of this disclosure. Promoters used in the provided nucleic acid molecules and transformation vectors of the present disclosure can be modified, if desired, to affect their control characteristics. Promoters can be derived by means of ligation with operator regions, random or controlled mutagenesis, etc. Furthermore, the promoters can be altered to contain multiple "enhancer sequences" to assist in elevating gene expression.

As used herein, a "recombinant nucleic acid" refers to a nucleic acid molecule (DNA or RNA) having a coding and/or non-coding sequence distinguishable from endogenous nucleic acids found in natural systems. In some aspects, a recombinant nucleic acid provided herein is used in any composition, system or method provided herein. In some aspects, a recombinant nucleic acid may any CRISPR enzyme provided herein can be used in any composition, system or method provided herein. In some aspects, a recombinant nucleic acid may comprise or encode any guide RNA provided herein can be used in any composition, system or method provided herein. In some aspects, a recombinant nucleic acid can comprise any donor polynucleotide provided herein can be used in any composition, system or method provided herein. In an aspect, a vector provided herein comprises any recombinant nucleic acid provided herein. In another aspect, a cell provided herein comprises a recombinant nucleic acid provided herein. In another aspect, a cell provided herein comprises a vector provided herein.

As used herein, the term "recombination" refers to the process by which two DNA molecules exchange nucleotide sequences. In some aspects, the compositions, systems or methods provided herein promote recombination between two DNA molecules. In some embodiments, recombination occurs between two sets of parental chromosomes. In some embodiments, recombination occurs between two homologous chromosomes. In some embodiments, recombination occurs between non-homologous chromosomes. In some embodiments, recombination occurs between homologous chromosomes. In some embodiments, recombination results in the production of a new gene sequence, number of genes, arrangement of genes, allele or combination of alleles. Many methods for detecting recombination are know in the art and include, but are not limited to, 1) phenotypic screening, 2) molecular marker technologies such as single nucleotide polymorphism—SNP analysis by TaqMan® or Illumina/ Infinium technology, 3) Southern blot, and 4) sequencing.

As used herein, the term "recombination event" refers to an instance of recombination between two DNA molecules.

As used herein, the term "recombination rate" refers to the probability that a recombination event will occur between two genomic loci. The recombination rate may be influenced by a number of factors, including, but not limited to, the distance between two genomic loci, the chromosomal region (e.g., centromereic, telomereic) in which the loci occur, transcriptional activity, the presence of chromosomal inversions and other factors. Methods for measuring recombination include, but are not limited to, linkage analysis in mapping populations, and quantitative technologies such as quantitative PCR (qPCR) or droplet digital PCR (ddPCR), as described in the present disclosure. In some aspects, the compositions, systems or methods provided herein increase the recombination rate. As used herein, the term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as meristem, or particular cell types (e.g., pollen). Regulatory elements may also direct expression in a temporal-dependent manner, such as in a cell-cycle dependent or developmental stage-dependent manner, which may or may not also be tissue or cell-type specific. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); and SV40 enhancer.

As used herein, the terms "target sequence" or "target site" refer to a nucleotide sequence against which a guide RNA capable of hybridizing. A target sequence may be genic or non-genic. In some aspects, a target sequence provided herein comprises a genic region. In other aspects, a target sequence provided herein comprises an intergenic region. In yet another aspect, a target sequence provided herein comprises both a genic region and an intergenic region. In an aspect, a target sequence provided herein comprises a coding nucleic acid sequence. In another aspect, a target sequence provided herein comprises a non-coding nucleic acid sequence. In an aspect, a target sequence provided herein is located in a promoter. In another aspect, a target sequence provided herein comprises an enhancer sequence. In yet another aspect, a target sequence provided herein comprises both a coding nucleic acid sequence and a non-coding nucleic acid sequence. In one aspect, a target sequence provided herein is recognized and cleaved by a double-strand break inducing agent, such as a system comprising a CRISPR enzyme and a guide RNA.

Novel CRISPR Enzymes

The present disclosure provides polynucleotide sequences and amino acid sequences of novel CRISPR enzymes identified from various bacterial genomes. In some embodiments, the CRISPR enzymes provided herein comprise an amino acid sequence selected from SEQ ID NOs: 1-36, 73 and 75-87, fragments thereof, homologs thereof and orthologs thereof. The terms "ortholog" and "homolog" are well known in the art. A "homologue" of a CRISPR enzyme as described herein is a protein of the same species which performs the same or a similar function as the protein it is a homolog of. Homologous proteins may, but need not, be structurally related, or are only partially structurally related. An "ortholog" of a CRISPR enzyme as described herein is a protein of a different species which performs the same or a similar function as the protein it is an ortholog Orthologous proteins may but need not be structurally related, or are only partially structurally related. Homologs and orthologs may be identified by homology modeling or structural BLAST (Dey F, Cliff Zhang Q, Petrey D, Honig B. Toward a "structural BLAST": using structural relationships to infer function. Protein Sci. 2013 April; 22(4):359-66. doi: 10.1002/pro.2225.). In some embodiments, the homolog or ortholog of a novel CRISPR enzyme as described herein has a sequence homology or identity of at least 80%, at least 85%, at least 90%, at least 95%, at least 96%, at least 97%, at least 98%, or at least 99% with a CRISPR enzyme comprising an amino acid sequence selected from SEQ ID NOs: 1-36, 73 and 75-87.

In some embodiments, the CRISPR enzymes provided herein form a complex with a guide RNA that directs the CRISPR enzyme to a target site where the CRISPR enzyme introduces a single-strand break or a double-strand break (DSB) in a nucleic acid sequence. The targeted nucleic acid sequence can be DNA, RNA, or a DNA/RNA hybrid. The introduced DSB can be repaired by non-homologous end joining (NHEJ) creating high likelihood of introducing small insertions or deletions (Indels) leading to frame shift mutations. Alternatively, a DNA sequence with desired mutation can be substituted at the region of DSB when homology dependent repair (HDR) pathway is applied. In some embodiments a recombinant nucleic acid comprising a one or more transgenes is integrated at the target site.

The instant disclosure also provides a recombinant nucleic acid comprising a heterologous promoter operably linked to a polynucleotide encoding a CRISPR enzyme as described herein. In some embodiments, the CRISPR enzymes provided herein are encoded by a polynucleotide sequence comprising a sequence selected from SEQ ID NOs: 37-72, 74, 88-100 and 300-799, or a fragment thereof. In some embodiments, the CRISPR enzymes provided herein are encoded by a polynucleotide sequence comprising a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity to a sequence selected from SEQ ID NOs: 37-72, 74, 88-100 and 300-799, or a fragment thereof. In one aspect, a recombinant nucleic acid provided herein comprises one or more, two or more, three or more, four or more, five or more, six or more, seven or more, eight or more, nine or more, or ten or more heterologous promoters operably linked to one or more, two or more, three or more, four or more, five or more, six or more, seven or more, eight or more, nine or more, or ten or more polynucleotides encoding a CRISPR enzyme. In some embodiments, a recombinant nucleic acid provided herein encodes one or more, two or more, three or more, four or more, five or more, six or more, seven or more, eight or more, nine or more, or ten or more guide RNAs. As used herein, the term "guide RNA" refers to an RNA molecule comprising a nucleotide sequence that can guide CRISPR enzyme to a target DNA molecule by hybridizing to a target sequence. In one aspect, a guide RNA provided herein comprises a CRISPR RNA (crRNA). In one aspect, a guide RNA provided herein comprises a CRISPR RNA (crRNA) complexed with a trans-activating CRISPR RNA (tracrRNA). In another aspect, a guide RNA provided herein comprises a single-chain guide RNA. In an aspect, a single-chain guide RNA provided herein comprises both a crRNA and a tracrRNA.

In some embodiments, a recombinant nucleic acid provided herein comprises a polynucleotide encoding a guide RNA. In an aspect, a recombinant nucleic acid provided herein comprises one or more, two or more, three or more, four or more, five or more, six or more, seven or more, eight or more, nine or more, or ten or more polynucleotides encoding one or more, two or more, three or more, four or more, five or more, six or more, seven or more, eight or more, nine or more, or ten or more guide RNAs. In one aspect, a polynucleotide encoding a guide RNA provided herein is operably linked to a second promoter. In another aspect, a guide RNA provided herein is an isolated RNA. In an aspect, a guide RNA provided herein is encoded in a viral vector, a plasmid vector, or an *Agrobacterium* vector. In an aspect, a guide RNA provided herein comprises a crRNA. In an aspect, a guide RNA provided herein comprises a tracrRNA. In another aspect, a guide RNA provided herein comprises a single-chain guide RNA. In an aspect, a single-chain guide RNA provided herein comprises both a crRNA and a tracrRNA.

In some embodiments, a recombinant nucleic acid provided herein comprises one or more, two or more, three or more, four or more, five or more, six or more, seven or more, eight or more, nine or more, or ten or more donor polynucleotides. As used herein, a "donor polynucleotide" is a polynucleotide molecule capable of being inserted into a genome of a recipient cell using a CRISPR/Cas system or method as described herein. In another aspect, a donor polynucleotide provided herein is operably linked to a second promoter. In yet another aspect, a donor polynucleotide provided herein comprises at least one promoter. In an aspect, a donor polynucleotide provided herein comprises one or more, two or more, three or more, four or more, five or more, six or more, seven or more, eight or more, nine or more, or ten or more transgenes. In an aspect, a donor polynucleotide provided herein comprises one or more, two or more, three or more, four or more, five or more, six or more, seven or more, eight or more, nine or more, or ten or more coding nucleic acid sequences, one or more, two or more, three or more, four or more, five or more, six or more, seven or more, eight or more, nine or more, or ten or more non-coding nucleic acid sequences, or a combination of one or more, two or more, three or more, four or more, five or more, six or more, seven or more, eight or more, nine or more, or ten or more coding nucleic acid sequences and one or more, two or more, three or more, four or more, five or more, six or more, seven or more, eight or more, nine or more, or ten or more non-coding nucleic acid sequences. In an aspect, a donor polynucleotide provided herein comprises one or more, two or more, three or more, four or more, five or more, six or more, seven or more, eight or more, nine or more, or ten or more nucleic acid sequences for templated editing. In some embodiments, a recombinant nucleic acid comprising a donor polynucleotide is provided to a cell in the same vector as a CRISPR enzyme. In some embodiments, a recombinant nucleic acid comprising a donor polynucleotide is provided to a cell independently of a CRISPR enzyme. In an aspect, a donor polynucleotide provided herein is encoded in a viral vector, a plasmid vector, or an *Agrobacterium* vector.

In some embodiments, a polynucleotide encoding the CRISPR enzyme is from the genome of a bacterium selected from the group consisting of: *Lysinibacillus* sp., *Brevibacillus* sp., *Sphingobium* sp., *Undibacterium* sp., *Bacillus* sp., *Chryseobacterium* sp., *Sphingomonas* sp., and *Labrys* sp. In other embodiments, a polynucleotide encoding the CRISPR enzyme is from the genome of a bacterium selected from the group consisting of: *Brevibacillus laterosporus; Bacillus thuringiensis; Enterococcus faecalis; Brevibacillus brevis; Undibacterium pigrum; Novosphingobium rosa; Labrys methylaminiphilus; Brevibacillus parabrevis*. In certain aspects, a polynucleotide encoding the CRISPR enzyme is associated within the bacterial genome with a type II CRISPR repeat. In certain aspects, a polynucleotide encoding the CRISPR enzyme is further identified in the bacterial genome by associated with a Cas1, a Cas2, or a Cas1 and a Cas2 but not Cas5 or Cas3. In some embodiments, the polynucleotide encoding the CRISPR enzyme is located in the same operon as the CRISPR locus. In other embodiments, the polynucleotide encoding the CRISPR enzyme is located within 2 kilobases of the CRISPR loci. In another embodiment, the polynucleotide encoding the CRISPR enzyme is further identified by the presence of one or more pfam domains identified in Table 1. In an aspect, a polynucleotide encoding an CRISPR enzyme provided herein is characterized by: being from a genome of a *Lysinibacillus* sp., a *Brevibacillus* sp., a *Sphingobium* sp., a *Undibacterium* sp., a *Bacillus* sp., a *Chryseobacterium* sp., a *Sphingomonas* sp., or a *Labrys* sp.; being from a genome of *Bacillus thuringiensis, Brevibacillus brevis, Brevibacillus laterosporus, Brevibacillus parabrevis, Enterococcus faecalis, Labrys methylaminiphilus, Novosphingobium rosa*, or *Undibacterium pigrum*; being associated with a bacterial genome by association with a type II CRISPR repeat; being identified in a bacterial genome by association with a Cas1 protein, a Cas2 protein, or a Cast protein and a Cas2 protein, but not a Cas3 protein or Cas5 protein; being located in the same operon as a CRISPR loci; being located within 10, 25, 50, 75, 100, 150, 200, 250, 500, 550, 600, 650, 700, 750, 800, 850, 900, 950, 1000, 1250, 1500, 1750, 2000, 2500, 3000, 4000, 5000, 7500, or 10,000 nucleotides of a CRISPR loci; being a polynucleotide comprising a sequence having at least 80%, at least 85%, at least 90%, at least 91%, at least 92%, at least 93%, at least 94%, at least 95%, at least 96%, at least 97%, at least 98%, at least 99% or 100% identity to a sequence selected from SEQ ID NOs: 37-72, 74, and 88-100; and any combination thereof.

Several embodiments described herein relate to targeted genome modification in eukaryotic cells, for example, plant cells. Some embodiments relate to a composition for cleaving a target DNA comprising a guide RNA specific for the target DNA and a CRISPR enzyme as described herein, and the use thereof. In some embodiments, the CRISPR enzyme is selected from the group consisting of SEQ ID NOs:1-36, 73 and 75-87, homologs thereof and orthologs thereof. In some embodiments, a complex comprising CRISPR enzyme and a guide RNA specific for a target DNA is described. In some embodiments, the complex further comprises a divalent cation. In some embodiments the CRISPR enzyme, when complexed with a guide RNA, effects cleavage of the target DNA thereby modifying the target DNA. In some embodiments, cleavage comprises cleaving one or two strands at the location of the target DNA by the CRISPR enzyme. In some embodiments, formation of a complex comprising a CRISPR enzyme and a guide RNA results in cleavage of one or both strands in or near (e.g. within 1, 2, 3, 4, 5, 6, 7, 8, 9, 10, 20, 50, or more base pairs from) the target sequence. In some embodiments, cleavage results in decreased transcription of a target gene. In some embodiments, cleavage results in an increase recombination rate between two genomic loci. In some embodiments, cleavage results in integration of one ore more transgenes. In some embodiments, cleavage results in integration of a cis-genic sequence. In some embodiments, cleavage results in an insertion or deletion of nucleotides at or near the target sequence. In some embodiments, the cleaved target DNA is repaired by homologous recombination with an exogenous template polynucleotide. In some embodiments, the template polynucleotide comprises one or more exogenous transgenes. In some embodiments, the one or more exogenous transgenes are flanked by sequence homologous to the cleavage site. In some embodiments, the template polynucleotide comprises a sequence that has at least at least 85% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least 50 bp, at least 100 bp, at least 150 bp, at least 200 bp, at least 250 bp, at least 300 bp, at least 350 bp, at least 400 bp, at least 450 bp, at least 500 bp, at least 550 bp, at least 600 bp, at least 650 bp, at least 700 bp, at least 750 bp, at least 800 bp, at least 850 bp, at least 900 bp, at least 950 bp, or at least 1,000 bp of a nucleic acid sequence comprising the target sequence. In some embodiments, the template polynucleotide comprises 1, 2, 3, 4, 5, 6, 7, 8, 9, 10 or more nucleotide mutations compared to the target sequence. In some embodiments, the cleaved target DNA is repaired by non-homologous end joining (NHEJ) wherein said repair results in a mutation comprising an insertion, deletion, or substitution of one or more nucleotides of said target DNA.

Several embodiments relate to a method of modifying a targeted DNA sequence in a eukaryotic cell. In some embodiments, the method comprises allowing a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 1 36, 73 and 75-87 and a guide RNA complex to bind to the targeted DNA sequence such that said binding results in cleavage of the targeted DNA sequence. In some embodiments, the method comprises delivering one or more vectors to said eukaryotic cells, wherein the one or more vectors drive expression of one or more of: the CRISPR enzyme, the guide RNA, and a donor polynucleotide.

In an aspect, the disclosure provides methods of identifying putative CRISPR enzymes from bacterial genomes. In some embodiments, the method comprises: (a) identification of large protein sequences (approximately 1,000 amino acids); (b) that these protein sequences were annotated as an endonuclease or Cas9 or contained an HNH pfam domain; (c) were located in the same operon with a Cast and a Cas2, but not a Cas5 or a Cas3; and that the proteins were in the same operon within <2 kb of a CRISPR loci. In some embodiments, the method comprises: (a) identification of large protein sequences (approximately 1,000 amino acids); (b) that these protein sequences were annotated as an endonuclease or Cas9 or contained an HNH pfam domain; (c) were located in the same operon with a Cast or a Cas2, but not a Cas5 or a Cas3; and that the proteins were in the same operon within <2 kb of a CRISPR loci. Results were additionally reviewed to identify un-annotated Cas2.

Nucleic Acid-Targeting System and Components Thereof

The present disclosure provides a nucleic acid-targeting system for sequence-specific modification of a target nucleic acid sequence. As used herein, the terms "nucleic acid-targeting system" or "nucleic acid-targeting complex" refer collectively to transcripts and other elements involved in the expression of or directing the activity of nucleic acid-targeting effector protein genes, which may include sequences encoding a nucleic acid-targeting effector protein and a nucleic acid-targeting guide RNA. In some embodiments, the nucleic acid-targeting effector protein is a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 1-36, 73 and 75-87. In some embodiments, the nucleic acid-targeting system is a CRISPR-Cas system, which comprises a CRISPR RNA (crRNA) sequence and may comprise (in some systems, but not all systems) a trans-activating CRISPR RNA (tracrRNA) sequence, or other sequences and transcripts from a CRISPR locus. In some systems, a tracrRNA sequence is not required. In other systems, a tracrRNA sequence is required. In some embodiments, the targeted nucleic acid is DNA or RNA. In other embodiments, the targeted nucleic acid is a DNA-RNA hybrid or derivatives thereof. In general, a RNA-targeting system is characterized by elements that promote the formation of a RNA-targeting complex at the site of a target RNA sequence. In the context of formation of a DNA or RNA-targeting complex, "target sequence" refers to a DNA or RNA sequence to which a DNA or RNA-targeting guide RNA is designed to have complementarity, where hybridization between a target sequence and a RNA-targeting guide RNA promotes the formation of a RNA-targeting complex. In some embodiments, a target sequence is located in the nucleus or cytoplasm of a cell.

In an embodiment, the nucleic acid-targeting system comprises (a) a guide RNA or a DNA molecule encoding a guide RNA, wherein the guide RNA is specific for a target nucleic acid sequence, and (b) a polynucleotide encoding a CRISPR enzyme. In a further embodiment, the CRISPR enzyme comprises an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 1-36, 73 and 75-87. In some embodiments, the CRISPR enzyme comprises an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 1-36. In some embodiments, the CRISPR enzyme comprises an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87. In another embodiment, the polynucleotide encoding the CRISPR enzyme comprises a nucleotide sequence selected from the group consisting of SEQ ID NOs: 37-72, 74, 88-100 and 300-799. In some embodiments, the guide RNA or a DNA molecule encoding a guide RNA is provided on a first nucleic acid molecule and the polynucleotide encoding the CRISPR enzyme is provided on a second nucleic acid molecule. In other embodiments, the guide RNA or a DNA molecule encoding a guide RNA and the polynucleotide encoding a CRISPR enzyme is are provided on a single nucleic acid molecule. In some embodiments, the guide RNA comprises one or more crRNA sequences provided in Table 3. In some embodiments, the guide RNA comprises one or more tracrRNA sequences provided in Table 3. In some embodiments, the guide RNA comprises one or more crRNA sequences provided in Table 5. In some embodiments, the guide RNA comprises one or more tracrRNA sequences provided in Table 5. In some embodiments, the guide RNA comprises one or more fused tracrRNA:crRNA sequences provided in Table 5.

In some embodiments, the target nucleic acid sequence comprises coding sequence, non-coding sequence, or a combination of coding and non-coding sequence. In some embodiments, the target nucleic acid sequence comprises an endogenous gene or a transgene.

In some embodiments, the guide RNA comprises a crRNA and a tracrRNA. In some embodiments, the guide RNA comprises a single-chain guide RNA. In some embodiments, the guide RNA comprises a single-chain guide RNA comprising a crRNA. In some embodiments, the crRNA comprises a crRNA sequence provided in Tables 3 and 5.

In some embodiments, the nucleic acid-targeting system disclosed herein further comprises a donor polynucleotide. In some embodiments, the donor polynucleotide comprises a coding sequence, a non-coding sequence, or a combination of coding and non-coding sequence. In some embodiments, the donor polynucleotide comprises a promoter. In some embodiments, the donor polynucleotide comprises a regulatory element. In some embodiments, the donor polynucleotide comprises one or more transgenes.

As used herein, the term "guide RNA" refers to any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 91%, 92%, 93%, 94%, 95%, 96%, 97%, 98%, 99%, or more. Optimal alignment may be determined with the use of any suitable algorithm for aligning sequences.

In some embodiments, the guide RNA comprises a mature crRNA. In certain embodiments, the mature crRNA comprises, consists essentially of, or consists of a direct repeat sequence and a guide sequence or spacer sequence. Examples of direct repeat sequences and spacer sequences may be found in Table 2. Examples of crRNA sequences may be found in Tables 3 and 5. In certain embodiments, the guide RNA comprises, consists essentially of, or consists of a direct repeat sequence linked to a guide sequence or spacer sequence. In some embodiments, a guide RNA sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide RNA sequence is less than about 75, 50, 45, 40, 35, 30, 25, 20, 15, 12, or fewer nucleotides in length. In some embodiments, the guide RNA sequence is 10-30 nucleotides long. In some embodiments, the guide RNA sequence is 10-20 nucleotides long. A guide RNA sequence may be selected to target any target sequence. In some embodiments, the target sequence is a sequence within a genome of a cell. In some embodiments, the target sequence is unique in the target genome.

In some embodiments, the mature crRNA comprises a stem loop or an optimized stem loop structure or an optimized secondary structure. In some embodiments the mature crRNA comprises a stem loop or an optimized stem loop structure in the direct repeat sequence, wherein the stem loop or optimized stem loop structure is important for cleavage activity. In certain embodiments, the mature crRNA comprises a single stem loop. In certain embodiments, the direct repeat sequence comprises a single stem loop. In certain embodiments, the cleavage activity of the nucleic acid-targeting system is modified by introducing mutations that affect the stem loop RNA duplex structure. In some embodiments, mutations which maintain the RNA duplex of the stem loop may be introduced, whereby the cleavage activity of the nucleic acid-targeting system is maintained. In other embodiments, mutations which disrupt the RNA duplex structure of the stem loop may be introduced, whereby the cleavage activity of the nucleic acid-targeting system is completely abolished.

The ability of a guide RNA sequence to direct sequence-specific binding of a nucleic acid-targeting complex to a target nucleic acid sequence may be assessed by any suitable assay. For example, the components of a nucleic acid-targeting system sufficient to form a nucleic acid-targeting complex, including the CRISPR enzyme and guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence. Similarly, cleavage of a target nucleic acid sequence may be evaluated in vitro by providing the target nucleic acid sequence, components of a nucleic acid-targeting complex, including the CRISPR enzyme and guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide RNA may be selected to target any target nucleic acid sequence. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non coding RNA (ncRNA), long non-coding RNA (lncRNA), and small cytoplasmatic RNA (scRNA). In some embodiments, the target sequence may be a sequence within a RNA molecule selected from the group consisting of mRNA, pre-mRNA, and rRNA. In some embodiments, the target sequence may be a sequence within a RNA molecule selected from the group consisting of ncRNA, and lncRNA. In some embodiments, the target sequence may be a sequence within an mRNA molecule or a pre-mRNA molecule.

As used herein, the term "tracrRNA" includes any polynucleotide sequence that has sufficient complementarity with a crRNA sequence to hybridize. In some embodiments, the tracrRNA is not required for cleavage activity of a nucleic acid-targeting system. In other embodiments, the tracrRNA is required for cleavage activity of a nucleic acid-targeting system. Examples of tracrRNA sequences may be found in Tables 3 and 5.

Several embodiments described herein relate to a nucleic acid-targeting system comprising (a) comprises a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87 one or more and (b) a guide RNA capable of hybridizing with a target sequence. In some embodiments, the nucleic acid-targeting system further comprises a tracrRNA. In some embodiments, the nucleic acid-targeting system further comprises a divalent cation. In some embodiments, the nucleic acid-targeting system further comprises Mg2+. In some embodiments, the nuclease activity of the CRISPR enzyme is inactivated. In some embodiments, the nucleic acid-targeting system further comprises a CRISPR enzyme with a heterologous functional domain. In some embodiments, the nucleic acid-targeting system is functional in a eukaryotic cell. In some embodiments, the nucleic acid-targeting system is functional in a plant cell.

In some embodiments, one of more components of a nucleic acid-targeting system disclosed herein are expressed or delivered in a vector. As used herein, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid", which refers to a circular double stranded DNA loop into which additional DNA segments can be inserted, such as by standard molecular cloning techniques. Another type of vector is an *Agrobacterium*. Another type of vector is a viral vector, wherein virally-derived DNA or RNA sequences are present in the vector for packaging into a virus (e.g., retroviruses, replication defective retroviruses, Tobacco mosaic virus (TMV), Potato virus X (PVX) and Cowpea mosaic virus (CPMV), tobamovirus, Gemini viruses, adenoviruses, replication defective adenoviruses, and adeno-associated viruses). Viral vectors also include polynucleotides carried by a virus for transfection into a host cell. In some embodiments, a viral vector may be delivered to a plant using *Agrobacterium*. Certain vectors are capable of autonomous replication in a host cell into which they are introduced. Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". Vectors for and that result in expression in a eukaryotic cell can be referred to herein as "eukaryotic expression vectors." Common expression vectors of utility in recombinant DNA techniques are often in the form of plasmids. It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Recombinant expression vectors can comprise a nucleic acid of the disclosure in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed.

As used herein, the terms "template nucleic acid" or "donor polynucleotide" may be used interchangeably and refer to a nucleic acid sequence which can be used in conjunction with CRISPR enzyme, in particular a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 1-36, 73 and 75-87 or an ortholog or homolog thereof, and a guide RNA molecule to alter the structure of a target position. In some embodiments, the template nucleic acid or donor polynucleotide comprises one or more, two or more, three or more, four or more, five or more transgenes. In an embodiment, the target position is modified to have some or all of the sequence of the template nucleic acid, typically at or near cleavage site(s). In an embodiment, the template nucleic acid is single stranded. In an alternate embodiment, the template nucleic acid is double stranded. In an embodiment, the template nucleic acid is DNA, e.g., double stranded DNA. In an alternate embodiment, the template nucleic acid is single stranded DNA.

In an embodiment, the template nucleic acid alters the structure of the target sequence by participating in homologous recombination. In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a nucleic acid-targeting system mediated cleavage event. In an embodiment, the template nucleic acid may include sequence that corresponds to both, a first site on the target sequence that is cleaved in a first nucleic acid-targeting system mediated event, and a second site on the target sequence that is cleaved in a second nucleic acid-targeting system mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a regulatory element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive regulatory element; increasing the activity of a positive regulatory element; decreasing the activity of a negative regulatory element; increasing the activity of a negative regulatory element; decreasing the expression of a gene; increasing the expression of a gene; increasing resistance to a herbicide; increasing resistance to a disease; increasing resistance to a insect or nematode pest; increasing resistance to an abiotic stress (e.g., drought, nitrogen deficiency); increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

In some embodiments, a template nucleic acid may include sequence which results in: a change in sequence of 1, 2, 3, 4, 5, 6, 7, 8, 9, 10, 11, 12 or more nucleotides of the target sequence. In an embodiment, the template nucleic acid may be 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 110+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, a donor nucleic acid comprises the following components: [5' homology arm]-[sequence of interest]-[3' homology arm]. The homology arms provide for recombination into the chromosome. In some embodiments, the sequence of interest replaces an undesired element, e.g., a mutation or signature, with the sequence of interest. In some embodiments, the sequence of interest comprises one or more, two or more, three or more, four or more, or five or more transgenes. In an embodiment, the homology arms flank the most distal cleavage sites. In an embodiment, the 3' end of the 5' homology arm is the position next to the 5' end of the sequence of interest. In an embodiment, the 5' homology arm can extend at least 10, 20, 30, 40, 50, 100, 200, 300, 400, 500, 600, 700, 800, 900, 1000, 1500, or 2000 nucleotides 5' from the 5' end of the sequence of interest. In an embodiment, the 5' end of the 3' homology arm is the position next to the 3' end of the sequence of interest. In an embodiment, the 3' homology arm can extend at least 10, 20, 30, 40, 50, 100, 200, 300, 400, 500, 600, 700, 800, 900, 1000, 1500, or 2000 nucleotides 3' from the 3' end of the sequence of interest.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In certain embodiments, a donor nucleic acid may designed for use as a single-stranded oligonucleotide. When using a single-stranded oligonucleotide, 5' and 3' homology arms may range up to about 200 bases in length, e.g., at least 25, 50, 75, 100, 125, 150, 175, or 200 bases in length.

In certain embodiments, the components of the nucleic acid-targeting system may further comprise at least one or more nuclear localization signal (NLS), nuclear export signal (NES), functional domain, flexible linker, mutation, deletion, alteration or truncation. The one or more of the NLS, the NES or the functional domain may be conditionally activated or inactivated.

In some embodiments, the nucleic acid-targeting system as described herein is functional at 20° C., 21° C., 22° C., 23° C., 24° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

In certain embodiments, one or more components of a nucleic acid-targeting system are comprised on one or more vectors for delivery to a eukaryotic cell. In some embodiments, one or more vector(s) encode(s): one or more of (i) one or more CRISPR enzymes, more particularly, one or more CRISPR enzymes comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 1-36, 73 and 75-87; (ii) a first guide RNA capable of hybridizing to a first target sequence in a cell; and optionally, (iii) a second guide RNA capable of hybridizing to a second target sequence in the cell, when expressed within the cell, the first guide RNA directs sequence-specific binding of a first nucleic acid-targeting complex to the first target sequence in the cell; the second guide RNA directs sequence-specific binding of a second nucleic acid-targeting complex to the second target sequence in the cell; the nucleic acid-targeting complexes comprise a CRISPR enzyme bound to a guide RNA, thereby a guide RNA can hybridize to its target sequence. The various coding sequences (CRISPR enzyme, guide RNAs) can be included on a single vector or on multiple vectors. For instance, it is possible to encode the CRISPR enzyme on one vector and the various RNA sequences on another vector, or to encode the CRISPR enzyme and various guide RNAs on one vector, and donor nucleic acids on additional vectors, or any other permutation. In an aspect, a system uses a total of one, two, three, four, five or more different vectors. Where multiple vectors are used, it is possible to deliver them in unequal numbers.

In certain embodiments, recombinant nucleic acids encoding guide RNAs may be designed in an array format such that multiple guide RNA sequences can be simultaneously released. In some embodiments, expression of one or more guide RNAS is U6-driven. In some embodiments, CRISPR enzymes complex with multiple guide RNAs to mediate genome editing and at multiple target sequences. Some embodiments relate to expression of singly or in tandem array format from 1 up to 4 or more different guide sequences; e.g. up to about 20 or about 30 guides sequences. Each individual guide sequence may target a different target sequence. Such may be processed from, e.g. one chimeric pol3 transcript. Pol3 promoters such as U6 or H1 promoters may be used. Pol2 promoters such as those mentioned throughout herein. Inverted terminal repeat (iTR) sequences may flank the Pol3 promoter-gRNA(s)-Pol2 promoter-Cas.

In another embodiment, a construct that will transiently express a gRNA and/or CRISPR enzyme is created and introduced into a cell. In yet another embodiment, the vector will produce sufficient quantities of the gRNAs and/or CRISPR enzyme in order for the desired episomal or genomic target site or sites to be effectively modified by a nucleic acid-targeting system as described herein. For instance, the disclosure contemplates preparation of a vector that can be bombarded, electroporated, chemically transfected or transported by some other means across the plant cell membrane. Such a vector could have several useful properties. For instance, in one embodiment, the vector can replicate in a bacterial host such that the vector can be produced and purified in sufficient quantities for transient expression. In another embodiment, the vector can encode a drug resistance gene to allow selection for the vector in a host, or the vector can also comprise an expression cassette to provide for the expression of the gRNA and/or CRISPR enzyme gene in a plant. In a further embodiment, the expression cassette could contain a promoter region, a 5' untranslated region, an optional intron to aid expression, a multiple cloning site to allow facile introduction of a sequence encoding gRNAs and/or CRISPR enzyme gene, and a 3' UTR. In particular embodiments, the promoters in the expression cassette would be U6 promoters from *Zea maize*. In yet other embodiments, the promoters would be chimeric U6 promoters from *Zea maize*. In some embodiments, it can be beneficial to include unique restriction sites at one or at each end of the expression cassette to allow the production and isolation of a linear expression cassette, which can then be free of other vector elements. The untranslated leader regions, in certain embodiments, can be plant-derived untranslated regions. Use of an intron, which can be plant-derived, is contemplated when the expression cassette is being transformed or transfected into a monocot cell.

In some embodiments, a recombinant nucleic acid as described herein may comprise multiple U6 promoters with differing sequences. A utility of having multiple U6 promoters with differing sequence is to minimize problems in vector stability, which is typically associated with sequence repeats. Further, highly repetitive regions in chromosomes may lead to genetic instability and silencing. Therefore, another utility of using multiple U6 promoters in the nucleic acid-targeting system is to facilitate vector stacking of multiple gRNA cassettes in the same transformation construct, where the differing gRNA transcript levels are to be maximized for efficient targeting of a single target site. Chimeric U6 promoters can result in new, functional versions with improved or otherwise modified expression levels.

In several embodiments, an expression vector comprises at least one expression cassette encoding one or more components of a nucleic acid-targeting system as described herein may comprise a promoter. In certain embodiments, the promoter is a constitutive promoter, a tissue specific promoter, a developmentally regulated promoter, or a cell cycle regulated promoter. Certain contemplated promoters include ones that only express in the germline or reproductive cells, among others. Such developmentally regulated promoters have the advantage of limiting the expression of the nucleic acid-targeting system to only those cells in which DNA is inherited in subsequent generations. Therefore, a nucleic acid-targeting system mediated genetic modification (i.e., chromosomal or episomal dsDNA cleavage) is limited only to cells that are involved in transmitting their genome from one generation to the next. This might be useful if broader expression of the nucleic acid-targeting system were genotoxic or had other unwanted effects. Examples of such promoters include the promoters of genes encoding DNA ligases, recombinases, replicases, and so on.

In some embodiments, the recombinant nucleic acid molecules described herein can be incorporated into any suitable plant transformation plasmid or vector. In some embodiments, the plant transformation plasmid or vector contains a selectable or screenable marker and associated regulatory elements as described, along with one or more nucleic acids encoded by a structural gene.

Inducible Nucleic Acid-Targeting System

In one aspect, the disclosure provides a non-naturally occurring or engineered nucleic acid-targeting system which may comprise at least one switch wherein the activity of the nucleic acid-targeting system is controlled by contact with at least one inducer energy source as to the switch. In an embodiment of the disclosure, the control as to the at least one switch or the activity of the nucleic acid-targeting system may be activated, enhanced, terminated or repressed. The contact with the at least one inducer energy source may result in a first effect and a second effect. The first effect may be one or more of nuclear import, nuclear export, recruitment of a secondary component (such as an effector molecule), conformational change (of protein, DNA or RNA), cleavage, release of cargo (such as a caged molecule or a co-factor), association or dissociation. The second effect may be one or more of activation, enhancement, termination or repression of the control as to the at least one switch or the activity of the nucleic acid-targeting system. In one embodiment the first effect and the second effect may occur in a cascade.

Aspects of control as detailed in this application relate to at least one or more switch(es). The term "switch" as used herein refers to a system or a set of components that act in a coordinated manner to affect a change, encompassing all aspects of biological function such as activation, repression, enhancement or termination of that function. In one aspect the term switch encompasses genetic switches which comprise the basic components of gene regulatory proteins and the specific DNA sequences that these proteins recognize. In one aspect, switches relate to inducible and repressible systems used in gene regulation. In general, an inducible system may be off unless there is the presence of some molecule (called an inducer) that allows for gene expression. The molecule is said to "induce expression". The manner by which this happens is dependent on the control mechanisms as well as differences in cell type. A repressible system is on except in the presence of some molecule (called a corepressor) that suppresses gene expression. The molecule is said to "repress expression". The manner by which this happens is dependent on the control mechanisms as well as differences in cell type. The term "inducible" as used herein may encompass all aspects of a switch irrespective of the molecular mechanism involved.

In another aspect of the disclosure the nucleic acid-targeting system may further comprise at least one or more nuclear localization signal (NLS), nuclear export signal (NES), functional domain, flexible linker, mutation, deletion, alteration or truncation. The one or more of the NLS, the NES or the functional domain may be conditionally activated or inactivated. In another embodiment, the mutation may be one or more of a mutation in a transcription factor homology region, a mutation in a DNA binding domain (such as mutating basic residues of a basic helix loop helix), a mutation in an endogenous NLS or a mutation in an endogenous NES. The disclosure comprehends that the inducer energy source may be heat, ultrasound, electromagnetic energy or chemical.

In some embodiments, the inducer energy source may be an antibiotic, a small molecule, a hormone, a hormone derivative, a steroid or a steroid derivative. In some embodiments, the inducer energy source maybe abscisic acid (ABA), salicylic acid, doxycycline (DOX), cumate, rapamycin, 4-hydroxytamoxifen (4OHT), estrogen or ecdysone. The disclosure provides that the at least one switch may be selected from the group consisting of antibiotic based inducible systems, electromagnetic energy based inducible systems, small molecule based inducible systems, nuclear receptor based inducible systems and hormone based inducible systems.

The present nucleic acid-targeting system may be designed to modulate or alter expression of individual endogenous genes in a temporally and spatially precise manner. The nucleic acid-targeting system may be designed to bind to the promoter sequence of the gene of interest to change gene expression.

Another system contemplated by the present disclosure is a chemical inducible system based on change in sub-cellular localization. An inducible nucleic acid-targeting system may be engineered to target a genomic locus of interest where the CRISPR enzyme is split into two fusion constructs that are further linked to different parts of a chemical or energy sensitive protein. This chemical or energy sensitive protein will lead to a change in the sub-cellular localization of either half of the CRISPR enzyme upon the binding of a chemical or energy transfer to the chemical or energy sensitive protein. This transportation of fusion constructs from one sub-cellular compartments or organelles, in which its activity is sequestered due to lack of substrate for the reconstituted nucleic acid-targeting system, into another one in which the substrate is present would allow the components to come together and reconstitute functional activity and to then come in contact with its desired substrate (i.e. genomic DNA in the mammalian nucleus) and result in activation or repression of target gene expression.

Other inducible systems are contemplated such as, but not limited to, regulation by heavy-metals, steroid hormones, heat shock and other reagents have been developed.

In particular embodiments, the nucleic acid-targeting systems described herein are placed under the control of a passcode kill switch, which is a mechanisms which efficiently kills the host cell when the conditions of the cell are altered. In some embodiments, this is ensured by introducing hybrid LacI-GalR family transcription factors, which require the presence of IPTG to be switched on (Chan et al. 2015 Nature Nature Chemical Biology doi:10.1038/nchembio.1979) which can be used to drive a gene encoding an enzyme critical for cell-survival. By combining different transcription factors sensitive to different chemicals, a "code" can be generated, This system can be used to spatially and temporally control the extent of nucleic acid-targeting system-induced genetic modifications, which can be of interest in different fields including therapeutic applications and may also be of interest to avoid the "escape" of transgene containing organisms from their intended environment.

Self-Inactivating Systems

In some embodiments, once all copies of a gene in the genome of a cell have been edited, continued nucleic acid-targeting system expression in that cell is no longer necessary. In some embodiments, sustained expression would be undesirable in case of off-target effects at unintended genomic sites, etc. In some embodiments, time-limited expression of components of the nucleic acid-targeting system would be useful. Inducible expression offers one approach, another approach may be a self-inactivating nucleic acid-targeting system that relies on the use of a non-coding guide target sequence within the vector itself. Thus, after expression begins, the nucleic acid-targeting system will lead to its own destruction, but before destruction is complete it will have time to edit the genomic copies of the target gene. In some embodiments, self inactivating nucleic acid-targeting system includes additional RNA (i.e., guide RNA) that targets the coding sequence for the CRISPR enzyme or that targets one or more non-coding guide target sequences complementary to unique sequences present in one or more of the following: (a) within the promoter driving expression of the non-coding RNA elements, (b) within the promoter driving expression of the RNA-guided nuclease gene, (c) within 100 bp of the ATG translational start codon in the RNA-guided nuclease coding sequence, (d) within the inverted terminal repeat (iTR) of a viral delivery vector.

In some embodiments, one or more guide RNA can be delivered via a vector, e.g., a separate vector or the same vector that is encoding the CRISPR enzyme. When provided by a separate vector, a guide RNA that targets CRISPR enzyme expression can be administered sequentially or simultaneously. When administered sequentially, the guide RNA that targets CRISPR enzyme expression may be delivered after the guide RNA that is intended for gene editing or genome engineering. This period may be a period of minutes (e.g. 5 minutes, 10 minutes, 20 minutes, 30 minutes, 45 minutes, 60 minutes). This period may be a period of hours (e.g. 2 hours, 4 hours, 6 hours, 8 hours, 12 hours, 24 hours). This period may be a period of days (e.g. 2 days, 3 days, 4 days, 7 days). This period may be a period of weeks (e.g. 2 weeks, 3 weeks, 4 weeks). This period may be a period of months (e.g. 2 months, 4 months, 8 months, 12 months). This period may be a period of years (2 years, 3 years, 4 years). In some embodiments, the CRISPR enzyme associates with a first guide RNA capable of hybridizing to a first target, such as a genomic locus or loci of interest and undertakes the function(s) desired of the nucleic acid-targeting system (e.g., gene engineering); and subsequently the CRISPR enzyme may then associate with the second guide RNA capable of hybridizing to the sequence encoding at least part of the CRISPR enzyme or CRISPR cassette. Where the guide RNA targets the sequences encoding expression of the CRISPR enzyme, the enzyme becomes impeded and the system becomes self inactivating. In some embodiments, guide RNA that targets CRISPR enzyme expression applied via, for example particle bombardment, lipofection, nanoparticles, microvesicles, may be administered sequentially or simultaneously. Similarly, self-inactivation may be used for inactivation of one or more guide RNA used to target one or more targets.

In some aspects, a single guide RNA is provided that is capable of hybridizing to a sequence downstream of a CRISPR enzyme start codon, thereby after a period of time there is a loss of CRISPR enzyme expression. In some aspects, one or more guide RNA(s) are provided that are capable of hybridizing to one or more coding or non-coding regions of the polynucleotide encoding one or more components the nucleic acid-targeting system, whereby after a period of time there is a inactivation of one or more, or in some cases all, of the components of the nucleic acid-targeting system. In some aspects, and not to be limited, a cell may comprise a plurality of nucleic acid-targeting complexes, where a first subset of nucleic acid-targeting complexes comprise a first guide RNA capable of targeting a genomic locus or loci to be edited, and a second subset of nucleic acid-targeting complexes comprise at least one second guide RNA capable of targeting the polynucleotide encoding one or more components of the nucleic acid-targeting system, where the first subset of nucleic acid-targeting complexes mediate editing of the targeted genomic locus or loci and the second subset of nucleic acid-targeting complexes inactivate the first nucleic acid-targeting system, thereby inactivating further nucleic acid-targeting system expression in the cell.

Modification of the RNA-Guided Nucleases

In an embodiment, nucleic acid molecule(s) encoding the CRISPR enzymes disclosed herein, or an ortholog or homolog thereof, may be codon-optimized for expression in an eukaryotic cell. In some embodiments, the CRISPR enzymes disclosed herein, or an ortholog or homolog thereof, may be codon-optimized for expression in a plant cell. In some embodiments, a nucleic acid molecule may comprise one or more sequences selected from SEQ ID NOs: 300-799. Nucleic acid molecule(s) can be engineered or non-naturally occurring. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. The nucleic acid-targeting systems described herein are non-naturally occurring.

In some embodiments, the CRISPR enzymes disclosed herein, or an ortholog or homolog thereof, may comprise one or more mutations (and hence nucleic acid molecule(s) coding for same may have mutation(s)). The mutations may be artificially introduced mutations and may include but are not limited to one or more mutations in a catalytic domain. Examples of catalytic domains with reference to a Cas enzyme may include but are not limited to RuvC I, RuvC II, RuvC III and HNH domains.

In some embodiments, the CRISPR enzymes disclosed herein, or an ortholog or homolog thereof, may be used as a generic nucleic acid binding protein with fusion to or being operably linked to a functional domain. Examples of functional domains may include but are not limited to PvuII, MutH, TevI, FokI, AlwI, MlyI, SbfI, SdaI, StsI, CleDORF, Clo051, Pept071, recombinase, transposase, methylase, translational initiator, translational activator, translational repressor, nucleases, in particular ribonucleases, a spliceosome, beads, a light inducible/controllable domain or a chemically inducible/controllable domain. The FokI nuclease domain requires dimerization to cleave DNA and therefore CRISPR enzymes with FokI functional domains are needed to bind opposite DNA strands of the cleavage site.

In some embodiments, the unmodified CRISPR enzyme may have cleavage activity. In some embodiments, the CRISPR enzyme direct cleavage of one or both nucleic acid (DNA or RNA) strands at the location of or near a target sequence, such as within the target sequence and/or within the complement of the target sequence or at sequences associated with the target sequence. In some embodiments, the CRISPR enzyme may direct cleavage of one or both DNA or RNA strands within about 1, 2, 3, 4, 5, 6, 7, 8, 9, 10, 15, 20, 25, 50, 100, 200, 500, or more base pairs from the first or last nucleotide of a target sequence. In some embodiments, the cleavage may be staggered, i.e. generating sticky ends. In some embodiments, the cleavage is a staggered cut with a 5' overhang. In some embodiments, the cleavage is a staggered cut with a 5' overhang of 1 to 5 nucleotides, 4 or 5 nucleotides. In some embodiments, a vector encodes a CRISPR enzyme that may be mutated with respect to a corresponding wild-type enzyme such that the mutated CRISPR enzyme lacks the ability to cleave one or both DNA or RNA strands of a target polynucleotide containing a target sequence. As a further example, two or more catalytic domains of a CRISPR enzyme (e.g. RuvC I, RuvC II, and RuvC III or the HNH domain) may be mutated to produce a mutated CRISPR enzyme substantially lacking all DNA cleavage activity. In some embodiments, a CRISPR enzyme may be considered to substantially lack all RNA cleavage activity when the RNA cleavage activity of the mutated CRISPR enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated CRISPR enzyme is nil or negligible as compared with the non-mutated CRISPR enzyme. An CRISPR enzyme may be identified with reference to the general class of enzymes that share homology to the biggest nuclease with multiple nuclease domains from the CRISPR system.

In the context of a nucleic acid-targeting system, formation of a nucleic acid-targeting complex (comprising a guide RNA hybridized to a target sequence and complexed with one or more CRISPR enzymes as described herein) typically results in cleavage of one or both DNA or RNA strands in or near (e.g., within 1, 2, 3, 4, 5, 6, 7, 8, 9, 10, 20, 50, or more base pairs from) the target sequence. As used herein the term "sequence(s) associated with a target locus of interest" refers to sequences near the vicinity of the target sequence (e.g. within 1, 2, 3, 4, 5, 6, 7, 8, 9, 10, 20, 50, or more base pairs from the target sequence, wherein the target sequence is comprised within a target locus of interest).

Target Sequences

As used herein, the term "target polynucleotide" or "target sequence" refers to a nucleotide sequence that occurs in a polynucleotide against which a guide RNA is directed. In some embodiments, the target polynucleotide or target sequence is in a gene. In this context, the term "gene" means a locatable region of genomic sequence, corresponding to a unit of inheritance, which includes regulatory regions, such as promoters, enhancers, 5' untranslated regions, intron regions, 3' untranslated regions, transcribed regions, and other functional sequence regions that may exist as native genes or transgenes in a plant genome. Depending upon the circumstances, the term target sequence or target gene can refer to the full-length nucleotide sequence of the gene or gene product targeted for suppression or the nucleotide sequence of a portion of the gene or gene product targeted for suppression.

The target polynucleotide of a nucleic acid-targeting system as described herein can be any polynucleotide endogenous or exogenous to a prokaryotic or a eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA), or a combination of both.

Examples of target polynucleotides include a sequence associated with a signaling biochemical pathway, e.g., a signaling biochemical pathway-associated gene or polynucleotide. Examples of target polynucleotides include genes that encode proteins that provide tolerance to herbicides, such as 5-enolpyruvylshikimate-3-phosphate synthase (EPSPS), glyphosate oxidoreductase (GOX), glyphosate decarboxylase, glyphosate-N-acetyl transferase (GAT), dicamba monooxygenase, phosphinothricin acetyltransferase, 2,2-dichloropropionic acid dehalogenase, acetohydroxyacid synthase, acetolactate synthase (ALS), haloarylnitrilase, acetyl-coenzyme A carboxylase, dihydropteroate synthase, phytoene desaturase, Protoporphyrinogen oxidase (PPO), protoporphyrin IX oxygenase, hydroxyphenylpyruvate dioxygenase, para-aminobenzoate synthase, glutamine synthase, cellulose synthase, beta-tubulin, 4-Hydroxyphenylpyruvate dioxygenase (HPPD) and serine hydroxymethyltransferase. Examples of target polynucleotides include polynucleotides associated with a disease resistance locus. As used herein, the term "disease resistance locus" refers to a genomic region associated with disease or pathogen resistance in a plant. A disease resistance locus may comprise one or more genes, gene families, arrays of genes or QTLs encoding a protein or proteins that confer to a plant resistance to at least one disease or pathogen. In one embodiment, the disease resistance locus comprises one or more NBS-LRR disease resistance genes, also referred to as NB-LRR genes, R genes, LRR genes. In another embodiment, the disease resistance locus comprises one or more PRR disease resistance genes. The disease resistance locus may encompass a specific gene, cluster of genes, array of genes and/or gene family known to confer pathogen resistance, for example Rp1, or Rpp1, or Rps1. In another embodiment, the disease resistance locus comprises the Rgh1 locus. In another embodiment, the disease resistance locus comprises the Rgh4 locus. Alternatively, the disease resistance locus may encompass a genomic region but the actual gene/element composition conferring disease resistance is unknown. Examples of target polynucleotides include polynucleotides that encode quality traits, such as brown midrib (bmr), waxy, white, Fad2, Fad3.

Without wishing to be bound by theory, it is believed that the target sequence should be associated with a PAM (protospacer adjacent motif); that is, a short sequence recognized by the nucleic acid-targeting system. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. Further, engineering of the PAM Interacting (PI) domain may allow programming of PAM specificity, improve target site recognition fidelity, and increase the versatility of the CRISPR enzyme. CRISPR enzymes, such as Cas9 proteins, may be engineered to alter their PAM specificity, for example as described in Kleinstiver B P et al. Engineered CRISPR-Cas9 nucleases with altered PAM specificities. Nature. 2015 Jul. 23; 523 (7561): 481-5. doi: 10.1038/nature14592.

Uses of the RNA-Guided Nucleases and the Nucleic Acid-Targeting System

In an aspect, the disclosure provides a method for sequence-specific modification of a target nucleic acid sequence in a cell, comprising providing to a cell (a) a guide RNA specific for a target nucleic acid sequence in a cell, and (b) a CRISPR enzyme. In some embodiments, the guide RNA is provided by expressing in the cell a recombinant DNA molecule encoding the guide RNA, and/or the CRISPR enzyme is provided by expressing in the cell a recombinant DNA molecule encoding the CRISPR enzyme. In some embodiments, the guide RNA is provided by contacting the cell with a composition comprising the guide RNA or a recombinant DNA molecule encoding the guide RNA, and/or the CRISPR enzyme is provided by contacting the cell with a composition comprising the CRISPR enzyme or a recombinant DNA molecule encoding the CRISPR enzyme. In some embodiments, the guide RNA is complexed with the CRISPR enzyme and provided to the cell. Methods and compositions for providing RNAs to plant cells are known in the art. See, e.g., PCTUS2016035500, PCTUS2016035435, and WO2011112570, incorporated by reference herein.

In an aspect the disclosure provides a method as herein discussed wherein the host is a eukaryotic cell. In an aspect the disclosure provides a method as herein discussed wherein the host is a mammalian cell. In an aspect the disclosure provides a method as herein discussed, wherein the host is a non-human eukaryote cell. In an aspect the disclosure provides a method as herein discussed, wherein the non-human eukaryote cell is a non-human mammal cell. In an aspect the disclosure provides a method as herein discussed, wherein the non-human mammal cell may be including, but not limited to, primate bovine, ovine, procine, canine, rodent, Leporidae such as monkey, cow, sheep, pig, dog, rabbit, rat or mouse cell. In an aspect the disclosure provides a method as herein discussed, the cell may be a non-mammalian eukaryotic cell such as poultry bird (e.g., chicken), vertebrate fish (e.g., salmon) or shellfish (e.g., oyster, claim, lobster, shrimp) cell. In an aspect the disclosure provides a method as herein discussed, the non-human eukaryote cell is a plant cell. The plant cell may be of a monocot or dicot or of a crop or grain plant such as cassava, corn, sorghum, alfalfa, cotton, soybean, canola, wheat, oat or rice. The plant cell may also be of an algae, tree or production plant, fruit or vegetable (e.g., trees such as citrus trees, e.g., orange, grapefruit or lemon trees; peach or nectarine trees; apple or pear trees; nut trees such as almond or walnut or pistachio trees; nightshade plants; plants of the genus *Brassica*; plants of the genus *Lactuca*; plants of the genus *Spinacia*; plants of the genus *Capsicum*; cotton, tobacco, asparagus, avocado, papaya, cassava, carrot, cabbage, broccoli, cauliflower, tomato, eggplant, pepper, lettuce, spinach, strawberry, potato, squash, melon, blueberry, raspberry, blackberry, grape, coffee, cocoa, etc).

In another aspect, the present disclosure provides for a method of functional screening of genes in a genome in a pool of cells ex vivo or in vivo comprising the administration or expression of a library comprising a plurality of guide RNAs and wherein the screening further comprises use of a CRISPR enzyme as described herein. In some embodiments, the nucleic acid-targeting system is modified to comprise a heterologous functional domain. In an aspect the disclosure provides a method for screening a genome comprising the administration to a host or expression in a host in vivo of a library. In an aspect the disclosure provides a method as herein discussed further comprising an activator administered to the host or expressed in the host. In an aspect the disclosure provides a method as herein discussed wherein the activator is attached to a CRISPR enzyme as described herein. In an aspect the disclosure provides a method as herein discussed wherein the activator is attached to the N terminus or the C terminus of the CRISPR enzyme. In an aspect the disclosure provides a method as herein discussed wherein the activator is attached to a gRNA loop. In an aspect the disclosure provides a method as herein discussed further comprising a repressor administered to the host or expressed in the host. In an aspect the disclosure provides a method as herein discussed wherein the screening comprises affecting and detecting gene activation, gene inhibition, or cleavage in the locus.

In an aspect, the disclosure provides efficient on-target activity and minimizes off target activity. In an aspect, the disclosure provides efficient on-target cleavage by a CRISPR enzyme as described herein and minimizes off-target cleavage by the CRISPR enzyme. In an aspect, the disclosure provides guide RNA specific binding of a CRISPR enzyme at a gene locus without DNA cleavage. In an aspect, the disclosure provides efficient guide RNA directed on-target binding of a CRISPR enzyme at a genomic locus and minimizes off-target binding of the CRISPR enzyme. Accordingly, in an aspect, the disclosure provides target-specific gene regulation. In an aspect, the disclosure provides guide RNA specific binding of a CRISPR enzyme at a genomic locus without DNA cleavage. Accordingly, in an aspect, the disclosure provides for cleavage at one genomic locus and gene regulation at a different genomic locus using a single CRISPR enzyme. In an aspect, the disclosure provides orthogonal activation and/or inhibition and/or cleavage of multiple targets using one or more CRISPR enzymes.

In an aspect the disclosure provides a method as herein discussed comprising the delivery of the nucleic acid-targeting complexes or component(s) thereof or nucleic acid molecule(s) coding therefor, wherein said nucleic acid molecule(s) are operatively linked to regulatory sequence(s) and expressed in vivo. In an aspect the disclosure provides a method as herein discussed wherein the expressing in vivo is via a lentivirus, an adenovirus, an AAV, a geminivirus, a Tobacco Rattle Virus (TRV), Potato virus X (PVX), Tomato yellow leaf curl China virus (TYLCCV), a Begomovirus, Barley stripe mosaic virus (BSMV), Cymbidium mosaic virus (CymMV), Rice tungro bacilliform virus (RTBV), Cauliflower mosaic virus (CaMV), Turnip yellow mosaic virus (TYMV), Cabbage leaf curl virus (CbLCV), Apple latent spherical virus (ALSV), Cucumber mosaic virus (CMV), Cotton leaf crumple virus (CLCrV), African cassava mosaic virus (ACMV), Pea early browning virus (PEBV), Beet curly top virus (BCTV) or an *Agrobacterium*. In an aspect the disclosure provides a method as herein discussed wherein the delivery of one or more components of the nucleic acid-targeting system is via a particle, a nanoparticle, a lipid or a cell penetrating peptide (CPP).

In an aspect, the disclosure provides a pair of nucleic acid-targeting systems (e.g., a pair of CRISPR-Cas complexes), each comprising a guide RNA (gRNA) comprising a guide sequence capable of hybridizing to a target sequence in a genomic locus of interest in a cell, wherein at least one loop of each gRNA is modified by the insertion of distinct RNA sequence(s) that bind to one or more adaptor proteins, and wherein the adaptor protein is associated with one or more functional domains, wherein each gRNA of each CRISPR-Cas comprises a functional domain having a DNA cleavage activity.

In an aspect, the disclosure provides a method for cutting a target sequence in a genomic locus of interest comprising delivery to a cell of the nucleic acid-targeting complexes or component(s) thereof or nucleic acid molecule(s) coding therefor, wherein said nucleic acid molecule(s) are operatively linked to regulatory sequence(s) and expressed in vivo. In an aspect the disclosure provides a method as herein-discussed wherein the delivery is via a lentivirus, an adenovirus, an AAV, a geminivirus, a Tobacco Rattle Virus (TRV), Potato virus X (PVX), Tomato yellow leaf curl China virus (TYLCCV), a Begomovirus, Barley stripe mosaic virus (BSMV), Cymbidium mosaic virus (CymMV), Rice tungro bacilliform virus (RTBV), Cauliflower mosaic virus (CaMV), Turnip yellow mosaic virus (TYMV), Cabbage leaf curl virus (CbLCV), Apple latent spherical virus (ALSV), Cucumber mosaic virus (CMV), Cotton leaf crumple virus (CLCrV), African cassava mosaic virus (ACMV), Pea early browning virus (PEBV), Beet curly top virus (BCTV) or an *Agrobacterium*. In an aspect the disclosure provides a method as herein-discussed or paired nucleic acid-targeting complexes as herein-discussed where the target sequence for a first complex of the pair is on a first strand of double stranded DNA and the target sequence for a second complex of the pair is on a second strand of double stranded DNA. In an aspect the disclosure provides a method as herein-discussed or paired nucleic acid-targeting complexes as herein-discussed wherein the target sequences of the first and second complexes are in proximity to each other such that the DNA is cut in a manner that facilitates homology directed repair. In an aspect a herein method can further include introducing into the cell template DNA. In an aspect a herein method or herein paired nucleic acid-targeting complexes can be used wherein each nucleic acid-targeting complex has an RNA-guided nuclease that is mutated such that it has no more than about 5% of the nuclease activity of the RNA-guided nuclease that is not mutated.

In one aspect, the disclosure provides a method for altering or modifying expression of a gene product. The method may comprise introducing into a cell containing and expressing a DNA molecule encoding the gene product an engineered, non-naturally occurring nucleic acid-targeting system comprising a CRISPR enzyme and a guide RNA that targets the DNA molecule, whereby the guide RNA targets the DNA molecule encoding the gene product and the CRISPR enzyme cleaves the DNA molecule encoding the gene product, whereby expression of the gene product is altered; and, where the CRISPR enzyme and the guide RNA do not naturally occur together. The disclosure further comprehends the CRISPR enzyme being codon optimized for expression in a Eukaryotic cell. In an embodiment the eukaryotic cell is a plant cell. In a further embodiment of the disclosure, the expression of the gene product is decreased.

In an aspect, the disclosure provides altered cells and progeny of those cells, as well as products made by the cells. CRISPR enzymes and nucleic acid-targeting systems of the disclosure are used to produce cells comprising a modified target locus. In some embodiments, the method may comprise allowing a nucleic acid-targeting complex to bind to the target DNA or RNA to effect cleavage of said target DNA or RNA thereby modifying the target DNA or RNA, wherein the nucleic acid-targeting complex comprises a CRISPR enzyme complexed with a guide RNA hybridized to a target sequence within said target DNA or RNA. In one aspect, the disclosure provides a method of repairing a genetic locus in a cell. In another aspect, the disclosure provides a method of modifying expression of DNA or RNA in a eukaryotic cell. In some embodiments, the method comprises allowing a nucleic acid-targeting complex to bind to the DNA or RNA such that said binding results in increased or decreased expression of said DNA or RNA; wherein the nucleic acid-targeting complex comprises a CRISPR enzyme complexed with a guide RNA. Similar considerations and conditions apply as above for methods of modifying a target DNA or RNA. In fact, these sampling, culturing and re-introduction options apply across the aspects of the present disclosure. In an aspect, the disclosure provides for methods of modifying a target DNA or RNA in a eukaryotic cell, which may be in vivo, ex vivo or in vitro. In some embodiments, the method comprises sampling a cell or population of cells from a plant, and modifying the cell or cells. Culturing may occur at any stage ex vivo. Such cells can be, without limitation, plant cells, animal cells, yeast cells, particular cell types of any organism, including protoplasts, somatic cells, germ cells, haploid cells, stem cells, immune cells, T cell, B cells, dendritic cells, cardiovascular cells, epithelial cells, stem cells and the like. The cells can be modified according to the disclosure to produce gene products, for example in controlled amounts, which may be increased or decreased, depending on use, and/or mutated. In certain embodiments, a genetic locus of the cell is repaired. The cell or cells may even be re-introduced into the non-human animal or plant. For re-introduced cells it may be preferred that the cells are stem cells.

In an aspect, the instant disclosure provides cells which transiently comprise the nucleic acid-targeting systems, or components thereof. For example, CRISPR enzymes and guide RNAs are transiently provided to a cell and a genetic locus is altered, followed by a decline in the amount of one or more components of the nucleic acid-targeting system. Subsequently, the cells, progeny of the cells, and organisms which comprise the cells, having acquired a RNA-guided nuclease mediated genetic alteration, comprise a diminished amount of one or more nucleic acid-targeting system components, or no longer contain the one or more nucleic acid-targeting system components. One non-limiting example is a self-inactivating CRISPR-Cas system such as further described herein. Thus, the disclosure provides cells, and organisms, and progeny of the cells and organisms which comprise one or more nucleic acid-targeting system-altered genetic loci, but essentially lack one or more nucleic acid-targeting system components. In certain embodiments, the nucleic acid-targeting system components are substantially absent. Such cells, tissues and organisms advantageously comprise a desired or selected genetic alteration but have lost nucleic acid-targeting components or remnants thereof that potentially might act non-specifically, lead to questions of safety, or hinder regulatory approval. As well, the disclosure provides products made by the cells, organisms, and progeny of the cells and organisms.

Gene Editing or Altering a Target Loci

In some embodiments, a double strand break or single strand break in one of the strands is sufficiently close to target position such that template repair occurs. In an embodiment, the distance is not more than 10, 20, 50, 100, 150, 200, 250, 300, 350 or 400 nucleotides. While not wishing to be bound by a particular theory, it is believed that the break should be sufficiently close to target position such that the break is within the region that is subject to exonuclease-mediated removal during end resection. If the distance between the target position and a break is too great, the mutation may not be included in the end resection and, therefore, may not be corrected, as the template nucleic acid sequence may only be used to repair sequence within the end resection region.

In an embodiment, in which a guide RNA and CRISPR enzyme, in particular a CRISPR enzyme comprises an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87 or an ortholog or homolog thereof, induces a double strand break for the purpose of inducing HDR-mediated repair, the cleavage site is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position. In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position. In a further embodiment, two or more guide RNAs complexing with a CRISPR enzyme or an ortholog or homolog thereof, may be used to induce multiplexed breaks for purpose of inducing HDR-mediated repair.

In some embodiments, homology arm extend at least as far as the region in which end resection may occur, e.g., in order to allow the resected single stranded overhang to find a complementary region within the donor template. In some embodiments, the overall length is limited by parameters such as plasmid size or viral packaging limits. In an embodiment, a homology arm does not extend into repeated elements. Examples of homology arm lengths include a least 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 1000 nucleotides.

Target position, as used herein, refers to a site on a target nucleic acid or target gene (e.g., the chromosome) that is modified by an RNA-guided nuclease, in particular a CRISPR enzyme comprises an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87 or an ortholog or homolog thereof, preferably guide RNA-dependent process. For example, the target position can be a modified CRISPR enzyme cleavage of the target nucleic acid and template nucleic acid directed modification, e.g., repair, of the target position. In an embodiment, a target position can be a site between two nucleotides, e.g., adjacent nucleotides, on the target nucleic acid into which one or more nucleotides is added. In some embodiments, the target position may comprise one or more nucleotides that are altered, e.g., repaired, by a template nucleic acid. In an embodiment, the target position is within a target sequence (e.g., the sequence to which the guide RNA binds). In an embodiment, a target position is upstream or downstream of a target sequence (e.g., the sequence to which the guide RNA binds).

Nucleic Acid Targeting System Promoted Non-Homologous End-Joining

In certain embodiments, nuclease-induced non-homologous end-joining (NHEJ) can be used to target gene-specific knockouts. Nuclease-induced NHEJ can also be used to remove (e.g., delete) sequence in a gene of interest. Generally, NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein. The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily be greater than 50 bp, e.g., they can easily reach greater than about 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it may also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving and single strand cleaning RNA-guided nuclease, or an ortholog or homolog thereof, can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

In an embodiment, in which a guide RNA and a CRISPR enzyme, or an ortholog or homolog thereof generate a double strand break for the purpose of inducing NHEJ-mediated indels, a guide RNA may be configured to position one double-strand break in close proximity to a nucleotide of the target position. In an embodiment, the cleavage site may be between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two guide RNAs complexing with CRISPR enzymes, or an ortholog or homolog thereof, preferably nickases induce two single strand breaks for the purpose of inducing NHEJ-mediated indels, two guide RNAs may be configured to position two single-strand breaks to provide for NHEJ repair a nucleotide of the target position.

Nucleic Acid Targeting Systems can Deliver Functional Effectors

Unlike Nucleic Acid Targeting System-mediated gene knockout, which permanently eliminates expression by mutating the gene at the DNA level, Nucleic Acid Targetting System-mediated knockdown allows for temporary reduction of gene expression through the use of artificial transcription factors. Mutating key residues in both DNA cleavage domains of the CRISPR enzyme results in the generation of a catalytically inactive CRISPR enzyme. A catalytically inactive CRISPR enzyme complexes with a guide RNA and localizes to the DNA sequence specified by that guide RNA's targeting domain, however, it does not cleave the target DNA. Fusion of the inactive CRISPR enzyme to an effector domain, (e.g., a transcription repression domain, a transcription activation domain, a methylase, a transposase, a recombinase, a gyrase, a helicase) enables recruitment of the effector to any DNA site specified by the guide RNA. In certain embodiments, the inactive CRISPR enzyme may be fused to a transcriptional repression domain and recruited to the promoter region of a gene. In some embodiments, it is contemplated herein that blocking the binding site of an endogenous transcription factor would aid in downregulating gene expression. In another embodiment, an inactive CRISPR enzyme can be fused to a chromatin modifying protein. Altering chromatin status can result in decreased expression of the target gene.

In an aspect the disclosure provides a pair of complexes comprising a CRISPR enzyme and a guide RNA (gRNA) comprising a guide sequence capable of hybridizing to a target sequence in a genomic locus of interest in a cell, wherein each CRISPR enzyme comprises a heterologous functional domain. In some embodiments, the heterologous functional domain has DNA cleavage activity. In an aspect the disclosure provides paired complexes as herein-discussed, wherein the DNA cleavage activity is due to a Fok1 nuclease.

In some embodiments, the one or more functional domains is attached to the CRISPR enzyme so that upon binding to the sgRNA and target the functional domain is in a spatial orientation allowing for the functional domain to function. In some embodiments, the one or more functional domains is attached to the adaptor protein so that upon binding of the CRISPR enzyme to the gRNA and target, the functional domain is in a spatial orientation allowing for the functional domain to function. In an aspect the disclosure provides a composition as herein discussed wherein the one or more functional domains is attached to the CRISPR enzyme or adaptor protein via a linker, optionally a GlySer linker, as discussed herein. In some embodiments, the CRISPR enzyme is catalytically inactive. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease. In some preferred embodiments, the functional domain is a transcriptional activation domain, such as, without limitation, VP64, p65, MyoD1, HSF1, RTA, SET7/9 or a histone acetyltransferase. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain. In some embodiments, the one or more functional domains is an NLS (Nuclear Localization Sequence) or an NES (Nuclear Export Signal). In some embodiments, the one or more functional domains is a transcriptional activation domain comprises VP64, p65, MyoD1, HSF1, RTA, SET7/9 and a histone acetyltransferase. Other references herein to activation (or activator) domains in respect of those associated with the CRISPR enzyme include any known transcriptional activation domain and specifically VP64, p65, MyoD1, HSF1, RTA, SET7/9 or a histone acetyltransferase. In some embodiments, the one or more functional domains is a transcriptional repressor domain. In some embodiments, the transcriptional repressor domain is a KRAB domain. In some embodiments, the transcriptional repressor domain is a NuE domain, NcoR domain, SID domain or a SID4X domain. In some embodiments, the one or more functional domains have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity. In some embodiments, the one or more functional domains are histone modifying domains. Examples of histone modifying domains include transposase domains, HR (Homologous Recombination) machinery domains, recombinase domains, and/or integrase domains. In some embodiments, DNA integration activity includes HR machinery domains, integrase domains, recombinase domains and/or transposase domains. Histone acetyltransferases are preferred in some embodiments.

In an embodiment, a guide RNA molecule can be targeted to a known transcription response elements (e.g., promoters, enhancers, etc.), a known upstream activating sequences, and/or sequences of unknown or known function that are suspected of being able to control expression of the target DNA.

In some methods, a target polynucleotide can be inactivated to effect the modification of the expression in a cell. For example, upon the binding of a complex of nucleic acid-targeting system components to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

Genome Wide Knock-Out Screening

The CRISPR enzymes and nucleic acid-targeting systems described herein can be used to perform functional genomic screens. Such screens can utilize guide RNA based genome wide libraries. Such screens and libraries can provide for determining the function of genes, cellular pathways genes are involved in, and how any alteration in gene expression can result in a particular biological process. An advantage of the present disclosure is that the CRISPR system avoids off-target binding and its resulting side effects. This is achieved using systems arranged to have a high degree of sequence specificity for the target DNA. In some embodiments, the CRISPR enzymes comprise an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87 or an ortholog or homolog thereof.

In some embodiments, a genome wide library may comprise a plurality of guide RNAs, as described herein, comprising guide sequences that are capable of targeting a plurality of target sequences in a plurality of genomic loci in a population of eukaryotic cells. The population of cells may be a population of plant cells. The target sequence in the genomic locus may be a non-coding sequence. The non-coding sequence may be an intron, regulatory sequence, splice site, 3' UTR, 5' UTR, or polyadenylation signal. Gene function of one or more gene products may be altered by said targeting. The targeting may result in a knockout of gene function. The targeting of a gene product may comprise more than one guide RNA. A gene product may be targeted by 2, 3, 4, 5, 6, 7, 8, 9, or 10 guide RNAs. Off-target modifications may be minimized by exploiting the staggered double strand breaks generated by Cas effector protein complexes or by utilizing methods analogous to those used in CRISPR-Cas9 systems (See, e.g., DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013)), incorporated herein by reference. The targeting may be of about 100 or more sequences. The targeting may be of about 1000 or more sequences. The targeting may be of about 20,000 or more sequences. The targeting may be of the entire genome. The targeting may be of a panel of target sequences focused on a relevant or desirable pathway. The pathway may be an immune pathway. The pathway may be a cell division pathway.

One aspect of the disclosure comprehends a genome wide library that may comprise a plurality of guide RNAs that may comprise guide sequences that are capable of targeting a plurality of target sequences in a plurality of genomic loci, wherein said targeting results in a knockout of gene function. This library may potentially comprise guide RNAs that target each and every gene in the genome of an organism. In some embodiments, the organism is a plant.

In some embodiments of the disclosure the organism is a eukaryote (including mammal including human) or a non-human eukaryote or a non-human animal or a non-human mammal. In some embodiments, the organism is a non-human animal, and may be an arthropod, for example, an insect, or may be a nematode. In some methods of the disclosure the organism is a plant. In some methods of the disclosure the organism or subject is algae, including microalgae, or is a fungus.

The knockout of gene function may comprise: introducing into each cell in the population of cells a vector system of one or more vectors comprising an engineered, non-naturally occurring nucleic acid-targeting system comprising I). a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87, and II). one or more guide RNAs, wherein components I and II may be same or on different vectors of the system, integrating components I and II into each cell, wherein the guide sequence targets a unique gene in each cell, wherein the CRISPR enzyme is operably linked to a regulatory element, wherein when transcribed, the guide RNA comprising the guide sequence directs sequence-specific binding of the nucleic acid-targeting system to a target sequence in the genomic loci of the unique gene, inducing cleavage of the genomic loci by the CRISPR enzyme, and confirming different knockout mutations in a plurality of unique genes in each cell of the population of cells thereby generating a gene knockout cell library. The disclosure comprehends that the population of cells is a population of eukaryotic cells, and in a preferred embodiment, the population of cells is a population of plant cells.

The one or more vectors may be plasmid vectors. The vector may be a single vector comprising a CRISPR enzyme, a gRNA, and optionally, a selection marker into target cells. Not being bound by a particular theory, the ability to simultaneously deliver a CRISPR enzyme and gRNA through a single vector enables application to any cell type of interest, without the need to first generate cell lines that express the CRISPR enzyme. In some embodiments, it is desirable to a generate cell lines that expresses one or more CRISPR enzymes to which one or more guide RNAS are delivered. The regulatory element may be an inducible promoter. The inducible promoter may be a doxycycline inducible promoter. In some methods of the disclosure the expression of the guide sequence is under the control of the T7 promoter and is driven by the expression of T7 polymerase. The confirming of different knockout mutations may be by whole exome sequencing. The knockout mutation may be achieved in 100 or more unique genes. The knockout mutation may be achieved in 1,000 or more unique genes. The knockout mutation may be achieved in 20,000 or more unique genes. The knockout of gene function may be achieved in a plurality of unique genes which function in a particular physiological pathway or condition. The pathway or condition may be an herbicide tolerance pathway.

The disclosure also provides kits that comprise the genome wide libraries mentioned herein. The kit may comprise a single container comprising vectors or plasmids comprising the library of the disclosure. The kit may also comprise a panel comprising a selection of unique guide RNAs comprising guide sequences from the library of the disclosure, wherein the selection is indicative of a particular physiological condition, such as abiotic stress. The disclosure comprehends that the targeting is of about 100 or more sequences, about 1000 or more sequences or about 20,000 or more sequences or the entire genome. Furthermore, a panel of target sequences may be focused on a relevant or desirable pathway, such as herbicide tolerance.

Functional Alteration and Screening

In another aspect, the present disclosure provides for a method of functional evaluation and screening of genes. The use of the CRISPR enzymes of the present disclosure to precisely deliver functional domains, to activate or repress genes or to alter epigenetic state by precisely altering the methylation site on a specific locus of interest, can be with one or more guide RNAs applied to a single cell or population of cells or with a library applied to genome in a pool of cells ex vivo or in vivo comprising the administration or expression of a library comprising a plurality of guide RNAs (gRNAs) and wherein the screening further comprises use of a CRISPR enzyme comprising an amino acid sequence having at least 85%, at least 90%, at least 91%, at least 92%, at least 93%, at least 94%, at least 95%, at least 96%, at least 97%, at least 98%, at least 99%, or 100% homology to a sequence selected from the group consisting of SEQ ID NOs: 73, and 75-87, wherein the CRISPR enzyme is modified to comprise a heterologous functional domain. In an aspect the disclosure provides a method as herein discussed further comprising an activator administered to the host or expressed in the host. In an aspect the disclosure provides a method as herein discussed wherein the activator is attached to a CRISPR enzyme. In an aspect the disclosure provides a method as herein discussed wherein the activator is attached to the N terminus or the C terminus of the CRISPR enzyme. In an aspect the disclosure provides a method as herein discussed, wherein the screening comprises affecting and detecting gene activation, gene inhibition, or cleavage in the locus.

In an aspect the disclosure provides a method as herein discussed, wherein the host is a eukaryotic cell. In an aspect the disclosure provides a method as herein discussed, wherein the host is a mammalian cell. In an aspect the disclosure provides a method as herein discussed, wherein the host is a non-human eukaryote. In an aspect the disclosure provides a method as herein discussed, wherein the non-human eukaryote is a plant.

Method of Using Nucleic Acid Targeting Systems to Modify a Cell or Organism

The disclosure in some embodiments comprehends a method of modifying an cell or organism. The cell may be a prokaryotic cell or a eukaryotic cell. The cell may be a mammalian cell. The mammalian cell many be a non-human primate, bovine, porcine, rodent or mouse cell. The cell may be a non-mammalian eukaryotic cell such as poultry, fish or shrimp. The cell may also be a plant cell. The plant cell may be of a crop plant such as cassava, soybean, corn, cotton, alfalfa, canola, sorghum, wheat, or rice. The plant cell may also be of an algae, tree or vegetable. The modification introduced to the cell by the present disclosure may be such that the cell and progeny of the cell are altered for improved production of biologic products such as an antibody, oil, fiber, starch, alcohol or other desired cellular output. The modification introduced to the cell by the present disclosure may be such that the cell and progeny of the cell include an alteration that changes the biologic product produced.

The nucleic acid-targeting system may comprise one or more different vectors. In an aspect of the disclosure, the CRISPR enzyme is codon optimized for expression the desired cell type, preferentially a eukaryotic cell, preferably a plant cell.

Delivery of the Nucleic Acid-Targeting System and Components Thereof

Through this disclosure and the knowledge in the art, nucleic acid-targeting system, specifically the novel systems described herein, or components thereof or nucleic acid molecules thereof (including, for instance HDR template) or nucleic acid molecules encoding or providing components thereof may be delivered by a delivery system herein described both generally and in detail.

The CRISPR enzymes, for instance those encoded by a polynucleotide sequence selected from SEQ ID NOs: 37-72, 74, 88-100 and 300-799, and/or any of the present RNAs, for instance a guide RNA, can be delivered using any suitable vector, e.g., plasmid or viral vectors, such as Ti plasmids of *Agrobacterium tumefaciens*, geminivirus, Tobacco Rattle Virus (TRV), Potato virus X (PVX), Tomato yellow leaf curl China virus (TYLCCV), Begomovirus, Barley stripe mosaic virus (BSMV), Cymbidium mosaic virus (CymMV), Rice tungro bacilliform virus (RTBV), Cauliflower mosaic virus (CaMV), Turnip yellow mosaic virus (TYMV), Cabbage leaf curl virus (CbLCV), Apple latent spherical virus (ALSV), Cucumber mosaic virus (CMV), Cotton leaf crumple virus (CLCrV), African cassava mosaic virus (ACMV), Pea early browning virus (PEBV), Beet curly top virus (BCTV), adeno associated virus (AAV), lentivirus, adenovirus or other viral vector types, or combinations thereof. The CRISPR enzymes and one or more guide RNAs can be packaged into one or more vectors, e.g., plasmid or viral vectors. In some embodiments, the vector, e.g., plasmid or viral vector, is delivered to the tissue of interest by, for example, particle bombardment, *Agrobacterium* infection, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 µg to about 10 µg. Plasmids of the disclosure will generally comprise one or more of (i) a promoter; (ii) a sequence encoding CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

In some embodiments the RNA molecules of the disclosure are delivered in liposome or lipofectin formulations and the like and can be prepared by methods well known to those skilled in the art. Such methods are described, for example, in U.S. Pat. Nos. 5,593,972, 5,589,466, 5,580,859, and 9,121,022 which are herein incorporated by reference. Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present disclosure.

In some embodiments, RNA delivery is in vivo delivery. It is possible to deliver CRISPR enzyme and gRNA (and, for instance, HR repair template (e.g., an HR repait template comprising one or more transgenes)) into cells using liposomes or nanoparticles. Thus delivery of the CRISPR enzyme and/or delivery of the RNAs of the disclosure may be in RNA form and via microvesicles, liposomes or particle or particles. For example, mRNA encoding a CRISPR enzyme and gRNA can be packaged into liposomal particles for delivery in vivo. Liposomal transfection reagents such as lipofectamine from Life Technologies and other reagents on the market can effectively deliver RNA molecules into the liver. In some embodiments, encoding a CRISPR enzyme and gRNA can be as described in U.S. Pat. No. 9,121,022, PCTUS2016035500, and PCTUS2016035435, which are herein incorporated by reference herein.

Means of delivery of RNA also include delivery of RNA via particles or particles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo.

Several embodiments relate to enhancing NHEJ or HR efficiency. NHEJ efficiency can be enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Particle Delivery Systems and/or Formulations

Several types of particle delivery systems and/or formulations are known to be useful in a diverse spectrum of applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present disclosure. A particle in accordance with the present disclosure is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the disclosure. In some embodiments, inventive particles have a greatest dimension ranging between 25 nm and 200 nm.

Particles delivery systems within the scope of the present disclosure may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present disclosure.

The disclosure involves at least one component of the nucleic acid-targeting system complex, e.g., CRISPR enzyme, gRNA, delivered via at least one nanoparticle complex. In some aspects, the disclosure provides methods comprising delivering one or more polynucleotides, such as or one or more vectors as described herein, one or more transcripts thereof, and/or one or proteins transcribed therefrom, to a host cell. In some aspects, the disclosure further provides cells produced by such methods, and plants comprising or produced from such cells. In some embodiments, a CRISPR enzyme in combination with (and optionally complexed with) a guide RNA is delivered to a cell. Conventional viral and non-viral based gene transfer methods can be used to introduce nucleic acids in plant cells or target tissues. Such methods can be used to administer nucleic acids encoding components of a nucleic acid-targeting system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat.

Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to whole plants or they can be administered to cells in vitro. Examples of viral based systems include geminivirus, a Tobacco Rattle Virus (TRV), Potato virus X (PVX), Tomato yellow leaf curl China virus (TYLCCV), a Begomovirus, Barley stripe mosaic virus (BSMV), Cymbidium mosaic virus (CymMV), Rice tungro bacilliform virus (RTBV), Cauliflower mosaic virus (CaMV), Turnip yellow mosaic virus (TYMV), Cabbage leaf curl virus (CbLCV), Apple latent spherical virus (ALSV), Cucumber mosaic virus (CMV), Cotton leaf crumple virus (CLCrV), African cassava mosaic virus (ACMV), Pea early browning virus (PEBV), Beet curly top virus (BCTV) for gene transfer.

In some embodiments, a host cell is transiently or non-transiently transfected with one or more vectors described herein. In some embodiments, a cell is transfected as it naturally occurs in a plant. In some embodiments, a cell that is transfected is taken from a plant. In some embodiments, the cell is derived from cells taken from a plant, such as a protoplast. In some embodiments, a cell transfected with one or more vectors described herein is used to establish a new cell line comprising one or more vector-derived sequences. In some embodiments, a cell transiently transfected with the components of a nucleic acid-targeting system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or plants derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. Methods for producing transgenic animals and plants are known in the art, and generally begin with a method of cell transfection, such as described herein. In one aspect, the disclosure provides for methods of modifying a target polynucleotide in a eukaryotic cell. In some embodiments, the method comprises allowing a nucleic acid-targeting complex to bind to the target polynucleotide to effect cleavage of said target polynucleotide thereby modifying the target polynucleotide, wherein the nucleic acid-targeting complex comprises a CRISPR enzyme complexed with a guide RNA hybridized to a target sequence within said target polynucleotide.

In one aspect, the disclosure provides a method of modifying expression of a polynucleotide in a eukaryotic cell. In some embodiments, the method comprises allowing a nucleic acid-targeting complex to bind to the polynucleotide such that said binding results in increased or decreased expression of said polynucleotide; wherein the nucleic acid-targeting complex comprises a CRISPR enzyme complexed with a guide RNA hybridized to a target sequence within said polynucleotide.

Use of Nucleic Acid-Targeting System in Plants

The nucleic acid-targeting systems (e.g., single or multiplexed) disclosed herein can be used in conjunction with recent advances in crop genomics. The systems described herein can be used to perform efficient and cost effective plant gene or genome interrogation or editing or manipulation. The nucleic acid-targeting systems can be used with regard to plants in Site-Directed Integration (SDI) or Gene Editing (GE) or any near reverse breeding or reverse breeding techniques. Aspects of utilizing the herein described nucleic acid-targeting systems may be analogous to the use of the CRISPR-Cas (e.g. CRISPR-Cas9) system in plants, and mention is made of the University of Arizona web site "CRISPR-PLANT" (http://www.genome.arizona.edu/crispr/) (supported by Penn State and AGI).

The methods for genome editing using the nucleic acid-targeting system as described herein can be used to confer desired traits on essentially any plant. A wide variety of plants and plant cell systems may be engineered for the desired physiological and agronomic characteristics described herein using the nucleic acid constructs of the present disclosure and the various transformation methods mentioned above.

In some embodiments, the polynucleotides encoding the components of the nucleic acid-targeting system are introduced for stable integration into the genome of a plant cell. In these embodiments, the design of the transformation vector or the expression system can be adjusted depending on for when, where and under what conditions the guide RNA and/or the CRISPR enzyme gene are expressed.

In some embodiments, the polynucleotides encoding the components of the nucleic acid-targeting system are transiently expressed in a plant, plant tissue, or plant cell. In these embodiments, the nucleic acid-targeting system can ensure modification of a target gene only when both the guide RNA and the CRISPR enzyme are present in a cell, such that genomic modification can further be controlled. As the expression of the CRISPR enzyme and guide RNA is transient, plants regenerated from such plant cells typically contain no foreign DNA. In particular embodiments the CRISPR enzyme is stably expressed by the plant cell and the guide RNA is transiently expressed. In particular embodiments the CRISPR enzyme is stably expressed by the plant cell and the guide RNA is provided directly to the plant cell by any method described herein.

DNA construct(s) containing the components of the nucleic acid-targeting system, and, where applicable, template sequence, may be introduced into the genome of a plant, plant part, or plant cell by a variety of conventional techniques.

In particular embodiments, the nucleic acid-targeting system components can be introduced in the plant cells using a plant viral vector. In some embodiments, the viral vector is a vector from a DNA virus. For example, geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., Faba bean necrotic yellow virus). In some embodiments, the viral vector is a vector from an RNA virus. For example, tobravirus (e.g., tobacco rattle virus, tobacco mosaic virus), potexvirus (e.g., potato virus X), or hordeivirus (e.g., barley stripe mosaic virus). The replicating genomes of plant viruses are non-integrative vectors.

The methods described herein generally result in the generation of plants comprising one or more desirable traits compared to the wildtype plant. In some embodiments, the plants, plant cells or plant parts obtained are transgenic plants, comprising an exogenous DNA sequence incorporated into the genome of all or part of the cells of the plant. In other embodiments, non-transgenic genetically modified plants, plant parts or cells are obtained, in that no exogenous DNA sequence is incorporated into the genome of any of the plant cells of the plant. In such embodiments, the plants are non-transgenic. Where only the modification of an endogenous gene is ensured and no foreign genes are introduced or maintained in the plant genome; the resulting genetically modified plants contain no non-native genes.

In some embodiments the nucleic acid-targeting system is targeted to a chloroplast. In some embodiments, targeting may be achieved by the presence of an N-terminal extension, called a chloroplast transit peptide (CTP) or plastid transit peptide.

EXAMPLES

Example 1: Identification of RNA-Guided DNA Nucleases

A number of RNA-guided DNA nucleases were identified based on their close proximity to a CRISPR (repeat element) locus. Polynucleotide sequences encoding RNA-guided DNA nucleases were identified by iterative bioinformatic searching of bacterial genomes from *Lysinibacillus* sp., *Brevibacillus* sp., *Sphingobium* sp., *Undibacterium* sp., *Bacillus* sp., *Chryseobacterium* sp., *Sphingomonas* sp., *Labrys* sp., *Brevibacillus laterosporus, Bacillus thuringiensis, Enterococcus faecalis, Brevibacillus brevis, Undibacterium pigrum, Novosphingobium rosa, Labrys methylaminiphilus*, and *Brevibacillus parabrevis*.

A search of 15,980 bacterial genomes for CRISPR sequences using the CRISPR recognition toolv1.1 was completed (Bland C, et al. CRISPR Recognition Tool (CRT): a tool for automatic detection of clustered regularly interspaced palindromic repeats. BMC Bioinformatics. 2007 Jun. 18; 8(1):209; web address: room220.com/crt). From this search, 20,468 CRISPR loci were identified in 8,865 genomes, of which 1,258 CRISPR loci were classified as Type II repeats (Chylinski, K. et al. The tracrRNA and Cas9 families of type II CRISPR-Cas immunity systems. RNA Biology 10:5, 726-737; 2013). Then, a non-redundant bacterial protein dataset was searched using pfam models (158 models from version 28.0), including Cas9 protein domains HNH, RuvC, Cas9-PI, Cas9-REC, Cas9-BH.

In the first iteration, the search criteria included (a) identification of large protein sequences (approximately 1,000 amino acids); (b) that these protein sequences were annotated as an endonuclease or Cas9 or contained an HNH pfam domain; (c) were located in the same operon with a Cas1 and a Cas2, but not a Cas5 or a Cas3; and that the proteins were in the same operon within <2 kb of a CRISPR loci. These criteria suggest that the identified proteins are RNA-guided DNA nucleases. In this round, eight proteins were identified as CRISPR enzymes.

In subsequent iterations, search criteria included (a) identification of large protein sequences (approximately 1,000 amino acids); (b) that these protein sequences were annotated as an endonuclease or Cas9 or contained an HNH pfam domain; (c) were located in the same operon with a Cast or a Cas2, but not a Cas5 or a Cas3; and that the proteins were in the same operon within <2 kb of a CRISPR loci. Results were additionally reviewed to identify un-annotated Cas2.

This resulted in identification of an additional 22 CRISPR enzymes. Combined iterations yielded 31 novel CRISPR enzymes which are represented by SEQ ID NO: 1-30, and 36.

Example 2: Identification of Additional Novel CRISPR Enzymes

Novel CRISPR enzymes were further identified by iterative bioinformatic searching of bacterial genome sequences using the following searching criteria. Bacterial genomes were scanned for CRISPR sequences using the CRISPR recognition toolv1.1 (Bland C, et al. CRISPR Recognition Tool (CRT): a tool for automatic detection of clustered regularly interspaced palindromic repeats. BMC Bioinformatics. 2007 Jun. 18; 8(1):209; web address: room220.com/crt). From this analysis, 18,709 CRISPR loci were identified that had an annotated protein located <20 Kb away. Next, the identified protein sequences were annotated using hmmsearch v3.1v2 against the Pfam-A database version 28.0. and these were filtered according to the following: (a) the CRISPR loci had a gene <20 kb away whose product was predicted to contain a "Cas Cas1" domain; (b) the protein had a gene <20 kb away whose product was predicted to contain a "CRISPR Cas2" domain (1,190 CRISPR loci remaining after step (a) and (b)); (c) the protein did not have a gene <20 kb away whose product was predicted to contain a "Cas Cas5d" domain (225 CRISPR loci remaining); (d) the protein did not have a gene <20 kb away whose product was predicted to contain a "Cas9-BH", "Cas9_REC", or "Cas9_PI" domain (173 CRISPR loci with this criteria); (e) the protein had a gene <20 kb away whose product was predicted to contain a domain annotated as an "endonuclease" (29 CRISPR loci remaining). The result of this search and filtering gave a list of 29 CRISPR arrays that had an associated Cast and Cas2 (suggesting that they are functional adaptive immune systems), and did not have an associated Cas5 (suggesting that they were not Type I, III, or IV CRISPR systems) or an associated high-homology Cas9 (suggesting that they were not typical Type II CRISPR systems). There were 15 putative CRISPR enzymes that were associated with these 29 CRISPR arrays, of which only 7 were >900 amino acids in length, and of these 7, 5 had not been previously identified by other methods as described in Example 1. These 5 are represented by SEQ ID NO: 31-35.

Pfam annotation of the identified CRISPR enzymes is presented in Table 1. For each protein, the domain ID is indicated (for example, Cas9-BH, Cas9_Rec, or HNH_4), then the domain E-value, then the endpoint coordinate symbol, followed by the pfam domain coordinates. For each pair of query and target endpoint coordinates, the endpoint coordinate symbols have the following meaning: both ends of the alignment ended internally is represented by " . . . "; both ends of the alignment were full-length flush to the ends of the query and target is represented by "[ ]"; where only the left or right end was flush/full-length is represented by "[." Or ".]," respectively. (Eddy, S. R., HMMER3 beta test: User's Guide, Version 3.0b3; November 2009, at the web site hmmer.org)

TABLE 1

Pfam annotation of the identified CRISPR enzymes.

| PRT SEQ ID NO | NUC SEQ ID NO | Organism | [Pfam domainID, domain E-value, Hmm coverage in symbols, Envelop coor, "_" used as separator) |
|---|---|---|---|
| 1 | 37 | *Lysinibacillus* sp. multi | [Cas9-BH: (0.0000000067_[._49 . . . 79); Cas9_REC: (0.027_. . ._39 . . . 115); Cas_Cmr5: (13_. . ._154 . . . 231); DDE_Tnp_1_3: (18_. . ._166 . . . 227); Erf4: (0.28_. . ._181 . . . 348); HNH_4: (0.0000000000000012_[._832 . . . 881) |

TABLE 1-continued

Pfam annotation of the identified CRISPR enzymes.

| PRT SEQ ID NO | NUC SEQ ID NO | Organism | [Pfam domainID, domain E-value, Hmm coverage in symbols, Envelop coor, "_" used as separator) |
|---|---|---|---|
| 2 | 38 | *Bacillus* sp. multi | [Cas9-BH: (0.12_[._50 ... 75); HNH_4: (1.1E-23_[ ]_560 ... 614) |
| 3 | 39 | *Bacillus* sp. multi | [Cas9-BH: (0.056_[._50 ... 76); HNH_4: (7.8E-24_[ ]_560 ... 614); RuvC: (0.0023_[._4 ... 47) |
| 4 | 40 | *Bacillus* sp. multi | [Cas9-BH: (0.15_[._50 ... 75); HNH: (0.0013_..._559 ... 611); HNH_4: (6.1_..._76 ... 92) |
| 5 | 41 | *Bacillus* sp. multi | [Cas9-BH: (0.15_[._50 ... 75); HNH_4: (6.1_..._76 ... 92); ING: (0.31_..._84 ... 221) |
| 6 | 42 | *Bacillus* sp. multi | [Cas9-BH: (0.12_[._50 ... 75); HNH_4: (1.1E-23_[ ]_560 ... 614) |
| 7 | 43 | *Bacillus* sp. multi | [HNH_4: (2.5E-24_[ ]_560 ... 614); RuvC: (0.003_[._4 ... 48) |
| 8 | 44 | *Bacillus* sp. multi | [Cas9-BH: (0.15_[._50 ... 75); HNH_4: (1E-23_[ ]_560 ... 614); RuvC: (0.0021_[._4 ... 47) |
| 9 | 45 | *Bacillus* sp. multi | [Cas9-BH: (0.15_[._50 ... 75); HNH_4: (1.1E-23_[ ]_560 ... 614) |
| 10 | 46 | *Bacillus* sp. multi | [HNH_4: (2.5E-24_[ ]_560 ... 614); RuvC: (0.003_[._4 ... 48) |
| 11 | 47 | *Bacillus* sp. multi | [Cas9-BH: (0.12_[._50 ... 75); HNH_4: (1.1E-23_[ ]_560 ... 614) |
| 12 | 48 | *Bacillus* sp. multi | [Cas9-BH: (0.056_[._50 ... 76); HNH_4: (7.8E-24_[ ]_560 ... 614); RuvC: (0.0023_[._4 ... 47) |
| 13 | 49 | *Bacillus* sp. multi | [Cas9-BH: (0.12_[._50 ... 75); HNH_4: (1.2E-24_[ ]_560 ... 614) |
| 14 | 50 | *Bacillus* sp. multi | [Cas9-BH: (0.15_[._50 ... 75); HNH_4: (7.3E-24_[ ]_560 ... 614); RuvC: (0.0031_[._4 ... 47) |
| 15 | 51 | *Bacillus* sp. multi | [Cas9-BH: (0.15_[._50 ... 75); HNH_4: (6.1_..._76 ... 92); ING: (0.31_..._84 ... 221); YodL: (0.15_..._145 ... 217) |
| 16 | 52 | *Bacillus* sp. multi | [Cas9-BH: (0.15_[._50 ... 75); HNH_4: (7.8E-24_[ ]_560 ... 614) |
| 17 | 53 | *Brevibacillus laterosporus* | [Cas9-BH: (0.00017_[._50 ... 76); Cas9_REC: (0.0000000000001_..._227 ... 435); HNH: (0.000081_..._562 ... 613); HNH_4: (4.1E-24_[ ]_562 ... 616) |
| 18 | 54 | *Bacillus thuringiensis* | [Cas9-BH: (0.00011_[._50 ... 76); Cas9_REC: (0.000000000000063_..._227 ... 437); DUF4276: (1.1_..._258 ... 424); HNH: (0.000052_..._562 ... 613); HNH_4: (2.6E-24_[ ]_562 ... 616) |
| 19 | 55 | *Brevibacillus laterosporus* | [Cas9-BH: (0.00017_[._50 ... 76); Cas9_REC: (0.00000000000011_..._227 ... 435); HNH: (0.000081_..._562 ... 613); HNH_4: (4.1E-24_[ ]_562 ... 616) |
| 20 | 56 | *Brevibacillus laterosporus* | [Cas9-BH: (0.00017_[._50 ... 76); Cas9_REC: (0.00000000000068_..._227 ... 435); HNH: (0.000081_..._562 ... 613); HNH_4: (4.1E-24_[ ]_562 ... 616) |
| 21 | 57 | *Enterococcus faecalis* | [Cas9-BH: (0.0000000029_[ ]_62 ... 94); Cas9_PI: (8.7_..._212 ... 282); Cas9_REC: (1.8E-187_[ ]_181 ... 724); Castor_Poll_mid: (0.0001_..._567 ... 649); DUF327: (3.8_..._223 ... 392); HNH: (0.00028_..._837 ... 880); HNH_4: (1.3E-21_[._832 ... 883); RRXRR: (0.000029_..._1 ... 92) |
| 22 | 58 | *Brevibacillus brevis* | [Cas9-BH: (0.00017_[._50 ... 76); Cas9_REC: (0.0000000000001_..._227 ... 435); HNH: (0.000081_..._562 ... 613); HNH_4: (4.1E-24_[ ]_562 ... 616) |
| 23 | 59 | *Brevibacillus laterosporus* | [Cas9-BH: (0.000045_[._50 ... 75); Cas9_REC: (0.0000000000003_..._227 ... 435); HNH: (0.00012_..._561 ... 613); HNH_4: (1.2E-23_[ ]_562 ... 616) |
| 24 | 60 | *Bacillus* sp. multi | [HNH_4: (8E-24_[ ]_566 ... 620); SF1-HH: (3.2_..._62 ... 178) |
| 25 | 61 | *Bacillus* sp. multi | [Cas9-BH: (0.15_[._50 ... 75); HNH_4: (8.7E-23_[._560 ... 614) |
| 26 | 62 | *Brevibacillus laterosporus* | [Cas9-BH: (0.00017_[._50 ... 76); Cas9_REC: (0.0000000000005_..._227 ... 435); HNH: (0.000081_..._562 ... 613); HNH_4: (4.1E-24_[ ]_562 ... 616) |
| 27 | 63 | *Bacillus thuringiensis* | [Cas9-BH: (0.0031_[._44 ... 70); HNH: (0.000049_..._580 ... 630); HNH_4: (4.4E-23_[ ]_580 ... 633) |
| 28 | 64 | *Enterococcus faecalis* | [Cas9-BH: (0.0000000029_[ ]_62 ... 94); Cas9_PI: (8.2_..._211 ... 282); Cas9_REC: (5E-188_[ ]_181 ... 724); Castor_Poll_mid: (0.00013_..._567 ... 649); DUF327: (3.5_..._219 ... 392); HNH: (0.0004_..._837 ... 880); HNH_4: (4.8E-21_[._832 ... 883); RRXRR: (0.000037_..._1 ... 92) |
| 29 | 65 | *Sphingobium* sp. novel | [HNH_4: (7.2E-22_[ ]_602 ... 655) |
| 30 | 66 | *Undibacterium pigrum* | [HNH_4: (6.4E-22_[ ]_587 ... 640) |
| 31 | 67 | *Bacillus* sp. multi | [HNH_4: (7.9E-24_[ ]_560 ... 614); SF1-HH: (3.2_..._56 ... 172) |
| 32 | 68 | *Chryseobacterium* sp. novel | [CTK3_C: (0.83_..._145 ... 219); HNH_4: (1.7E-21_[._759 ... 812) |
| 33 | 69 | *Novosphingobium rosa* | [GATA-N: (0.00063_..._570 ... 674); HNH: (0.0000000014_[ ]_472 ... 524); HNH_4: (9.4E-23_[ ]_472 ... 527); zf-ribbon_3: (0.00047_..._466 ... 478); zinc_ribbon_2: (0.00058_..._467 ... 479) |
| 34 | 70 | *Chryseobacterium* sp. novel | [HNH: (0.000000013_[._621 ... 672); HNH_4: (2.8E-20_[ ]_621 ... 675); RBB1NT: (3.7_..._881 ... 930) |
| 35 | 71 | *Labrys methylaminiphilus* | [DUF3253: (0.097_..._273 ... 326); HNH_4: (9E-22_[ ]_593 ... 646) |

TABLE 1-continued

Pfam annotation of the identified CRISPR enzymes.

| PRT SEQ ID NO | NUC SEQ ID NO | Organism | [Pfam domainID, domain E-value, Hmm coverage in symbols, Envelop coor, "_" used as separator] |
|---|---|---|---|
| 36 | 72 | *Brevibacillus brevis* | [Cas9-BH: (0.00017_[._50 . . . 76); Cas9_REC: (0.0000000000001_. . ._227 . . . 435); HNH: (0.000081_. . ._562 . . . 613); HNH_4: (4.1E-24_[ ]_562 . . . 616); |
| 73 | 74 | *Brevibacillus parabrevis* | [DUF1041: (0.83_. . ._55 . . . 107); Flavoprotein: (0.00077_. . ._104 . . . 212); zf-C4H2: (18_. . ._47 . . . 98) |

CRISPR array sequences associated with the identified CRISPR enzymes, along with the sequence coordinates of CRISPR repeats and spacers within each array, are listed in Table 2. TracrRNA and crRNA sequences were also predicted and for each CRISPR enzyme, the tracrRNA and crRNA sequences can be fused with all possible combinations to produce single guide RNAs (sgRNAs). Examples of the predicted tracrRNAs, crRNAs, and sgRNAs (with a GAAA loop sequence connecting crRNA and tracrRNA) are listed in Table 3.

TABLE 2

CRISPR Array Sequences

| PRT SEQ ID NO: | DNA SEQ ID NO: | CRISPR array SEQ ID NO: | Coordinates for CRISPR repeats | Coordinates for CRISPR spacers |
|---|---|---|---|---|
| 1 | 37 | 101 | [1 . . . 36]; [67 . . . 102]; [133 . . . 168]; [199 . . . 234]; [265 . . . 300]; [331 . . . 366]; [397 . . . 432]; [463 . . . 498]; [529 . . . 564]; [595 . . . 630]; [661 . . . 696]; [727 . . . 762]; [793 . . . 828]; [859 . . . 894]; [925 . . . 960]; [991 . . . 1026]; [1057 . . . 1092]; [1123. . .1158]; [1189 . . . 1224]; [1255 . . . 1290]; [1321 . . . 1356]; [1387 . . . 1422]; [1453 . . . 1488]; [1519 . . . 1554]; [1585 . . . 1620]; [1651 . . . 1686]; [1717 . . . 1752]; [1783 . . . 1818]; [1849 . . . 1884]; [1915 . . . 1950]; [1981 . . . 2016]; [2047 . . . 2082]; [2113 . . . 2148]; [2179 . . . 2214]; [2245 . . . 2280]; [2310 . . . 2345]; [2376 . . . 2411]; [2442 . . . 2477]; [2508 . . . 2543]; [2574 . . . 2609]; [2640 . . . 2675]; [2706 . . . 2741]; [2772 . . . 2807]; [2838 . . . 2873]; [2904 . . . 2939]; [2970 . . . 3005]; [3036 . . . 3071]; [3102 . . . 3137]; [3168 . . . 3203]; [3234 . . . 3269]; [3300 . . . 3335]; [3366 . . . 3401]; [3432 . . . 3467]; [3498 . . . 3533]; [3564 . . . 3599]; [3630 . . . 3665]; [3696 . . . 3731]; [3762 . . . 3797]; [3828 . . . 3863]; [3894 . . . 3929]; [3960 . . . 3995]; [4026 . . . 4061]; [4092 . . . 4127]; [4158 . . . 4193]; [4224 . . . 4259]; [4290 . . . 4325]; [4356 . . . 4391]; [4422 . . . 4457]; [4488 . . . 4523]; [4554 . . . 4589]; [4620 . . . 4655]; [4686 . . . 4721]; [4752 . . . 4787]; [4818 . . . 4853]; [4884 . . . 4919]; [4950 . . . 4985]; [5016 . . . 5051]; [5082 . . . 5117]; [5148 . . . 5183]; [5214 . . . 5249]; [5280 . . . 5315]; [5346 . . . 5381]; [5412 . . . 5447]; [5478 . . . 5513]; [5544 . . . 5579]; [5610 . . . 5645]; [5676 . . . 5711]; [5742 . . . 5777]; [5808 . . . 5843]; [5874 . . . 5909]; [5940 . . . 5975]; [6006 . . . 6041]; [6072 . . . 6107]; [6138 . . . 6173]; [6204 . . . 6239]; [6271 . . . 6306]; [6337 . . . 6372]; [6403 . . . 6438]; [6469 . . . 6504]; [6535 . . . 6570]; [6601 . . . 6636]; [6667 . . . 6702]; [6733 . . . 6768]; [6799 . . . 6834]; [6865 . . . 6900]; [6931 . . . 6966]; [6997 . . . 7032]; [7063 . . . 7098]; [7129 . . . 7164]; [7195 . . . 7230]; [7261 . . . 7296]; [7327 . . . 7362]; [7393 . . . 7428]; [7460 . . . 7495]; [7526 . . . 7561]; [7592 . . . 7627]; [7658 . . . 7693]; [7724 . . . 7759]; [7790 . . . 7825]; [7856 . . . 7891]; [7922 . . . 7957]; [7988 . . . 8023]; [8054 . . . 8089]; [8120 . . . 8155]; [8186 . . . 8221]; [8252 . . . 8287]; [8318 . . . 8353] | [37 . . . 66]; [103 . . . 132]; [169 . . . 198]; [235 . . . 264]; [301 . . . 330]; [367 . . . 396]; [433 . . . 462]; [499 . . . 528]; [565 . . . 594]; [631 . . . 660]; [697 . . . 726]; [763 . . . 792]; [829 . . . 858]; [895 . . . 924]; [961 . . . 990]; [1027 . . . 1056]; [1093 . . . 1122]; [1159 . . . 1188]; [1225 . . . 1254]; [1291 . . . 1320]; [1357 . . . 1386]; [1423 . . . 1452]; [1489 . . . 1518]; [1555 . . . 1584]; [1621 . . . 1650]; [1687 . . . 1716]; [1753 . . . 1782]; [1819 . . . 1848]; [1885 . . . 1914]; [1951 . . . 1980]; [2017 . . . 2046]; [2083 . . . 2112]; [2149 . . . 2178]; [2215 . . . 2244]; [2281 . . . 2309]; [2346 . . . 2375]; [2412 . . . 2441]; [2478 . . . 2507]; [2544 . . . 2573]; [2610 . . . 2639]; [2676 . . . 2705]; [2742 . . . 2771]; [2808 . . . 2837]; [2874 . . . 2903]; [2940 . . . 2969]; [3006 . . . 3035]; [3072 . . . 3101]; [3138 . . . 3167]; [3204 . . . 3233]; [3270 . . . 3299]; [3336 . . . 3365]; [3402 . . . 3431]; [3468 . . . 3497]; [3534 . . . 3563]; [3600 . . . 3629]; [3666 . . . 3695]; [3732 . . . 3761]; [3798 . . . 3827]; [3864 . . . 3893]; [3930 . . . 3959]; [3996 . . . 4025]; [4062 . . . 4091]; [4128 . . . 4157]; [4194 . . . 4223]; [4260 . . . 4289]; [4326 . . . 4355]; [4392 . . . 4421]; [4458 . . . 4487]; [4524 . . . 4553]; [4590 . . . 4619]; [4656 . . . 4685]; [4722 . . . 4751]; [4788 . . . 4817]; [4854 . . . 4883]; [4920 . . . 4949]; [4986 . . . 5015]; [5052 . . . 5081]; [5118 . . . 5147]; [5184 . . . 5213]; [5250 . . . 5279]; [5316 . . . 5345]; [5382 . . . 5411]; [5448 . . . 5477]; [5514 . . . 5543]; [5580 . . . 5609]; [5646 . . . 5675]; [5712 . . . 5741]; [5778 . . . 5807]; [5844 . . . 5873]; [5910 . . . 5939]; [5976 . . . 6005]; [6042 . . . 6071]; [6108 . . . 6137]; [6174 . . . 6203]; [6240 . . . 6270]; [6307 . . . 6336]; [6373 . . . 6402]; [6439 . . . 6468]; [6505 . . . 6534]; [6571 . . . 6600]; [6637 . . . 6666]; [6703 . . . 6732]; [6769 . . . 6798]; [6835 . . . 6864]; [6901 . . . 6930]; [6967 . . . 6996]; [7033 . . . 7062]; [7099 . . . 7128]; [7165 . . . 7194]; [7231 . . . 7260]; [7297 . . . 7326]; [7363 . . . 7392]; [7429 . . . 7459]; [7496 . . . 7525]; [7562 . . . 7591]; [7628 . . . 7657]; [7694 . . . 7723]; [7760 . . . 7789]; [7826 . . . 7855]; [7892 . . . 7921]; [7958 . . . 7987]; [8024 . . . 8053]; [8090 . . . 8119]; [8156 . . . 8185]; [8222 . . . 8251]; [8288 . . . 8317]; [8354 . . . 8383] |
| 2 | 38 | 102 | [1 . . . 19]; [66 . . . 84]; [132 . . . 150]; [198 . . . 216]; [264 . . . 282]; [330 . . . 348]; [395 . . . 413]; [461 . . . 479]; [527 . . . 545]; [593 . . . 611] | [20 . . . 65]; [85 . . . 131]; [151 . . . 197]; [217 . . . 263]; [283 . . . 329]; [349 . . . 394]; [414 . . . 460]; [480 . . . 526]; [546 . . . 592]; [612 . . . 665] |
| 2 | 38 | 103 | [1 . . . 35]; [66 . . . 100]; [132 . . . 166]; [197 . . . 231]; [263 . . . 297]; [329 . . . 363]; [395 . . . 429]; [461 . . . 495]; [527 . . . 561]; [593 . . . 627] | [36 . . . 65]; [101 . . . 131]; [167 . . . 196]; [232 . . . 262]; [298 . . . 328]; [364 . . . 394]; [430 . . . 460]; [496 . . . 526]; [562 . . . 592]; [628 . . . 657] |

TABLE 2-continued

CRISPR Array Sequences

| PRT SEQ ID NO: | DNA SEQ ID NO: | CRISPR array SEQ ID NO: | Coordinates for CRISPR repeats | Coordinates for CRISPR spacers |
|---|---|---|---|---|
| 3 | 39 | 104 | [1 . . . 36]; [66 . . . 101]; [131 . . . 166]; [197 . . . 232]; [262 . . . 297]; [328 . . . 363]; [393 . . . 428] | [37 . . . 65]; [102 . . . 130]; [167 . . . 196]; [233 . . . 261]; [298 . . . 327]; [364 . . . 392]; [429 . . . 458] |
| 4 | 40 | 105 | [1 . . . 36]; [67 . . . 102]; [133 . . . 168]; [198 . . . 233]; [264 . . . 299]; [330 . . . 365]; [396 . . . 431]; [462 . . . 497]; [528 . . . 563] | [37 . . . 66]; [103 . . . 132]; [169 . . . 197]; [234 . . . 263]; [300 . . . 329]; [366 . . . 395]; [432 . . . 461]; [498 . . . 527]; [564 . . . 593] |
| 5 | 41 | 106 | [1 . . . 37]; [66 . . . 102]; [132 . . . 168]; [198 . . . 234]; [264 . . . 300]; [330 . . . 366]; [396 . . . 432] | [38 . . . 65]; [103 . . . 131]; [169 . . . 197]; [235 . . . 263]; [301 . . . 329]; [367 . . . 395]; [433 . . . 459] |
| 5 | 41 | 107 | [1 . . . 29]; [67 . . . 95]; [133 . . . 161]; [198 . . . 226]; [264 . . . 292]; [330 . . . 358]; [396 . . . 424]; [463 . . . 491]; [528 . . . 556] | [30 . . . 66]; [96 . . . 132]; [162 . . . 197]; [227 . . . 263]; [293 . . . 329]; [359 . . . 395]; [425 . . . 462]; [492 . . . 527]; [557 . . . 593] |
| 6 | 42 | 108 | [1 . . . 19]; [67 . . . 85]; [133 . . . 151]; [198 . . . 216]; [264 . . . 282]; [330 . . . 348]; [396 . . . 414]; [462 . . . 480]; [528 . . . 546]; [593 . . . 611]; [659 . . . 677]; [725 . . . 743]; [791 . . . 809] | [20 . . . 66]; [86 . . . 132]; [152 . . . 197]; [217 . . . 263]; [283 . . . 329]; [349 . . . 395]; [415 . . . 461]; [481 . . . 527]; [547 . . . 592]; [612 . . . 658]; [678 . . . 724]; [744 . . . 790]; [810 . . . 863] |
| 6 | 42 | 109 | [1 . . . 35]; [67 . . . 101]; [133 . . . 167]; [198 . . . 232]; [264 . . . 298]; [330 . . . 364]; [396 . . . 430] | [36 . . . 66]; [102 . . . 132]; [168 . . . 197]; [233 . . . 263]; [299 . . . 329]; [365 . . . 395]; [431 . . . 460] |
| 7 | 43 | 110 | [1 . . . 19]; [67 . . . 85]; [132 . . . 150]; [197 . . . 215]; [263 . . . 281]; [328 . . . 346]; [394 . . . 412]; [461 . . . 479]; [527 . . . 545]; [591 . . . 609]; [652 . . . 670]; [718 . . . 736]; [784 . . . 802] | [20 . . . 66]; [86 . . . 131]; [151 . . . 196]; [216 . . . 262]; [282 . . . 327]; [347 . . . 393]; [413 . . . 460]; [480 . . . 526]; [546 . . . 590]; [610 . . . 651]; [671 . . . 717]; [737 . . . 783]; [803 . . . 844] |
| 8 | 44 | 111 | [1 . . . 37]; [81 . . . 116]; [147 . . . 183]; [212 . . . 248] | [38 . . . 66]; [117 . . . 145]; [184 . . . 211]; [249 . . . 274] |
| 9 | 45 | 112 | [1 . . . 36]; [80 . . . 115]; [146 . . . 181]; [212 . . . 247]; [278 . . . 313]; [343 . . . 377] | [37 . . . 65]; [116 . . . 145]; [182 . . . 211]; [248 . . . 277]; [314 . . . 343]; [378 . . . 407] |
| 10 | 46 | 113 | [1 . . . 19]; [67 . . . 85]; [133 . . . 151]; [198 . . . 216]; [264 . . . 282]; [329 . . . 347]; [395 . . . 413]; [462 . . . 480]; [528 . . . 546]; [592 . . . 610]; [653 . . . 671]; [719 . . . 737]; [785 . . . 803] | [20 . . . 66]; [86 . . . 132]; [152 . . . 197]; [217 . . . 263]; [283 . . . 328]; [348 . . . 394]; [414 . . . 461]; [481 . . . 527]; [547 . . . 591]; [611 . . . 652]; [672 . . . 718]; [738 . . . 784]; [804 . . . 850] |
| 11 | 47 | 114 | [1 . . . 35]; [80 . . . 115]; [146 . . . 181]; [212 . . . 247]; [278 . . . 313]; [344 . . . 379]; [410 . . . 445] | [36 . . . 65]; [116 . . . 145]; [182 . . . 211]; [248 . . . 277]; [314 . . . 343]; [380 . . . 409]; [446 . . . 474] |
| 12 | 48 | 115 | [1 . . . 36]; [83 . . . 118]; [149 . . . 184] | [37 . . . 66]; [119 . . . 148]; [185 . . . 214] |
| 13 | 49 | 116 | [1 . . . 19]; [67 . . . 85]; [128 . . . 146]; [194 . . . 212]; [259 . . . 277]; [325 . . . 343]; [392 . . . 410]; [458 . . . 476]; [522 . . . 540]; [583 . . . 601]; [649 . . . 667]; [717 . . . 735] | [20 . . . 66]; [86 . . . 127]; [147 . . . 193]; [213 . . . 258]; [278 . . . 324]; [344 . . . 391]; [411 . . . 457]; [477 . . . 521]; [541 . . . 582]; [602 . . . 648]; [668 . . . 716]; [736 . . . 782] |
| 14 | 50 | 117 | [1 . . . 34]; [66 . . . 99]; [132 . . . 165]; [198 . . . 231]; [264 . . . 297]; [330 . . . 363]; [396 . . . 429]; [462 . . . 495] | [35 . . . 65]; [100 . . . 131]; [166 . . . 197]; [232 . . . 263]; [298 . . . 329]; [364 . . . 395]; [430 . . . 461]; [496 . . . 538] |
| 15 | 51 | 118 | [1 . . . 36]; [67 . . . 102]; [134 . . . 169] | [37 . . . 66]; [103 . . . 133]; [170 . . . 200] |
| 16 | 52 | 119 | [1 . . . 35]; [66 . . . 101]; [131 . . . 166]; [197 . . . 232]; [262 . . . 297]; [328 . . . 363]; [394 . . . 429]; [459 . . . 494] | [36 . . . 65]; [102 . . . 130]; [167 . . . 196]; [233 . . . 261]; [298 . . . 327]; [364 . . . 393]; [430 . . . 458]; [495 . . . 524] |
| 17 | 53 | 120 | [1 . . . 36]; [67 . . . 102]; [138 . . . 173]; [205 . . . 240]; [271 . . . 306] | [37 . . . 66]; [103 . . . 137]; [174 . . . 204]; [241 . . . 270]; [307 . . . 336] |
| 17 | 53 | 121 | [1 . . . 22]; [53 . . . 74]; [94 . . . 115] | [23 . . . 52]; [75 . . . 93]; [116 . . . 137] |
| 18 | 54 | 122 | [1 . . . 36]; [67 . . . 102]; [133 . . . 168]; [199 . . . 234]; [265 . . . 300]; [331 . . . 366] | [37 . . . 66]; [103 . . . 132]; [169 . . . 198]; [235 . . . 264]; [301 . . . 330]; [367 . . . 396] |
| 18 | 54 | 123 | [1 . . . 22]; [53 . . . 74]; [94 . . . 115] | [23 . . . 52]; [75 . . . 93]; [116 . . . 137] |
| 19 | 55 | 124 | [1 . . . 36]; [66 . . . 101]; [132 . . . 167]; [198 . . . 233]; [264 . . . 299]; [330 . . . 365]; [395 . . . 430]; [461 . . . 496] | [37 . . . 65]; [102 . . . 131]; [168 . . . 197]; [234 . . . 263]; [300 . . . 329]; [366 . . . 394]; [431 . . . 460]; [497 . . . 526] |
| 20 | 56 | 125 | [1 . . . 35]; [82 . . . 116]; [148 . . . 182]; [214 . . . 248]; [280 . . . 314]; [346 . . . 380]; [412 . . . 446]; [477 . . . 511]; [543 . . . 577]; [609 . . . 643]; [675 . . . 709]; [741 . . . 775] | [36 . . . 65]; [117 . . . 147]; [183 . . . 213]; [249 . . . 279]; [315 . . . 345]; [381 . . . 411]; [447 . . . 476]; [512 . . . 542]; [578 . . . 608]; [644 . . . 674]; [710 . . . 740]; [776 . . . 806] |
| 21 | 57 | 126 | [1 . . . 36]; [67 . . . 102]; [133 . . . 168]; [199 . . . 234]; [265 . . . 300]; [331 . . . 366]; [397 . . . 432]; [463 . . . 498]; [529 . . . 564]; [595 . . . 630]; [661 . . . 696]; [727 . . . 762]; [793 . . . 828]; [859 . . . 894] | [37 . . . 66]; [103 . . . 132]; [169 . . . 198]; [235 . . . 264]; [301 . . . 330]; [367 . . . 396]; [433 . . . 462]; [499 . . . 528]; [565 . . . 594]; [631 . . . 660]; [697 . . . 726]; [763 . . . 792]; [829 . . . 858]; [895 . . . 924] |
| 22 | 58 | 127 | [1 . . . 36]; [67 . . . 102]; [133 . . . 168]; [199 . . . 234]; [265 . . . 300]; [331 . . . 366]; [397 . . . 432]; [469 . . . 504]; [535 . . . 570]; [601 . . . 636] | [37 . . . 66]; [103 . . . 132]; [169 . . . 198]; [235 . . . 264]; [301 . . . 330]; [367 . . . 396]; [433 . . . 468]; [505 . . . 534]; [571 . . . 600]; [637 . . . 666] |

TABLE 2-continued

CRISPR Array Sequences

| PRT SEQ ID NO: | DNA SEQ ID NO: | CRISPR array SEQ ID NO: | Coordinates for CRISPR repeats | Coordinates for CRISPR spacers |
|---|---|---|---|---|
| 22 | 58 | 128 | [1 . . . 22]; [53 . . . 74]; [94 . . . 115] | [23 . . . 52]; [75 . . . 93]; [116 . . . 137] |
| 23 | 59 | 129 | [1 . . . 36]; [67 . . . 102]; [133 . . . 168]; [199 . . . 234]; [265 . . . 300]; [331 . . . 366]; [397 . . . 432]; [463 . . . 498]; [529 . . . 564]; [595 . . . 630]; [661 . . . 696]; [727 . . . 762] | [37 . . . 66]; [103 . . . 132]; [169 . . . 198]; [235 . . . 264]; [301 . . . 330]; [367 . . . 396]; [433 . . . 462]; [499 . . . 528]; [565 . . . 594]; [631 . . . 660]; [697 . . . 726]; [763 . . . 792] |
| 24 | 60 | 130 | [1 . . . 36]; [67 . . . 102]; [133 . . . 168]; [199 . . . 234]; [265 . . . 300]; [331 . . . 366]; [397 . . . 432]; [465 . . . 500]; [531 . . . 566]; [597 . . . 632]; [663 . . . 698]; [729 . . . 764]; [800 . . . 835]; [866 . . . 901]; [937 . . . 972] | [37 . . . 66]; [103 . . . 132]; [169 . . . 198]; [235 . . . 264]; [301 . . . 330]; [367 . . . 396]; [433 . . . 464]; [501 . . . 530]; [567 . . . 596]; [633 . . . 662]; [699 . . . 728]; [765 . . . 799]; [836 . . . 865]; [902 . . . 936]; [973 . . . 1001] |
| 24 | 60 | 131 | [1 . . . 37]; [67 . . . 103]; [133 . . . 169] | [38 . . . 66]; [104 . . . 132]; [170 . . . 199] |
| 25 | 61 | 132 | [1 . . . 35]; [64 . . . 98]; [129 . . . 163]; [195 . . . 229] | [36 . . . 63]; [99 . . . 128]; [164 . . . 194]; [230 . . . 259] |
| 25 | 61 | 133 | [1 . . . 36]; [67 . . . 102]; [133 . . . 168]; [199 . . . 234]; [266 . . . 301]; [302 . . . 331]; [368 . . . 398]; [399 . . . 434]; [466 . . . 501] | [37 . . . 66]; [103 . . . 132]; [169 . . . 198]; [235 . . . 265]; [302 . . . 331]; [368 . . . 398]; [435 . . . 465]; [502 . . . 531] |
| 26 | 62 | 134 | [1 . . . 36]; [67 . . . 102]; [133 . . . 168]; [199 . . . 234] | [37 . . . 66]; [103 . . . 132]; [169 . . . 198]; [235 . . . 264] |
| 27 | 63 | 135 | [1 . . . 36]; [67 . . . 102]; [133 . . . 168]; [199 . . . 234]; [265 . . . 300]; [331 . . . 366]; [397 . . . 432]; [463 . . . 498]; [529 . . . 564]; [595 . . . 630]; [661 . . . 696]; [727 . . . 762]; [793 . . . 828] | [37 . . . 66]; [103 . . . 132]; [169 . . . 198]; [235 . . . 264]; [301 . . . 330]; [367 . . . 396]; [433 . . . 462]; [499 . . . 528]; [565 . . . 594]; [631 . . . 660]; [697 . . . 726]; [763 . . . 792]; [829 . . . 858] |
| 28 | 64 | 136 | [1 . . . 36]; [67 . . . 102]; [133 . . . 168]; [199 . . . 234]; [265 . . . 300]; [331 . . . 366]; [397 . . . 432]; [463 . . . 498]; [529 . . . 564]; [595 . . . 630]; [661 . . . 696]; [727 . . . 762]; [793 . . . 828]; [859 . . . 894]; [925 . . . 960]; [991 . . . 1026]; [1057 . . . 1092] | [37 . . . 66]; [103 . . . 132]; [169 . . . 198]; [235 . . . 264]; [301 . . . 330]; [367 . . . 396]; [433 . . . 462]; [499 . . . 528]; [565 . . . 594]; [631 . . . 660]; [697 . . . 726]; [763 . . . 792]; [829 . . . 858]; [895 . . . 924]; [961 . . . 990]; [1027 . . . 1056]; [1093 . . . 1122] |
| 29 | 65 | 137 | [1 . . . 36]; [68 . . . 103]; [134 . . . 169]; [200 . . . 235]; [266 . . . 301]; [332 . . . 367]; [398 . . . 433]; [464 . . . 499]; [530 . . . 565]; [596 . . . 631]; [661 . . . 696]; [727 . . . 762]; [793 . . . 828]; [859 . . . 894]; [925 . . . 960]; [991 . . . 1026]; [1057 . . . 1092]; [1123. .1158]; [1189 . . . 1224]; [1255 . . . 1290]; [1321 . . . 1356]; [1388 . . . 1423]; [1454 . . . 1489]; [1520 . . . 1555]; [1586 . . . 1621]; [1652 . . . 1687]; [1718 . . . 1753] | [37 . . . 67]; [104 . . . 133]; [170 . . . 199]; [236 . . . 265]; [302 . . . 331]; [368 . . . 397]; [434 . . . 463]; [500 . . . 529]; [566 . . . 595]; [632 . . . 660]; [697 . . . 726]; [763 . . . 792]; [829 . . . 858]; [895 . . . 924]; [961 . . . 990]; [1027 . . . 1056]; [1093 . . . 1122]; [1159 . . . 1188]; [1225 . . . 1254]; [1291 . . . 1320]; [1357 . . . 1387]; [1424 . . . 1453]; [1490 . . . 1519]; [1556 . . . 1585]; [1622 . . . 1651]; [1688 . . . 1717]; [1754 . . . 1783] |
| 30 | 66 | 138 | [1 . . . 36]; [67 . . . 102]; [133 . . . 168]; [199 . . . 234]; [265 . . . 300]; [331 . . . 366] | [37 . . . 66]; [103 . . . 132]; [169 . . . 198]; [235 . . . 264]; [301 . . . 330]; [367 . . . 396] |
| 31 | 67 | 139 | [1 . . . 36]; [67 . . . 102]; [133 . . . 168]; [199 . . . 234]; [265 . . . 300]; [331 . . . 366]; [397 . . . 432]; [465 . . . 500]; [531 . . . 566]; [597 . . . 632]; [663 . . . 698]; [729 . . . 764]; [800 . . . 835]; [866 . . . 901]; [937 . . . 972] | [37 . . . 66]; [103 . . . 132]; [169 . . . 198]; [235 . . . 264]; [301 . . . 330]; [367 . . . 396]; [433 . . . 464]; [501 . . . 530]; [567 . . . 596]; [633 . . . 662]; [699 . . . 728]; [765 . . . 799]; [836 . . . 865]; [902 . . . 936]; [973 . . . 1001] |
| 31 | 67 | 140 | [1 . . . 37]; [67 . . . 103]; [133 . . . 169] | [38 . . . 66]; [104 . . . 132]; [170 . . . 199] |
| 32 | 68 | 141 | [1 . . . 47]; [100 . . . 146]; [177 . . . 223]; [254 . . . 300]; [331 . . . 377]; [408 . . . 454]; [485 . . . 531]; [562 . . . 608]; [639 . . . 685]; [716 . . . 762]; [793 . . . 839]; [870 . . . 916]; [948 . . . 994]; [1025 . . . 1071]; [1102 . . . 1148]; [1179 . . . 1225]; [1256 . . . 1302]; [1333 . . . 1379]; [1410 . . . 1456]; [1487 . . . 1533]; [1564 . . . 1610]; [1641 . . . 1687]; [1718 . . . 1764]; [1795 . . . 1841]; [1871 . . . 1916]; [1948 . . . 1994]; [2025 . . . 2071]; [2102 . . . 2148] | [48 . . . 77]; [147 . . . 176]; [224 . . . 253]; [301 . . . 330]; [378 . . . 407]; [455 . . . 484]; [532 . . . 561]; [609 . . . 638]; [686 . . . 715]; [763 . . . 792]; [840 . . . 869]; [917 . . . 947]; [995 . . . 1024]; [1072 . . . 1101]; [1149 . . . 1178]; [1226 . . . 1255]; [1303 . . . 1332]; [1380 . . . 1409]; [1457 . . . 1486]; [1534 . . . 1563]; [1611 . . . 1640]; [1688 . . . 1717]; [1765 . . . 1794]; [1842 . . . 1871]; [1917 . . . 1946]; [1995 . . . 2024]; [2072 . . . 2101]; [2149 . . . 2178] |
| 33 | 69 | 142 | [1 . . . 36]; [67 . . . 102]; [133 . . . 168]; [199 . . . 234]; [265 . . . 300]; [331 . . . 366]; [397 . . . 432]; [463 . . . 498]; [529 . . . 564]; [595 . . . 630]; [661 . . . 696]; [727 . . . 762]; [793 . . . 828]; [859 . . . 894]; [925 . . . 960]; [991 . . . 1026]; [1057 . . . 1092]; [1123 . . . 1158]; [1189 . . . 1224]; [1254 . . . 1289]; [1320 . . . 1355]; [1386 . . . 1421]; [1452 . . . 1487]; [1518 . . . 1553]; [1584 . . . 1619]; [1650 . . . 1685]; [1716 . . . 1751]; [1782 . . . 1817]; [1848 . . . 1883]; [1914 . . . 1949]; [1980 . . . 2015]; [2046 . . . 2081]; [2112 . . . 2147]; [2178 . . . 2213]; [2244 . . . 2279]; [2310 . . . 2345]; [2376 . . . 2411]; [2442 . . . 2477]; [2508 . . . 2543]; [2574 . . . 2609]; [2640 . . . 2675]; [2706 . . . 2741]; [2772 . . . 2807] | [37 . . . 66]; [103 . . . 132]; [169 . . . 198]; [235 . . . 264]; [301 . . . 330]; [367 . . . 396]; [433 . . . 462]; [499 . . . 528]; [565 . . . 594]; [631 . . . 660]; [697 . . . 726]; [763 . . . 792]; [829 . . . 858]; [895 . . . 924]; [961 . . . 990]; [1027 . . . 1056]; [1093 . . . 1122]; [1159 . . . 1188]; [1225 . . . 1253]; [1290 . . . 1319]; [1356 . . . 1385]; [1422 . . . 1451]; [1488 . . . 1517]; [1554 . . . 1583]; [1620 . . . 1649]; [1686 . . . 1715]; [1752 . . . 1781]; [1818 . . . 1847]; [1884 . . . 1913]; [1950 . . . 1979]; [2016 . . . 2045]; [2082 . . . 2111]; [2148 . . . 2177]; [2214 . . . 2243]; [2280 . . . 2309]; [2346 . . . 2375]; [2412 . . . 2441]; [2478 . . . 2507]; [2544 . . . 2573]; [2610 . . . 2639]; [2676 . . . 2705]; [2742 . . . 2771]; [2808 . . . 2837] |

TABLE 2-continued

CRISPR Array Sequences

| PRT SEQ ID NO: | DNA SEQ ID NO: | CRISPR array SEQ ID NO: | Coordinates for CRISPR repeats | Coordinates for CRISPR spacers |
|---|---|---|---|---|
| 34 | 70 | 143 | [1 . . . 46]; [77 . . . 122]; [153 . . . 198]; [229 . . . 274]; [305 . . . 350]; [381 . . . 426]; [457 . . . 502]; [533 . . . 578]; [609 . . . 654]; [685 . . . 730]; [761 . . . 806]; [837 . . . 882]; [913 . . . 958]; [989 . . . 1034] | [47 . . . 76]; [123 . . . 152]; [199 . . . 228]; [275 . . . 304]; [351 . . . 380]; [427 . . . 456]; [503 . . . 532]; [579 . . . 608]; [655 . . . 684]; [731 . . . 760]; [807 . . . 836]; [883 . . . 912]; [959 . . . 988]; [1035 . . . 1064] |
| 35 | 71 | 144 | [1 . . . 36]; [67 . . . 102]; [133 . . . 168]; [200 . . . 235]; [266 . . . 301]; [332 . . . 367]; [398 . . . 433]; [464 . . . 499]; [530 . . . 565]; [596 . . . 631]; [662 . . . 697]; [728 . . . 763]; [794 . . . 829]; [860 . . . 895]; [926 . . . 961]; [992 . . . 1027]; [1058 . . . 1093]; [1124 . . . 1159]; [1190 . . . 1225]; [1256 . . . 1291] | [37 . . . 66]; [103 . . . 132]; [169 . . . 199]; [236 . . . 265]; [302 . . . 331]; [368 . . . 397]; [434 . . . 463]; [500 . . . 529]; [566 . . . 595]; [632 . . . 661]; [698 . . . 727]; [764 . . . 793]; [830 . . . 859]; [896 . . . 925]; [962 . . . 991]; [1028 . . . 1057]; [1094 . . . 1123]; [1160 . . . 1189]; [1226 . . . 1255]; [1292 . . . 1321] |
| 36 | 72 | 145 | [1 . . . 36]; [67 . . . 102]; [133 . . . 168]; [199 . . . 234]; [271 . . . 306]; [337 . . . 372]; [403 . . . 438] | [37 . . . 66]; [103 . . . 132]; [169 . . . 198]; [235 . . . 270]; [307 . . . 336]; [373 . . . 402]; [439 . . . 468] |

TABLE 3

Predicted tracrRNAs, crRNAs, and fused tracrRNA:crRNAs for CRISPR enzymes listed in Table 1.

| PRT SEQ ID NO: | DNA SEQ ID NO: | TracrRNA SEQ ID NO: | crRNA SEQ ID NO: | Fused TracrRNA:crRNA SEQ ID NO: |
|---|---|---|---|---|
| 17 | 53 | 255 | 266 | 277 |
| 18 | 54 | 256 | 267 | 278 |
| 19 | 55 | 257, 288, 291 | 268, 289, 292 | 279, 290, 293 |
| 22 | 58 | 258 | 269 | 280 |
| 23 | 59 | 259, 294, 297 | 270, 295, 298 | 281, 296, 299 |
| 26 | 62 | 260 | 271 | 282 |
| 27 | 63 | 261 | 272 | 283 |
| 30 | 66 | 262 | 273 | 284 |
| 32 | 68 | 263 | 274 | 285 |
| 35 | 71 | 264 | 275 | 286 |
| 36 | 72 | 265 | 276 | 287 |

Example 3: Identification of a Novel Class of CRISPR Enzymes

During the bioinformatic analysis done as detailed in Example 1, one large protein (1108 amino acids) was found in close association with a CRISPR operon which was not annotated as a Cas9 or as containing an HNH domain. This CRISPR enzyme was named NCC1 (Novel CRISPR Cas) represented by SEQ ID NO: 73. Three CRISPR regions (SEQ ID NOs: 146, 147, and 148) were identified for NCC1 and two putative tracrRNAs (SEQ ID NOs: 162 and 165) were also predicted. Additionally, within the NCC1 operon, there was one sequence indicative of a Cas1Cas4 fusion, and another putative Cas2 sequence. The structure of the genomic region comprising NCC1, CRISPRs, and tracrRNAs is depicted in FIG. 1.

A number of the NCC1 homologs (SEQ ID NOs: 75-87) were identified and the associated CRISPR array sequences were predicted for some of the identified NCC1 homologs and listed in Table 4. TracrRNA and crRNA sequences were also predicted and listed in Table 5 for some of the identified NCC1 homologs. TracrRNAs and crRNAs can be fused with all possible combinations to form single guide RNAs and some fused tracrRNA:crRNA sequences with a GAAA loop sequence are listed in Table 5 as examples.

TABLE 4

Predicted CRISPR array sequences and coordinates for NCC1 and NCC1 homologs.

| PRT SEQ ID NO: | DNA SEQ ID NO: | Organism | CRISPR array SEQ ID NO: | Coordinates for CRISPR repeats | Coordinates for CRISPR spacers |
|---|---|---|---|---|---|
| 73 | 74 | Brevibacillus parabrevis | 146 | [1 . . . 36]; [72 . . . 107]; [144 . . . 179]; [219 . . . 254]; [292 . . . 327]; [364 . . . 399]; [438 . . . 473]; [511 . . . 546]; [582 . . . 617]; [655 . . . 690]; [726 . . . 761] | [37 . . . 71]; [108 . . . 143]; [180 . . . 218]; [255 . . . 291]; [328 . . . 363]; [400 . . . 437]; [474 . . . 510]; [547 . . . 581]; [618 . . . 654]; [691 . . . 725]; [762 . . . 805] |
| 73 | 74 | Brevibacillus parabrevis | 147 | [1 . . . 36]; [73 . . . 108]; [150 . . . 185]; [224 . . . 259]; [297 . . . 332]; [372 . . . 407]; [444 . . . 479] | [37 . . . 72]; [109 . . . 149]; [186 . . . 223]; [260 . . . 296]; [333 . . . 371]; [408 . . . 443]; [480 . . . 513] |

TABLE 4-continued

Predicted CRISPR array sequences and coordinates for NCC1 and NCC1 homologs.

| PRT SEQ ID NO: | DNA SEQ ID NO: | Organism | CRISPR array SEQ ID NO: | Coordinates for CRISPR repeats | Coordinates for CRISPR spacers |
|---|---|---|---|---|---|
| 73 | 74 | Brevibacillus parabrevis | 148 | [1 . . . 36]; [73 . . . 108]; [144 . . . 179]; [215 . . . 250]; [287 . . . 322]; [358 . . . 393]; [428 . . . 463]; [502 . . . 537]; [577 . . . 612]; [648 . . . 683]; [720 . . . 755]; [795 . . . 830]; [868 . . . 903]; [938 . . . 973]; [1011 . . . 1046] | [37 . . . 72]; [109 . . . 143]; [180 . . . 214]; [251 . . . 286]; [323 . . . 357]; [394 . . . 427]; [464 . . . 501]; [538 . . . 576]; [613 . . . 647]; [684 . . . 719]; [756 . . . 794]; [831 . . . 867]; [904 . . . 937]; [974 . . . 1010]; [1047 . . . 1083] |
| 79 | 92 | Alicyclobacillus acidoterrestris | 149 | [1 . . . 36]; [72 . . . 107]; [145 . . . 180]; [219 . . . 254]; [289 . . . 324]; [362 . . . 397] | [37 . . . 71]; [108 . . . 144]; [181 . . . 218]; [255 . . . 288]; [325 . . . 361]; [398 . . . 433] |
| 80 | 93 | Brevibacillus sp. Multi | 150 | [1 . . . 36]; [76 . . . 111]; [147 . . . 182]; [221 . . . 256]; [296 . . . 331]; [366 . . . 401]; [438 . . . 473]; [509 . . . 544]; [582 . . . 617]; [656 . . . 691]; [729 . . . 764]; [805 . . . 840]; [875 . . . 910]; [946 . . . 981]; [1019 . . . 1054] | [37 . . . 75]; [112 . . . 146]; [183 . . . 220]; [257 . . . 295]; [332 . . . 365]; [402 . . . 437]; [474 . . . 508]; [545 . . . 581]; [618 . . . 655]; [692 . . . 728]; [765 . . . 804]; [841 . . . 874]; [911 . . . 945]; [982 . . . 1018]; [1055 . . . 1098] |
| 80 | 93 | Brevibacillus sp. Multi | 151 | [1 . . . 36]; [76 . . . 111]; [147 . . . 182]; [222 . . . 257]; [296 . . . 331]; [367 . . . 402]; [439 . . . 474]; [514 . . . 549]; [586 . . . 621]; [661 . . . 696]; [732 . . . 767]; [807 . . . 842]; [882 . . . 917]; [957 . . . 992]; [1028 . . . 1063]; [1103 . . . 1138]; [1179 . . . 1214] | [37 . . . 75]; [112 . . . 146]; [183 . . . 221]; [258 . . . 295]; [332 . . . 366]; [403 . . . 438]; [475 . . . 513]; [550 . . . 585]; [622 . . . 660]; [697 . . . 731]; [768 . . . 806]; [843 . . . 881]; [918 . . . 956]; [993 . . . 1027]; [1064 . . . 1102]; [1139 . . . 1178]; [1215 . . . 1250] |
| 80 | 93 | Brevibacillus sp. Multi | 152 | [1 . . . 36]; [72 . . . 107]; [145 . . . 180]; [216 . . . 251]; [287 . . . 322]; [359 . . . 394]; [432 . . . 467]; [505 . . . 540] | [37 . . . 71]; [108 . . . 144]; [181 . . . 215]; [252 . . . 286]; [323 . . . 358]; [395 . . . 431]; [468 . . . 504]; [541 . . . 575] |
| 81 | 94 | Brevibacillus sp. multi | 153 | [1 . . . 36]; [72 . . . 107]; [143 . . . 178]; [220 . . . 255]; [296 . . . 331]; [368 . . . 403]; [444 . . . 479]; [520 . . . 555]; [594 . . . 629]; [667 . . . 702]; [737 . . . 772]; [810 . . . 845]; [881 . . . 916]; [955 . . . 990]; [1031 . . . 1066]; [1101 . . . 1136]; [1176 . . . 1211]; [1252 . . . 1287]; [1326 . . . 1361]; [1398 . . . 1433]; [1472 . . . 1507]; [1544 . . . 1579]; [1616 . . . 1651]; [1689 . . . 1724]; [1766 . . . 1801]; [1838 . . . 1873]; [1911 . . . 1946]; [1984 . . . 2019]; [2056 . . . 2091]; [2127 . . . 2162]; [2200 . . . 2235]; [2270 . . . 2305]; [2342 . . . 2377]; [2415 . . . 2450]; [2487 . . . 2522]; [2560 . . . 2595]; [2632 . . . 2667]; [2705 . . . 2740]; [2780 . . . 2815]; [2850 . . . 2885]; [2925 . . . 2960]; [2996 . . . 3031]; [3069 . . . 3104]; [3145 . . . 3180]; [3216 . . . 3251]; [3290 . . . 3325]; [3364 . . . 3399]; [3439 . . . 3474]; [3511 . . . 3546]; [3586 . . . 3621]; [3657 . . . 3692]; [3731 . . . 3766]; [3804 . . . 3839]; [3875 . . . 3910]; [3947 . . . 3982]; [4022 . . . 4057]; [4093 . . . 4128]; [4166 . . . 4201]; [4240 . . . 4275]; [4311 . . . 4346]; [4383 . . . 4418]; [4456 . . . 4491]; [4530 . . . 4565]; [4603 . . . 4638]; [4677 . . . 4712]; [4748 . . . 4783]; [4818 . . . 4853] | [37 . . . 71]; [108 . . . 142]; [179 . . . 219]; [256 . . . 295]; [332 . . . 367]; [404 . . . 443]; [480 . . . 519]; [556 . . . 593]; [630 . . . 666]; [703 . . . 736]; [773 . . . 809]; [846 . . . 880]; [917 . . . 954]; [991 . . . 1030]; [1067 . . . 1100]; [1137 . . . 1175]; [1212 . . . 1251]; [1288 . . . 1325]; [1362 . . . 1397]; [1434 . . . 1471]; [1508 . . . 1543]; [1580 . . . 1615]; [1652 . . . 1688]; [1725 . . . 1765]; [1802 . . . 1837]; [1874 . . . 1910]; [1947 . . . 1983]; [2020 . . . 2055]; [2092 . . . 2126]; [2163 . . . 2199]; [2236 . . . 2269]; [2306 . . . 2341]; [2378 . . . 2414]; [2451 . . . 2486]; [2523 . . . 2559]; [2596 . . . 2631]; [2668 . . . 2704]; [2741 . . . 2779]; [2816 . . . 2849]; [2886 . . . 2924]; [2961 . . . 2995]; [3032 . . . 3068]; [3105 . . . 3144]; [3181 . . . 3215]; [3252 . . . 3289]; [3326 . . . 3363]; [3400 . . . 3438]; [3475 . . . 3510]; [3547 . . . 3585]; [3622 . . . 3656]; [3693 . . . 3730]; [3767 . . . 3803]; [3840 . . . 3874]; [3911 . . . 3946]; [3983 . . . 4021]; [4058 . . . 4092]; [4129 . . . 4165]; [4202 . . . 4239]; [4276 . . . 4310]; [4347 . . . 4382]; [4419 . . . 4455]; [4492 . . . 4529]; [4566 . . . 4602]; [4639 . . . 4676]; [4713 . . . 4747]; [4784 . . . 4817]; [4854 . . . 4891] |
| 81 | 94 | Brevibacillus sp. multi | 154 | [1 . . . 36]; [74 . . . 109]; [147 . . . 182]; [221 . . . 256]; [292 . . . 327]; [367 . . . 402]; [441 . . . 476]; [512 . . . 547]; [583 . . . 618]; [656 . . . 691]; [727 . . . 762]; [800 . . . 835]; [875 . . . 910]; [946 . . . 981]; [1019 . . . 1054]; [1091 . . . 1126]; [1166 . . . 1201]; [1237 . . . 1272]; [1311 . . . 1346]; [1386 . . . 1421]; [1461 . . . 1496]; [1535 . . . 1570]; [1609 . . . 1644]; [1680 . . . 1715] | [37 . . . 73]; [110 . . . 146]; [183 . . . 220]; [257 . . . 291]; [328 . . . 366]; [403 . . . 440]; [477 . . . 511]; [548 . . . 582]; [619 . . . 655]; [692 . . . 726]; [763 . . . 799]; [836 . . . 874]; [911 . . . 945]; [982 . . . 1018]; [1055 . . . 1090]; [1127 . . . 1165]; [1202 . . . 1236]; [1273 . . . 1310]; [1347 . . . 1385]; [1422 . . . 1460]; [1497 . . . 1534]; [1571 . . . 1608]; [1645 . . . 1679]; [1716 . . . 1755] |
| 82 | 95 | Methylobacterium nodularis | 155 | [1 . . . 36]; [72 . . . 107]; [143 . . . 178]; [212 . . . 247]; [283 . . . 318]; [354 . . . 389]; [424 . . . 459]; [495 . . . 530] | [37 . . . 71]; [108 . . . 142]; [179 . . . 211]; [248 . . . 282]; [319 . . . 353]; [390 . . . 423]; [460 . . . 494]; [531 . . . 564] |
| 85 | 98 | Brevibacillus parabrevis | 156 | [1 . . . 36]; [75 . . . 110]; [148 . . . 183]; [224 . . . 259]; [294 . . . 329]; [365 . . . 400]; [438 . . . 473] | [37 . . . 74]; [111 . . . 147]; [184 . . . 223]; [260 . . . 293]; [330 . . . 364]; [401 . . . 437]; [474 . . . 517] |
| 85 | 98 | Brevibacillus parabrevis | 157 | [1 . . . 36]; [76 . . . 111]; [147 . . . 182]; [222 . . . 257]; [296 . . . 331]; [367 . . . 402]; [439 . . . 474]; [514 . . . 549]; [586 . . . 621]; [661 . . . 696]; [732 . . . 767]; [807 . . . 842]; [882 . . . 917]; [958 . . . 993] | [37 . . . 75]; [112 . . . 146]; [183 . . . 221]; [258 . . . 295]; [332 . . . 366]; [403 . . . 438]; [475 . . . 513]; [550 . . . 585]; [622 . . . 660]; [697 . . . 731]; [768 . . . 806]; [843 . . . 881]; [918 . . . 957]; [994 . . . 1029] |
| 85 | 98 | Brevibacillus parabrevis | 158 | [1 . . . 36]; [72 . . . 107]; [145 . . . 180]; [216 . . . 251]; [287 . . . 322]; [361 . . . 396]; [434 . . . 469] | [37 . . . 71]; [108 . . . 144]; [181 . . . 215]; [252 . . . 286]; [323 . . . 360]; [397 . . . 433]; [470 . . . 504] |
| 86 | 99 | Brevibacillus parabrevis | 159 | [1 . . . 36]; [73 . . . 108]; [145 . . . 180]; [217 . . . 252] | [37 . . . 72]; [109 . . . 144]; [181 . . . 216]; [253 . . . 288] |
| 87 | 100 | Brevibacillus fluminis | 160 | [1 . . . 36]; [72 . . . 107]; [142 . . . 177]; [218 . . . 253]; [290 . . . 325]; [362 . . . 397]; [433 . . . 468] | [37 . . . 71]; [108 . . . 141]; [178 . . . 217]; [254 . . . 289]; [326 . . . 361]; [398 . . . 432]; [469 . . . 503] |

TABLE 4-continued

Predicted CRISPR array sequences and coordinates for NCC1 and NCC1 homologs.

| PRT SEQ ID NO: | DNA SEQ ID NO: | Organism | CRISPR array SEQ ID NO: | Coordinates for CRISPR repeats | Coordinates for CRISPR spacers |
|---|---|---|---|---|---|
| 87 | 100 | Brevibacillus fluminis | 161 | [1 . . . 36]; [72 . . . 107]; [142 . . . 177]; [213 . . . 248]; [287 . . . 322]; [358 . . . 393]; [430 . . . 465]; [506 . . . 541]; [578 . . . 613] | [37 . . . 71]; [108 . . . 141]; [178 . . . 212]; [249 . . . 286]; [323 . . . 357]; [394 . . . 429]; [466 . . . 505]; [542 . . . 577]; [614 . . . 648] |

TABLE 5

Predicted TracrRNA and crRNA sequences for NCC1 and NCC1 homologs.

| PRT SEQ ID NO: | DNA SEQ ID NO: | Pre-processed TracrRNA SEQ ID NO: | Pre-processed crRNA SEQ ID NO: | Fused TracrRNA:crRNA SEQ ID NO: | Processed TracrRNA SEQ ID NO: | Processed crRNA SEQ ID NO: | Fused TracrRNA:crRNA SEQ ID NO: |
|---|---|---|---|---|---|---|---|
| 73 | 74 | 162, 165 | 163, 166 | 164, 167 | 192, 195 | 193, 196 | 194, 197 |
| 79 | 92 | 186 | 187 | 188 | 216 | 217 | 218 |
| 80 | 93 | 168, 171 | 169, 172 | 170, 173 | 198, 201 | 199, 202 | 200, 203 |
| 81 | 94 | 174, 177 | 175, 178 | 176, 179 | 204, 207 | 205, 208 | 206, 209 |
| 82 | 95 | 180, 183 | 181, 184 | 182, 185 | 210, 213 | 211, 214 | 212, 215 |
| 87 | 100 | 189 | 190 | 191 | 219 | 220 | 221 |

Figure 2:
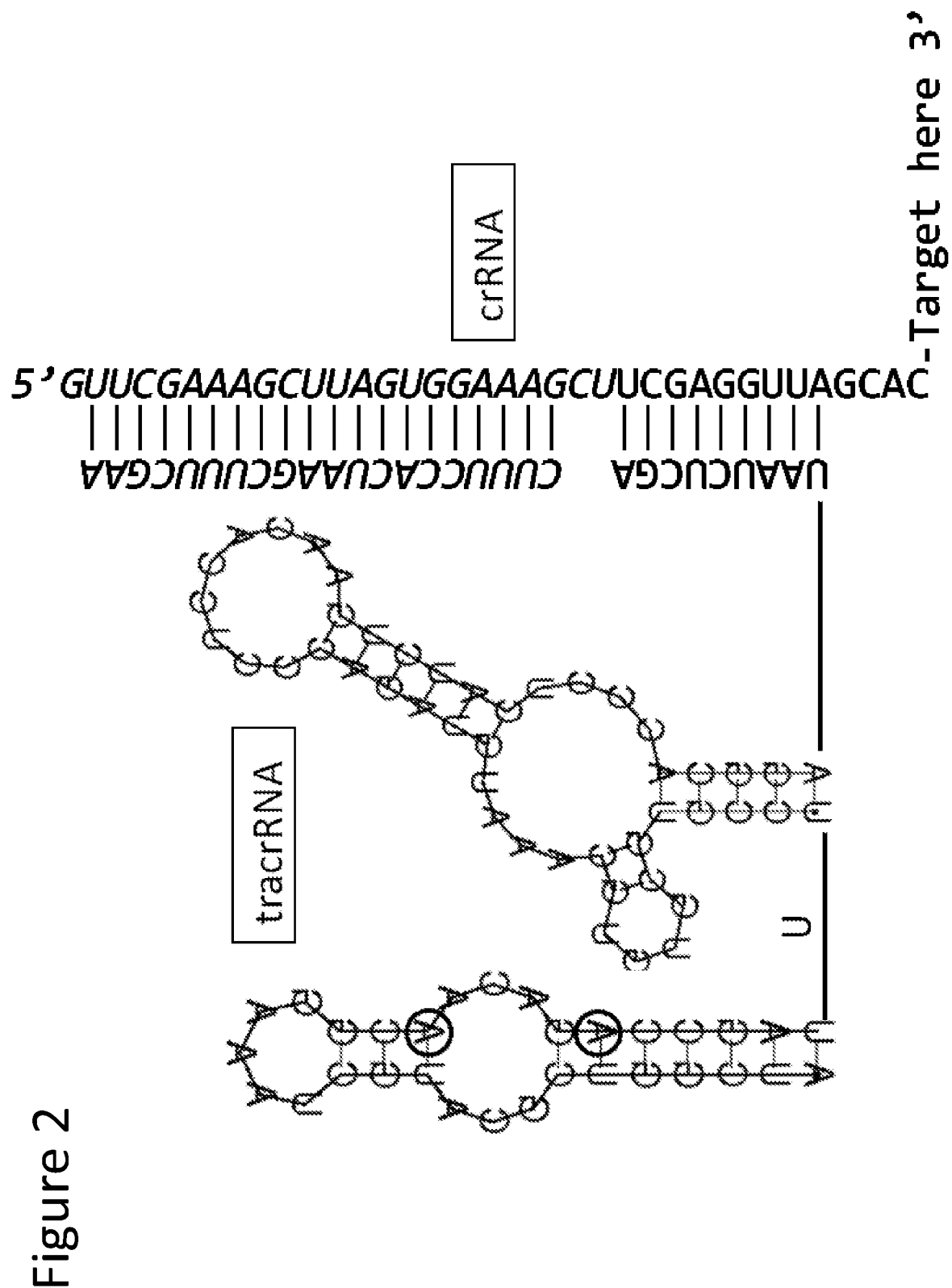
FIG. 2. shows the predicted secondary structure for the putative pre-processed NCC1 guide RNA with the tracrRNA (SEQ ID NO: 165) fused with the crRNA (SEQ ID NO: 166). Two tracrRNAs are predicted for NCC1. The two circled 'A' nucleotides in tracrRNA (SEQ ID NO:165) are both G in the second tracrRNA (SEQ ID NO: 162). The tracrRNA contains two hairpin structures which are connected with an unpaired 'U', illustrated in the figure with the black line connecting the base of each tracrRNA hairpin with the letter 'U'. The portion of tracrRNA complementary to the crRNA is connected to the rest of tracrRNA by a black line. The position of the target specific sequence is illustrated at the 3' end of the crRNA.
Figure 3:
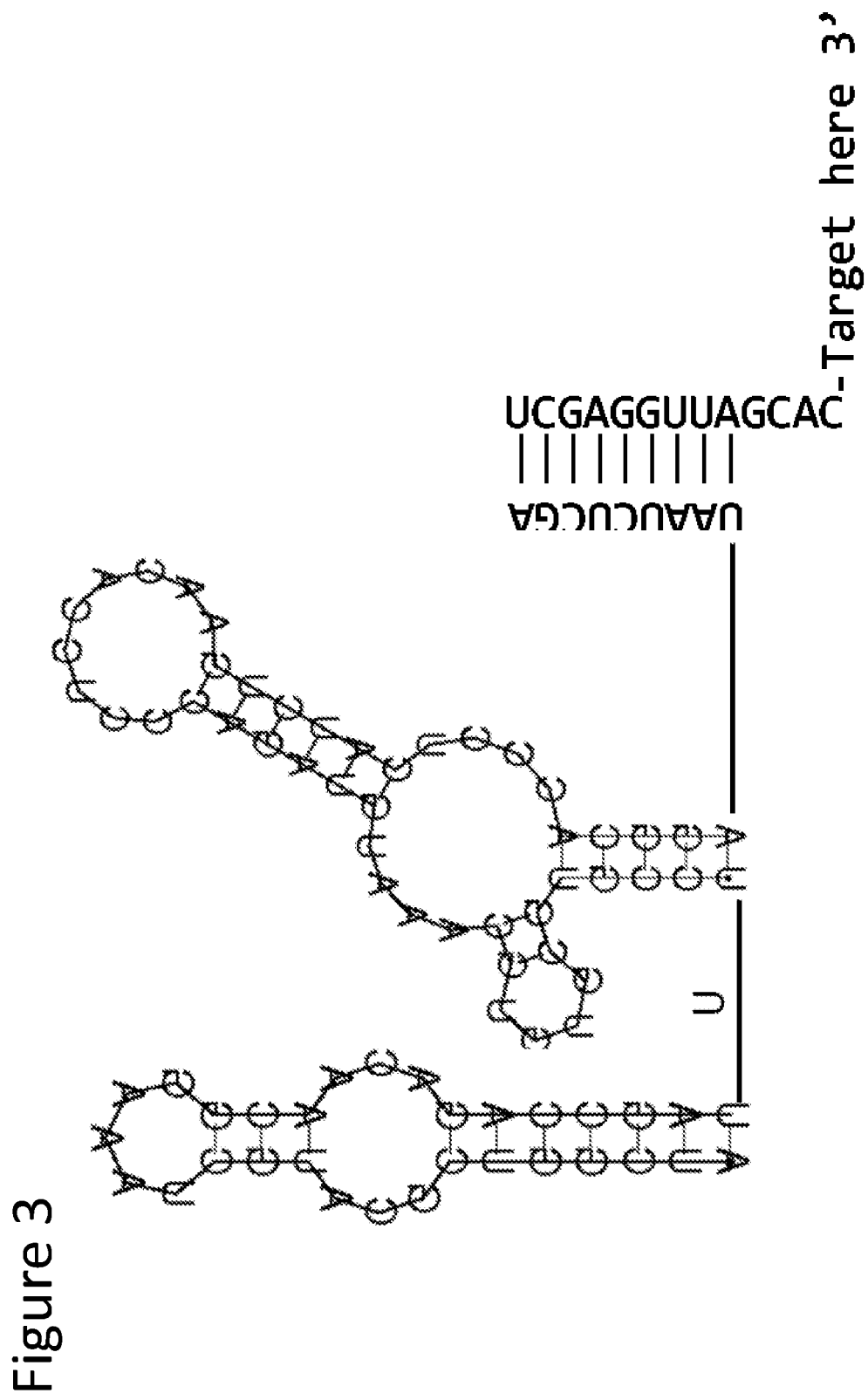
FIG. 3. shows the predicted secondary structure for the putative post-processed NCC1 guide RNA with the tracrRNA (SEQ ID NO: 195) fused with the crRNA (SEQ ID NO: 196).
Figure 4:
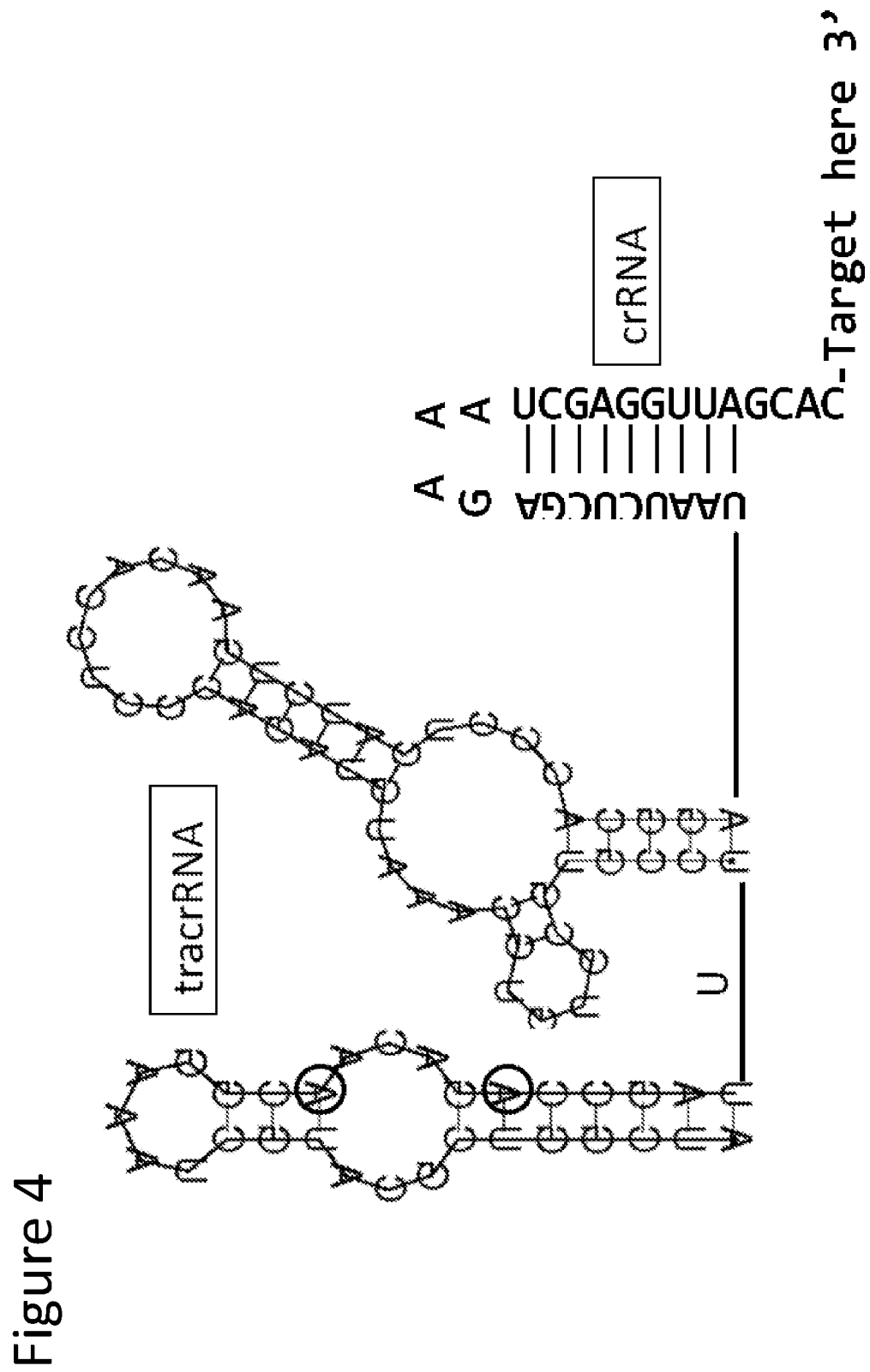
FIG. 4. shows the predicted secondary structure for a single guide RNA (SEQ ID NO: 197) formed by fusing the post-processed tracrRNA (SEQ ID NO: 195) and crRNA (SEQ ID NO: 196) with a short loop sequence GAAA.

For CRISPR enzymes, having hairpins in the tracrRNA is important for nuclease binding. Examining the structure of the predicted NCC1 tracrRNAs showed two putative harpins (FIG. 2). The hairpin formed by the crRNA and tracRNA may undergo processing to form a shorter region of base pairing (FIG. 3). The NCC1 crRNA and tracRNA duplex may be simplified into a single-guide RNA (sgRNA) by fusing the 3' end of the tracrRNA with the 5' end of the crRNA. FIG. 4 shows an example of using a short GAAA sequence as a loop to join the tracrRNA (SEQ ID NO: 195) and the crRNA (SEQ ID NO: 196) to form a sgRNA (SEQ ID NO: 197). To program a target site cleavage by NCC1, the crRNA:tracrRNA duplex or sgRNA is designed to carry a spacer at its 3' end targeting a protospacer sequence from the target locus. An in vitro cleavage assay is then used to validate the RNA-guided target cleavage activity by incubating target DNA with NCC1 protein and in-vitro-transcribed crRNA:tracrRNA duplex or sgRNA (Shmakov et al. Molecular Cell (2015) 60:1-13). In vitro cleavage assay is performed using the lysate of HEK293 cells expressing NCC1 protein in cleavage buffer (NEBuffer 3, 5 mM DTT) for 1 hr. Each cleavage reaction uses 200 ng of target DNA and an equimolar ratio of crRNA:tracrRNA. The RNA is pre-annealed by heating to 95° C. and slowly cooling to 4° C. Target DNA consisted of the first protospacer of the RGEN locus is cloned into pUC19. The pUC19 protospacer construct is linearized by BsaI digestion prior to the cleavage reaction. Reactions are cleaned up using PCR purification columns (QIAGEN) and run on 2% agarose E-gels (Life Technologies).

Example 4: Determination of the CRISPR Enzyme Activity

A high through-put assay is conducted to determine if the identified CRISPR enzymes, (a) have RNA-guided DNA nuclease activity and (b) to identify the associated PAM motifs. This assay is generally applicable to RNA-Guided EndoNucleases (RGENs), which is a reference to DNA modifying enzymes that (1) include endonucleolytic activity and (2) are associated with non-coding RNA species that are capable to guide them to specific polynucleotide target sites for activity. Many of these enzymes may have, beyond endonuclease activity, other functions, which include but not limited to transposases, topoisomerases, recombinases, and resolvases.

Figure 5A:
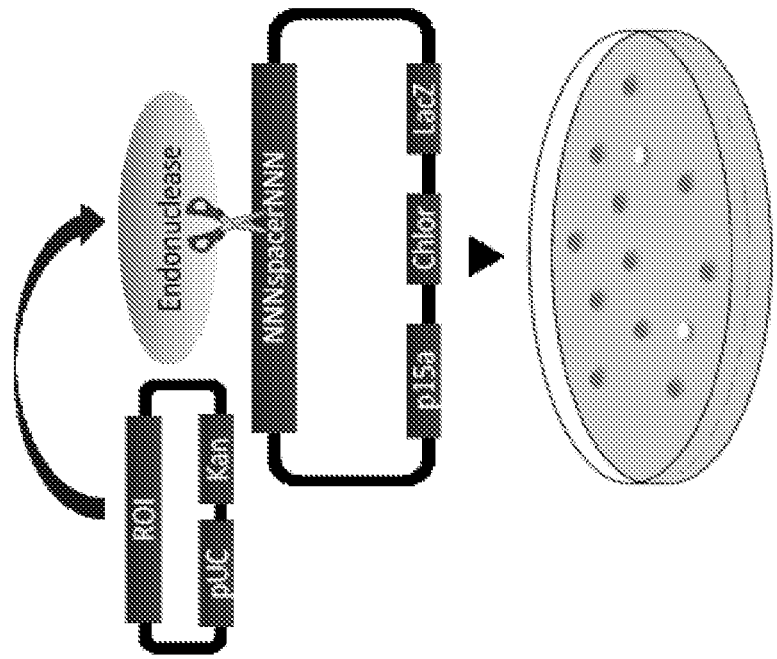
FIGS. 5A. 5B. and 5C. Diagram of assays to validate nuclease activity of the novel CRISPR enzymes described herein FIG. 5A. Diagram of an *Escherichia coli* based blue-white selection assay to screen for nuclease activity. A pUC19 vector with a kanamycin (kan) selection marker was use to clone an RGEN region (ROI) encoding a novel CRISPR enzyme. A second vector comprising the lacZ reporter gene and a target sequence encoding a spacer from the CRISPR region, which is flanked by variable sequence (indicated by NNNspacerNNN) was constructed. The two vectors were co-transformed into *E. coli* cells, and the presence of white colonies indicates cutting by the novel CRISPR enzyme. Sequence analysis is used to confirm the endonuclease activity.

A bacterial genomic region of interest (ROI) including one of the DNA sequences encoding the CRISPR enzymes represented by SEQ ID NOs: 1-73, 75-87, and the associated RNA species in its native genomic environment is cloned into a plasmid. Another 'reporter' construct is also built for each system, which includes one or more of the spacer sequences identified in the associated CRISPR arrays. The spacer(s) are flanked by 12 variable nucleotides at both ends ('NNN'). The reporter constructs have a low-copy replication origin and a selectable marker that is different from that of the RGEN plasmids to allow selection for co-transformants. They also have a LacZ construct that allows blue-white selection. Upon expression of the ROI elements, endonucleolytic activity will cleave the reporter plasmids and thus their copy number will decrease within the cells. These vectors are transformed into Escherichia. coli. When the variable region ('N's) includes a PAM 5' or 3' to the spacer for the RNA-guided DNA nuclease, DNA nuclease activity will introduce double-strand breaks (DSBs), which, in most cases, will lead to degradation and finally elimination of the reporter plasmid. Alternatively, recombination along short regions of homologies will re-circularize the reporter constructs after resections of variable length around the spacer region (Wang et al. 2015 Genet. Mol. Res., 14, 12306-12315). Some of these recombinants will presumably render the LacZ gene dysfunctional, while retaining the selectable marker gene. These mutants can be recognized as white colonies in a lawn of predominantly blue colonies (FIG. 5A). This assay will identify the RGEN systems where the initial endonuclease cleavage is followed by re-circularization of the reporter construct. For RGENs that have additional functions, such as transposase, additional mutations may be introduced before they re-ligate the linear plasmids and thus the selectable marker and reporter genes may not be affected. In those cases, high-throughout sequencing of the reporter plasmids would reveal additional mutations.

Example 5: *Mycobacterium* Cutting Assay

Figure 6:
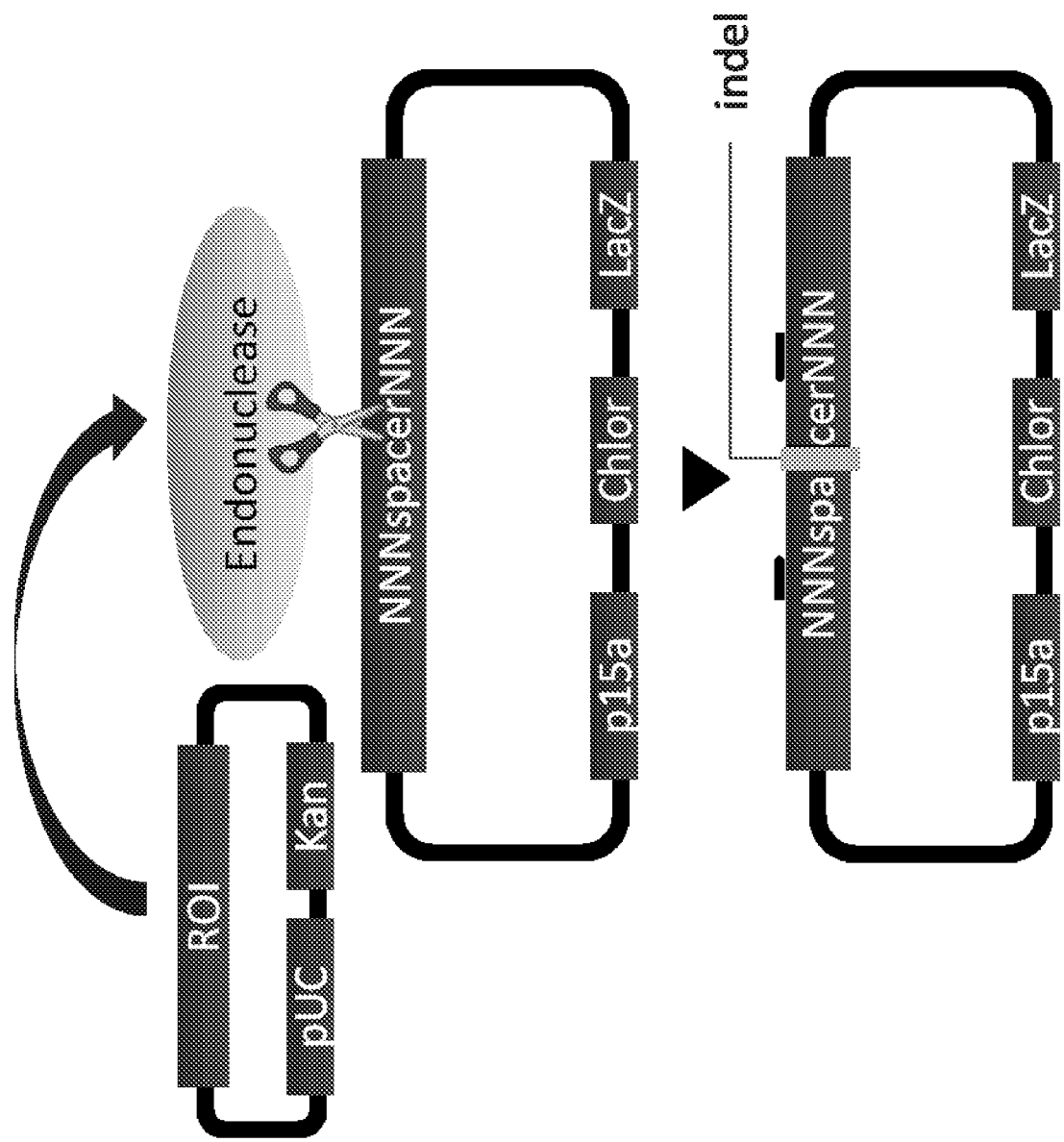
FIG. 6. Diagram of *Mycobacterium* cutting assay to validate nuclease activity of the novel CRISPR enzyme described herein. The same vectors used for the *E. coli* blue-white selection of FIG. 5 are used to co-transform *Mycobacterium*. Due to endogenous plasmid repair in *Mycobacterium*, a double-strand break in the LacZ plasmid is repaired by indels. The presence of indels in the LacZ vector is indicative of novel endonuclease activity.

A group of prokaryotes, namely *Mycobacterium* spp. is capable of repairing cleaved plasmid DNA by a mechanism, called non-homologous end-joining (NHEJ). NHEJ would heal the cut plasmid in an error-prone fashion (see, e.g., FIG. 6). This mechanism could be utilized to identify efficacious CRISPR enzyme systems by detecting either integration of a short oligonucleotide or point mutations at the target site by PCR amplification and/or sequencing. This assay can be used as an alternative of the blue-white selection shown in Example 4.

Example 6: In Vitro Cutting Assay

Figure 5B:
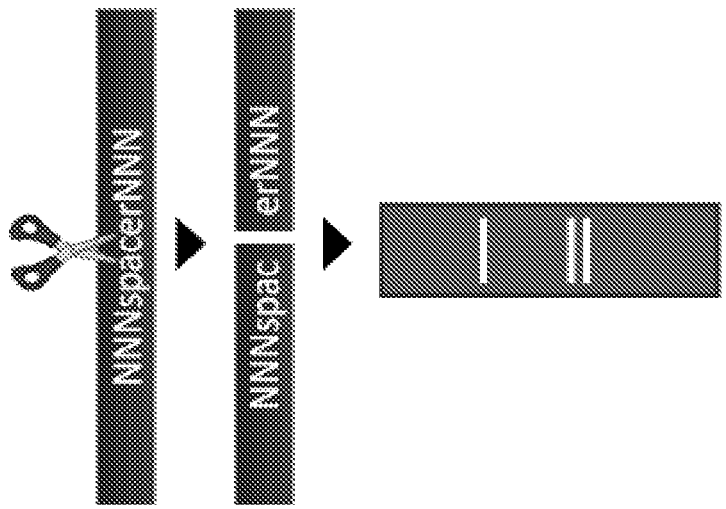
FIG. 5B. Diagram of an in vitro cutting assay. The novel CRISPR enzyme is purified from *E. coli* and the purified protein is incubated in vitro with the DNA target for cutting (NNNspacerNNN). The resulting DNA is (a) analyzed for fragment length by gel electrophoresis, and (b) by sequence analysis.

A sequence encoding one of the CRISPR enzymes represented by SEQ ID NOs: 1-36, 73, 75-87 is cloned into an expression vector and the enzyme is purified. The corresponding genomic region of interest (ROI) including RNA species that are involved in RGEN activity is cloned into a high-copy plasmid, which is transformed into *Escherichia coli*. RNA components associated with the CRISPR enzyme of interest encoded on the ROI construct are identified by RNA-seq. These RNA components are synthesized. The RGEN/RNA complexes are added to synthetic DNA fragments carrying the spacer sequences as shown in FIG. 5B. The cut or uncut, but otherwise mutated DNA fragments will be recollected for sequencing.

Example 7: Determination and Validation of PAM Motif of a CRISPR Enzyme

A bacterial genomic region of interest (ROI) including one of the DNA sequences encoding the CRISPR enzymes represented by SEQ ID NOs: 1-36, 73, 75-87, and the associated RNA species in its native genomic environment is cloned into a plasmid. The vector also comprises a first antibiotic resistance gene, such as kanamycin resistance (Kan). The spacer flanked by 12 bp of Ns is cloned into a second vector comprising a second antibiotic resistance gene, for example tetracycline or chloramphenicol. The two vectors are transformed into *Escherichia coli* and plated on two set of plates containing media with a single antibiotic for selection of the first vector. The second set of plates contains antibiotics for selection against both vectors. Plasmid DNA is prepared from bacteria grown on both sets of plates, PCR amplification of the spacer with flanking N sequence is conducted, and the PCR amplions are deep sequenced to identify sequences which are depleted from the library. These sequences corresponding to the depleted sequence correspond to the PAM motif of the respective CRISPR enzyme which was co-transformed.

Alternatively, the PAM preferences for a CRISPR enzyme can be empirically examined and determined by using a method relying on the in vitro cleavage of plasmid libraries containing a randomized PAM (3' PAM or 5' PAM library) as a function of Nuclease-guide RNA complex (Karvelis et al. Genome Biology (2015) 16:253; Shmakov et al. Molecular Cell (2015) 60:1-13). Randomized PAM plasmid libraries are constructed using synthesized oligonucleotides (IDT) consisting of seven randomized nucleotides either upstream or downstream of the spacer 1 target. The randomized ssDNA oligos are made double stranded by annealing to a short primer and using the large Klenow fragment for second strand synthesis. The dsDNA product is assembled into a linearized PUC19 using Gibson cloning. Stab13 *E. coli* cells are transformed with the cloned products, collected and pooled. Plasmid DNA is harvested using a QIAGEN maxi-prep kit. Transform the pooled library into *E. coli* cells transformed with the RGEN locus. After transformation, cells are plated and selected with antibiotic. After 16 hr of growth, >4×106 cells are harvested and plasmid DNA is extracted using a QIAGEN maxi-prep kit. The target PAM region is amplified and sequenced using an Illumina MiSeq with single-end 150 cycles. Sequences corresponding to both PAMs and non-PAMs are cloned into digested pUC19 and ligated with T4 ligase (Enzymatics). Competent *E. coli* with either the RGEN locus plasmid or pACYC184 control plasmid are transformed with PAM plasmid and plated on LB agar plates supplemented with ampicillin and chloramphenicol. After 18 hr, colonies were counted with OpenCFU (Geissmann, Q. PLoS One 8, 2013).

Example 8: Determination of CRISPR Enzyme Activity in Eukaryotic Cell

Figure 5C:
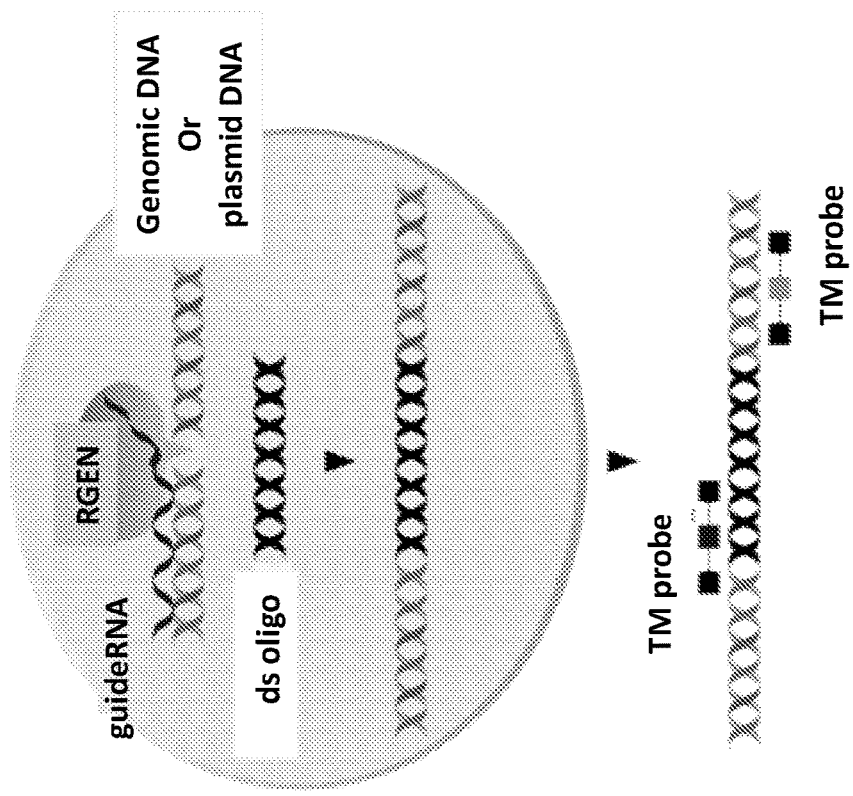
FIG. 5C. Diagram of an in planta cutting assay. The novel CRISPR enzyme and associated guide RNA are cloned into a vector to facilitate expression in a plant cell. The expression vectors, double strand oligo (ds oligo), and (optionally) plasmid DNA containing target sequence are co-transformed into a plant cell. The novel endonuclease activity on either (a) chromosomal DNA, or (b) introduced plasmid template is evaluated with standard molecular biology assays (PCR (Taqman® (TM)), restriction fragment size analysis, or sequencing).

A eukaryotic cell is transformed with an expression vector comprising a heterologous promoter operably linked to a sequence encoding a CRISPR enzyme selected from SEQ ID NOs: 1-36, 73, 75-87, and a sequence encoding an RNA guide comprising a sequence capable of hybridizing with an endogenous sequence of the eukaryotic cell. A donor polynucleotide comprising an exogenous transgene or a sequence for templated editing is further provided to the cell. The CRISPR enzyme complexed with the guide RNA cleaves the genomic DNA at or proximal to the target site and the donor polynucleotide is incorporated by non-homologous end-joining or homologous recombination. Integrations are detected by sequencing amplicons spanning the chromosome-oligo junctions (FIG. 5C).

Example 9: Validation of CRISPR Enzyme Activity Using Blue-White Selection

Figure 7:
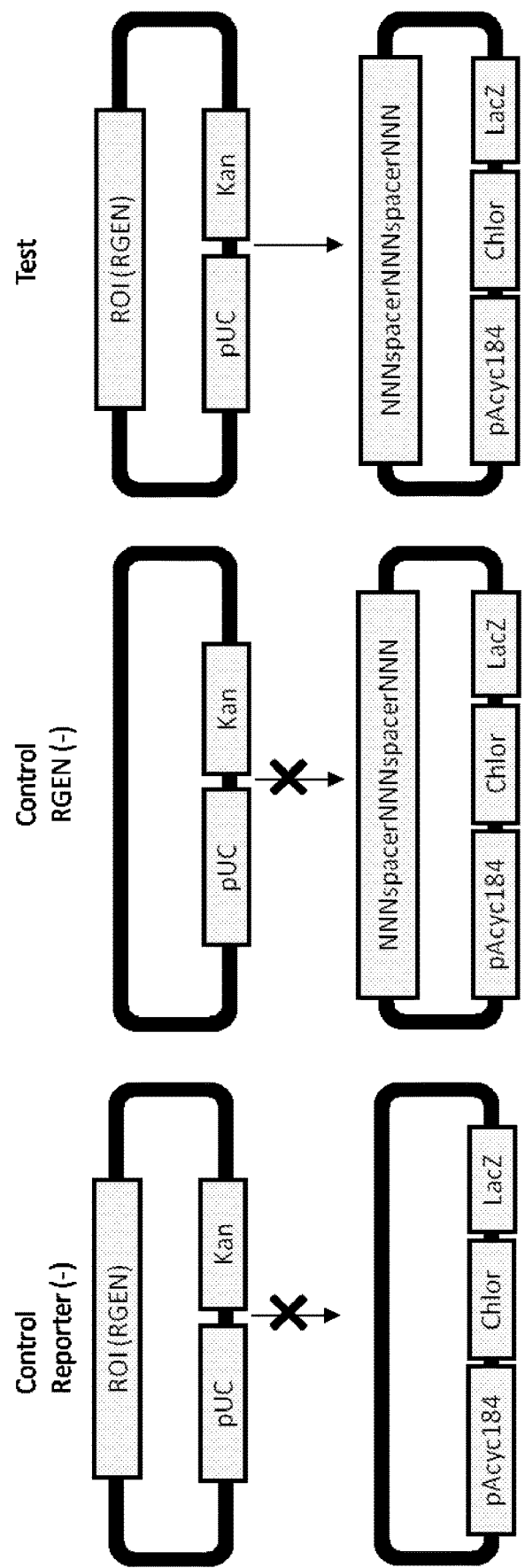
FIG. 7. Diagram of prokaryotic blue-white selection assay design for the validation of CRISPR enzyme activity. The top row shows diagrams of the vectors used for novel CRISPR enzymes (ROI(RGEN)) expression. The bottom row shows diagrams of the vectors containing the putative target sequence (NNNspacerNNNspacerNNN) and the LacZ marker. The left top and bottom pair are the control lacking the target sequence. The middle top and bottom pair are the control lacking the novel CRISPR enzymes (ROI(RGEN)). The right top and bottom pair are the test assay with the respective vectors containing the novel CRISPR enzymes (ROI(RGEN)) and the target sequence.

A phenotypic assay was conducted to determine if novel CRISPR enzymes identified herein exhibit RNA-guided DNA nuclease activity. The concept and design of this assay was detailed in Example 4. CRISPR enzymes (SEQ ID NOs: 2, 3, 23, 32, 34, and 35 in Table 6) were tested and for each, the bacterial genomic region of interest (ROI) comprising the DNA sequence encoding the CRISPR enzyme and the associated RNA species in its native genomic context was cloned into a plasmid. Another 'reporter' plasmid comprising two of the spacer sequences identified in the CRISPR array was also built. The spacer(s) were flanked by 12 variable nucleotides at both ends (depicted as 'NNN' in FIG. 7). The reporter construct had low-copy replication origin (pAcyc184) and a selectable marker (chloramphenicol resistance) that is different from that of the RGEN plasmids (kanamycin resistance) to allow selection for co-transformants. It also carried a LacZ construct that allows blue-white selection. The ROI and reporter plasmids were co-transformed into *Escherichia coli*. When the variable region ('N's) includes a PAM at either flank of the spacer, DNA nuclease activity introducing a double-strand break (DSBs) was expected. DSBs often lead to complete degradation of linearized plasmids in *E. coli*, which was thought to be the only possible outcome of DNA repair in *Escherichia coli*. However, molecular evidence for existence of alternative DNA repair mechanisms that lead to recircularization of linearized plasmids are accumulating. Most likely, these rearrangements occur by recombinations between short tracks of homologies as demonstrated by Wang et al. (Restriction-ligation-free (RLF) cloning: a high-throughput cloning method by in vivo homologous recombination of PCR products. 2015 Genet. Mol. Res., 14, 12306-12315). Alternatively, short homologies between a linear plasmid and a circular one can also lead to recombination resulting in chimeric plasmids. Some of these new variants deriving from targeted cleavage of the reporter construct would eliminate the reporter gene (LacZ), while retain the chloramphenicol resistance gene, which would produce rare chloramphenicol resistant white colonies in a 'sea' of blue colonies. Two negative controls were built as depicted in FIG. 7, where either the ROI (Control RGEN (−)) or the reporter region (Control Reporter (−)) were absent from their vector backbones. As shown in Table 6, four CRISPR enzymes (SEQ ID NOs: 2, 23, 32, and 35) showed significantly increased number of white colonies as compared to both negative controls lacking either the reporter region or the CRISPR enzyme region, suggesting that these CRISPR enzymes either eliminated or mutated the reporter plasmids.

Chloramphenicol (Cm) resistance gene, as compared with pTrc-I-SceI, which has the ColE-ori and Kanamycin resistance gene. pNuc appeared to express the I-SceI meganuclease at a low, non-toxic level in *E. coli*, in quantities sufficient to cut plasmids with an I-SceI restriction site. pNuc-I-SceI has unique NdeI and NotI sites that allow the easy replacement of the I-SceI coding region with other genes or operons. Cutting the plasmid with BamHI and NotI allows for cloning 1-9 kb genomic regions containing multiple ORFs, CRISPR loci or other sequences, where protein expression from ORFs will be originating from the native promoters, etc. A plasmid similar to pNUC (with a P-T7 promoter) was used by Kleinstiver to co-express Cas9 and sgRNA from one plasmid.

The reporter plasmid, pCut-I-SceI is very similar to p11-LacY-wtx1, with minor differences. pCut contains the highly toxic ccdB gene behind a well-regulated P-ara expression unit that expresses ccdB levels at such low levels in its uninduced state that cells containing pCut are healthy, Carbenicillin resistant cells. p11-LacY-wtx1 uses Ampicillin resistance gene in its vector. Addition of 0.2% arabinose to the growth medium, however, induces the expression of

TABLE 6

Six CRISPR enzymes tested for blue-white selection assay.

| PRT | ROI | Spacer-1 | Spacer-2 | # of white colonies among 750 blue colonies | | |
|---|---|---|---|---|---|---|
| (SEQ ID NO:) | (SEQ ID NO:) | (SEQ ID NO:) | (SEQ ID NO:) | Control_Reporter (−) | Control_RGEN (−) | Test |
| 2 | 222 | 223 | 224 | 0 | 0 | 15 |
| 3 | 225 | 226 | 227 | 0 | 5 | 6 |
| 23 | 228 | 229 | 230 | 0 | 2 | 39 |
| 32 | 231 | 232 | 233 | 0 | 1 | 39 |
| 34 | 234 | 235 | 236 | 6 | 0 | 6 |
| 35 | 237 | 238 | 239 | 0 | 1 | 27 |

Example 10: Validation of CRISPR Enzyme Activity Using a 2-Plasmid or 3-Plasmid Selection System A bacterial selection system was previously developed to study properties of homing endonucleases by linking DNA cleavage events with cell survival (Chen and Zhao, Nucleic Acids Research, 2005 33:e154). This system has been used to increase the in vivo cutting efficiency and specificity of a FokI nuclease domain (Guo et al., J. Mol Biol. 2010 400 (1):96-107). It has also been used to alter the PAM specificity of Cas9, an RNA-guided endonuclease (Kleinstiver, et al., Nature 2015 523:481-485). We further developed it to a highly sensitive selection system that couples CRISPR enzyme mediated DNA cleavage with the survival of host cells. Three plasmids—pNuc-I-SceI, pCut-I-SceI, and pGuide were built to enable either a 2-plasmid (pNuc and pCut) selection system, or a more flexible 3-plasmid selection system. The 2-plasmid system of Chen and Zhao consists of a 'reporter plasmid' (p11-LacY-wtx1), and an inducible protein expression vector (pTrc-I-SceI). The protein expression vector we have, pNuc-I-SeeI, is comparable to that used by Chen and Zhao with a few modifications. pNuc-I-SceI uses a strong P-tac promoter, similar but not identical to the P-trc promoter in pTrc-I-SceI. As a possible improvement, the lad gene (lac repressor) is present in the pNuc-I-SceI backbone, such that the plasmid can work well in non-lacI$^q$ hosts. pNuc-I-SceI is derived from the pACYC-Duet1 plasmid (Novagen), and has the P15a-ori and ccdB to levels that cause a 3-4 log-kill of cells bearing the plasmid. pCut-I-SceI also contains a 'cut site' immediately downstream of the ccdB gene. In pCut-I-SceI, the 'cut site' is a ~50 bp sequence containing the 18 bp recognition sequence of the I-SceI meganuclease. The region flanking the cut site contains unique restriction sites that allow the sequence to be replaced by other desired sequences that we would like to use as cut sites. The cut site in pCut-I-SceI can be a library of sequences, containing degenerate nucleotides (i.e. N=A or C or G or T).

The reason why the expression of an endonuclease that cuts pCut in its 'cut site' relieves the sensitivity to growth on arabinose is described by Chen and Zhao and others to be due to the rapid in vivo degradation of pCut and the loss of the arabinose-inducible ccdB gene. The system as such can be fine tuned for selecting recognition sequence variants of endonucleases, 'kinetic variants' (Guo et al., J. Mol Biol. 2010 400(1):96-107), or studying the in vivo temperature optimum for DNA cleavage.

When competent BW25141 cells containing pCut-I-SceI are made (a special host strain, described by Chen and Zhao) and transformed with pNuc-I-SceI, and side-by-side with (empty) pACYC-Duet1, and allowed to recover for approx. 2.5 hrs, without antibiotics, with or without the addition of IPTG (to further induce I-SceI expression from the P-tac promoter), aliquots of the cells can be plated on LB+25 ug/ml Chloramphenicol (Cm) agar plates (to determine transformation efficiency of the pNuc construct), alongside LB+25 ug/ml Cm+0.2% arabinose plates. Depending on dilutions and competency of the cells, cells transformed with (empty) pACYC-Duet1 yield 0-1 colony-forming units (cfus) on LB+25 ug/ml Cm+0.2% arabinose plates as compared to >1000 cfus on LB+25 ug/ml Cm plates. In contrast, cells transformed with pNuc-I-SceI yield 30 to >100 cfu's on LB+Cm+arabinose plates as compared to >500 cfu's on LB+Cm plates. A significant cfu count on '+arabinose' plates is the selection criterion chosen by Chen and Zhao for an active meganuclease.

Plasmids similar to pNuc have been used by others to co-express CRISPR enzymes along with their guide RNA(s) or a CRISPR locus (Zetsche et al. Cell, 2015 163:759-771). We reasoned that using a separate third plasmid, pGuide, to co-express guide RNAs will increase the flexibility of the selection system. To this end, the pCDF-Duet1 backbone (Novagen) containing the CDF-ori and Spectinomycin-r genes was chosen and a synthetic DNA J23119 (a synthetic constitutive E. coli promoter used by Zetsche, et al.) was inserted in the ~2.2 kB pCDF backbone to create pGuide plasmid. The guide RNA associated with a CRISPR enzyme of interest, for example NCC1, can be inserted in the pCDF backbone to create the pGuide-NCC1 plasmid.

Figure 8:
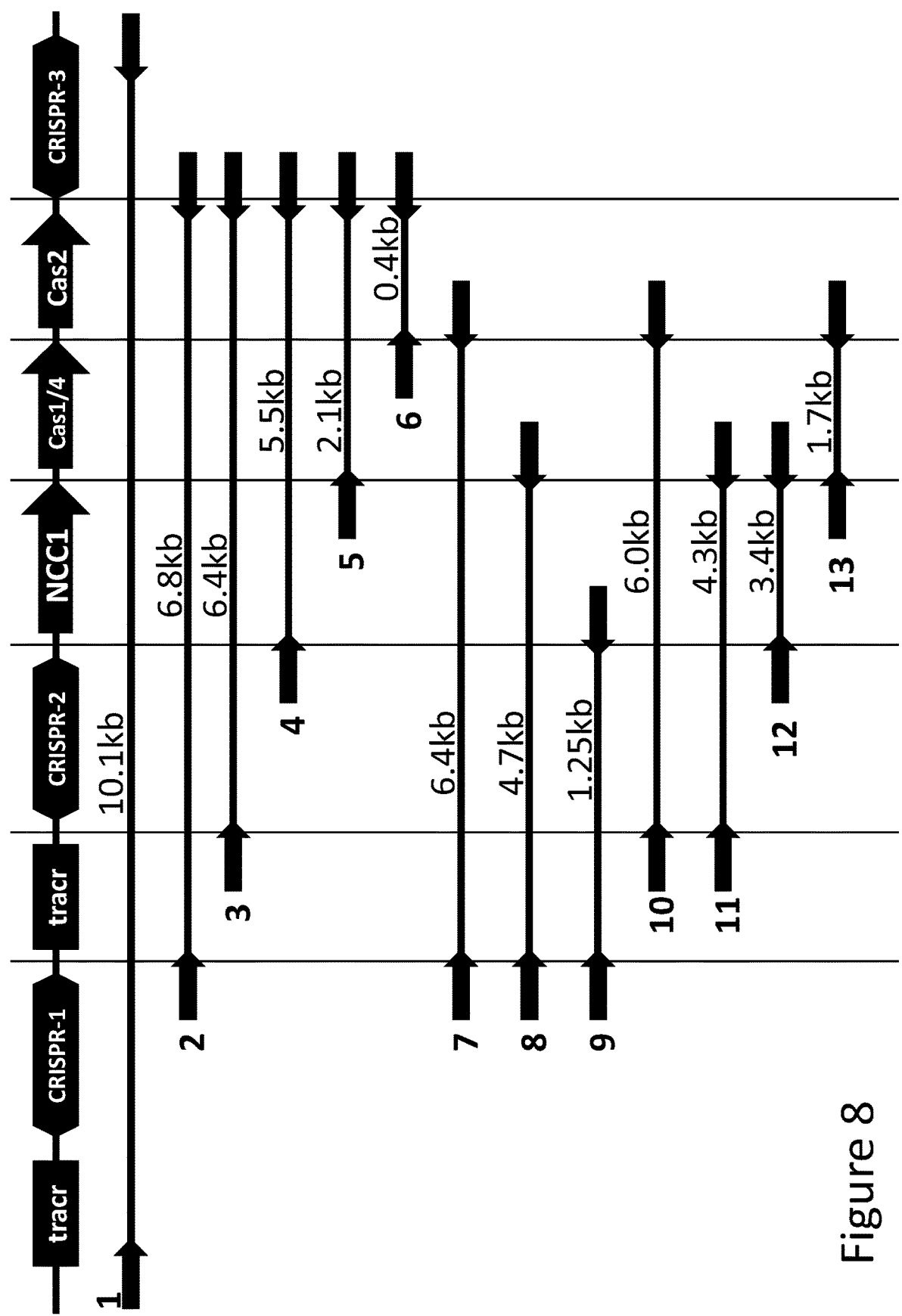
FIG. 8. Diagram of the constructs designed for the 2-plasmid and 3-plasmid assays to validate the RNA-guided endonuclease activity for NCC1 as described in Example 10. The diagram demarks 13 separate fragments of the NCC1 genomic region cloned into one of the plasmids for testing. For example, vector 1 contains the full 10.1 kb fragment of the NCC1 genomic region. Vector 2 contains a 6.8 kb fragment of the NCC1 genomic region including one of the tracrRNA, the CRISPR-2 locus, the NCC1 gene, the Cas1/Cas4 gene, and the Cas2 gene. Vector 3 contains a 6.4 kb fragment of the NCC1 genomic region including the CRISPR-2 locus, the NCC1 gene, the Cas1/Cas4 gene, and the Cas2 gene. Vector 4 contains a 5.5 kb fragment of the NCC1 genomic region including the NCC1 gene, the Cas1/Cas4 gene, and the Cas2 gene (NCC1 operon). Vector 5 contains a 2.1 kb fragment of the NCC1 genomic region including the Cas1/Cas4 gene, and the Cas2 gene. Vector 6 contains a 0.4 kb fragment of the NCC1 genomic region including only the Cas2 gene. Vector 7 contains a 6.4 kb fragment of the NCC1 genomic region including one of the tracrRNA, the CRISPR-2 locus, the NCC1 gene, and the Cas1/Cas4 gene. Vector 8 contains a 4.7 kb fragment of the NCC1 genomic region including one of the tracrRNA, the CRISPR-2 locus, and the NCC1 gene. Vector 9 contains a 1.25 kb fragment of the NCC1 genomic region including one of the tracrRNA, and the CRISPR-2 locus. Vector 10 contains a 6.0 kb fragment of the NCC1 genomic region including the CRISPR-2 locus, the NCC1 gene, and the Cas1/Cas4 gene. Vector 11 contains a 4.3 kb fragment of the NCC1 genomic region including the CRISPR-2 locus, and the NCC1 gene. Vector 12 contains a 3.4 kb fragment of the NCC1 genomic region including only the NCC1 gene. Vector 13 contains a 1.7 kb fragment of the NCC1 genomic region including only the Cas1/Cas4 gene.

The established 2-plasmid and 3-plasmid systems are used to determine RNA-guided endonuclease activities for the CRISPR enzymes represented by SEQ ID NOs: 1-36, 73 and 75-87. Using NCC1 (SEQ ID NO: 73) as an example, 13 constructs are designed and created for various genomic regions (SEQ ID NOs: 240-252) listed in FIG. 8 and among them, constructs 1-8 and 10-13 are cloned into the pNuc-I-SceI plasmid replacing the I-SceI component to create the pNuc-NCC1 plasmids. Construct-9 containing a tracrRNA and a CRISPR array is cloned into the pGuide plasmid. A NCC1 'cut site' (two spacers SEQ ID NOs: 253, 254 flanked by 8 variable nucleotides at both ends) is cloned into the pCut-I-SceI plasmid replacing the I-SceI cut site to create the pCut-NCC1 plasmid. A pCut-control plasmid is generated by incorporating a non-NCC1 'cut site' (e.g. Cas9 cut site) into the pCut-I-SceI plasmid.

The pNuc-NCC1 plasmids are tested with the pCut-NCC1 plasmid in the above described 2 plasmid assay to determine the minimal genomic fragment required for the CRISPR enzyme activity. The pNUC-NCC1 plasmids for constructs 4 and 12 are further tested with the pCut-NCC1 plasmid and the pGuide plasmid (comprising construct 9) to determine if the tracrRNA and CRISPR locus are required for CRISPR enzyme activity. The pCut-control plasmid is used to demonstrate specificity of the RNA-guided cleavage. Positive constructs are re-tested at 37° C., 30° C., and 25° C. to determine the optimal cleavage temperature.

Example 11: Programming the CRISPR Enzyme System for Genome Editing in Plants

The RGENs represented by SEQ ID NOs: 1-73 and 75-87 are tested and determined if they can be programmed for cleaving genomic DNA in plants. To demonstrate this activity, vectors are created to express the RGENS and the associated single guide RNAs (tracrRNA:crRNA fusions shown in Tables 3 and 5). For example, vectors are created to express NCC1 (SEQ ID NO: 73) and its sgRNA (SEQ ID NO: 197). The open reading frames of the RGENs were codon-optimized for corn and soy and listed in Table 7. Maize Ubiquitin2 promoter can be used to drive the expression of RGENs in plants. A nuclear localization signal (e.g. monopartite SV40) is added to the N terminus of a RGEN and a bipartite nucleoplasmin nuclear localization signal (BiNLS) to the C terminus to facilitate nuclear localization. To validate the effectiveness of nuclear localization signal used, maize protoplasts are transformed with a RGEN-GFP fusion protein construct and nuclear localized fluorescence is observed. The maize U6 snRNA promoter can be used for the generation of sgRNA in maize (J. Zhu et al. Journal of Genetics and Genomics 43 (2016) 25-36). The PAM sequences are identified for RGENs as described in Example 7, and the protospacer sequences recognized by RGENs can be used to identify sgRNA-specific target sites within maize nuclear protein coding genes with minimal off-target cuts, using the approach described by J. Zhu et al. Targets located in the first two exons are good candidates for the purpose of targeted gene disruption in maize, since mutations occurred at the beginning of the coding sequence are more likely to disrupt the function of the proteins.

TABLE 7

The codon-optimized open reading frames for RGENs for corn and soy.

| SEQ ID NO: (PRT) | SEQ ID NO: (DNA) | Organism | Corn codon-optimized (SEQ ID NO: ) | Soy codon-optimized (SEQ ID NO: ) |
|---|---|---|---|---|
| 1 | 37 | Lysinibacillus sp. multi | 300-304 | 550-554 |
| 2 | 38 | Bacillus sp. multi | 305-309 | 555-559 |
| 3 | 39 | Bacillus sp. multi | 310-314 | 560-564 |
| 4 | 40 | Bacillus sp. multi | 315-319 | 565-569 |
| 5 | 41 | Bacillus sp. multi | 320-324 | 570-574 |
| 6 | 42 | Bacillus sp. multi | 325-329 | 575-579 |
| 7 | 43 | Bacillus sp. multi | 330-334 | 580-584 |
| 8 | 44 | Bacillus sp. multi | 335-339 | 585-589 |
| 9 | 45 | Bacillus sp. multi | 340-344 | 590-594 |
| 10 | 46 | Bacillus sp. multi | 345-349 | 595-599 |
| 11 | 47 | Bacillus sp. multi | 350-354 | 600-604 |
| 12 | 48 | Bacillus sp. multi | 355-359 | 605-609 |
| 13 | 49 | Bacillus sp. multi | 360-364 | 610-614 |
| 14 | 50 | Bacillus sp. multi | 365-369 | 615-619 |
| 15 | 51 | Bacillus sp. multi | 370-374 | 620-624 |
| 16 | 52 | Bacillus sp. multi | 375-379 | 625-629 |
| 17 | 53 | Brevibacillus laterosporus | 380-384 | 630-634 |
| 18 | 54 | Bacillus thuringiensis | 385-389 | 635-639 |
| 19 | 55 | Brevibacillus laterosporus | 390-394 | 640-644 |

TABLE 7-continued

The codon-optimized open reading frames for RGENs for corn and soy.

| SEQ ID NO: (PRT) | SEQ ID NO: (DNA) | Organism | Corn codon-optimized (SEQ ID NO: ) | Soy codon-optimized (SEQ ID NO: ) |
|---|---|---|---|---|
| 20 | 56 | Brevibacillus laterosporus | 395-399 | 645-649 |
| 21 | 57 | Enterococcus faecalis | 400-404 | 650-654 |
| 22 | 58 | Brevibacillus brevis | 405-409 | 655-659 |
| 23 | 59 | Brevibacillus laterosporus | 410-414 | 660-664 |
| 24 | 60 | Bacillus sp. multi | 415-419 | 665-669 |
| 25 | 61 | Bacillus sp. multi | 420-424 | 670-674 |
| 26 | 62 | Brevibacillus laterosporus | 425-429 | 675-679 |
| 27 | 63 | Bacillus thuringiensis | 430-434 | 680-684 |
| 28 | 64 | Enterococcus faecalis | 435-439 | 685-689 |
| 29 | 65 | Sphingobium sp. novel | 440-444 | 690-694 |
| 30 | 66 | Undibacterium pigrum | 445-449 | 695-699 |
| 31 | 67 | Bacillus sp. multi | 450-454 | 700-704 |
| 32 | 68 | Chryseobacterium sp. novel | 455-459 | 705-709 |
| 33 | 69 | Novosphingobium rosa | 460-464 | 710-714 |
| 34 | 70 | Chryseobacterium sp. novel | 465-469 | 715-719 |
| 35 | 71 | Labrys methylaminiphilus | 470-474 | 720-724 |
| 36 | 72 | Brevibacillus brevis | 475-479 | 725-729 |
| 73 | 74 | Brevibacillus parabrevis | 480-484 | 730-734 |
| 75 | 88 | Desulfovibrio inopinatus | 485-489 | 735-739 |
| 76 | 89 | Alicyclobacillus contaminans | 490-494 | 740-744 |
| 77 | 90 | Desulfatirhabdium butyrativorans | 495-499 | 745-749 |
| 78 | 91 | Tuberibacillus calidus | 500-504 | 750-754 |
| 79 | 92 | Alicyclobacillus acidoterrestris | 505-509 | 755-759 |
| 80 | 93 | Brevibacillus sp. Multi | 510-514 | 760-764 |
| 81 | 94 | Brevibacillus sp. multi | 515-519 | 765-769 |
| 82 | 95 | Methylobacterium nodulans | 520-524 | 770-774 |
| 83 | 96 | Alicyclobacillus contaminans | 525-529 | 775-779 |
| 84 | 97 | Alicyclobacillus herbarius | 530-534 | 780-784 |
| 85 | 98 | Brevibacillus parabrevis | 535-539 | 785-789 |
| 86 | 99 | Brevibacillus parabrevis | 540-544 | 790-794 |
| 87 | 100 | Brevibacillus fluminis | 545-549 | 795-799 |

To test the activity of customized CRISPR enzyme system for maize endogenous gene editing, a protoplast transient assay is conducted to detect the function of the engineered CRISPR enzyme system. To increase the transformation efficiency, binary plasmids with both sgRNA and CRISPR enzyme expression cassette are generated and then transformed into maize protoplasts. Genomic DNA is extracted from transformed protoplasts cultured for 24 h and amplicons encompassing target sites are prepared for Illumina deep sequencing. The targeted mutations can be observed as deletions, insertions, and deletions accompanied by insertions.

To test the mutation efficiency of a CRISPR enzyme system in stable expression lines, a target site verified in the maize transient assay is chosen. Constructs encoding sgRNA capable of hybridizing to the target site, and the CRISPR enzyme are then transformed into maize immature embryos via *Agrobacterium tumefaciens*. TO transgenic lines are analyzed and the CRISPR enzyme containing lines are identified based on immunoblot analysis. SURVEYOR assays can be used to determine whether mutations are introduced in the target site (J. Zhu et al. Journal of Genetics and Genomics 43 (2016) 25-36). For detailed analysis of mutation efficiency and mutation type introduced by CRISPR enzymes, the PCR amplicons encompassing the target site can be deep-sequenced for the CRISPR enzyme positive TO generation plants.

SEQUENCE LISTING

The patent contains a lengthy sequence listing. A copy of the sequence listing is available in electronic form from the USPTO web site (https://seqdata.uspto.gov/?pageRequest=docDetail&DocID=US11692182B2). An electronic copy of the sequence listing will also be available from the USPTO upon request and payment of the fee set forth in 37 CFR 1.19(b)(3).

What is claimed is:

1. A non-naturally occurring system for sequence-specific modification of a target nucleic acid sequence, the system comprising: (a) one or more guide RNAs or a DNA molecule encoding the one or more guide RNAs; and (b) a CRISPR enzyme having the amino acid sequence of SEQ ID NO:73 or polynucleotide encoding the CRISPR enzyme, wherein the one or more guide RNAs and the CRISPR enzyme do not naturally occur together.

2. The system of claim 1, wherein the polynucleotide encoding the CRISPR enzyme comprises a nucleotide sequence having at least 90% identity to SEQ ID NO: 74.

3. The system of claim 1, wherein the target nucleic acid sequence comprises a coding nucleic acid sequence.

4. The system of claim 1, wherein the target nucleic acid sequence comprises an endogenous gene.

5. The system of claim 1, wherein the system comprises a divalent cation.

6. The system of claim 1, wherein the guide RNA or a DNA molecule encoding a guide RNA and the polynucleotide encoding the CRISPR enzyme are provided on a single nucleic acid molecule.

7. The system of claim 1, wherein the guide RNA is encoded in an *Agrobacterium* vector.

8. The system of claim 1, wherein the system further comprises a donor polynucleotide.

9. The system of claim 8, wherein the donor polynucleotide comprises a coding nucleic acid sequence.

10. The system of claim 8, wherein the donor polynucleotide comprises a promoter.

11. The system of claim 1, wherein the CRISPR enzyme comprises one or more nuclear localization signals.

12. The system of claim 1, wherein the target sequence is within a cell.

13. The system of claim 1, wherein the cell is a eukaryotic cell.

14. The system of claim 13, wherein the eukaryotic cell is a plant cell.

15. A method for sequence specific modification of a target nucleic acid sequence in a cell, comprising providing the system of claim 1 to a cell that comprises the target nucleic acid sequence.

16. The method of claim 15, wherein the cell is a plant cell.

17. A recombinant nucleic acid, comprising a heterologous promoter operably linked to a polynucleotide encoding a CRISPR enzyme having the amino acid sequence of SEQ ID NO: 73.

18. The recombinant nucleic acid of claim 17, wherein the polynucleotide encoding the CRISPR enzyme comprises a nucleotide sequence having at least 90% identity to SEQ ID NO: 74.

19. The recombinant nucleic acid of claim 17, further comprising at least one polynucleotide encoding a guide RNA, wherein the guide RNA forms a complex with the CRISPR enzyme.

20. The recombinant nucleic acid of claim 19, wherein the at least one polynucleotide encoding a guide RNA is operably linked to a second promoter.

21. The recombinant nucleic acid of claim 17, further comprising at least one polynucleotide encoding a donor polynucleotide.

22. The recombinant nucleic acid of claim 17, wherein the polynucleotide encoding the CRISPR enzyme further encodes at least one nuclear localization signal (NLS).

23. A vector comprising the recombinant nucleic acid of claim 17.

24. A eukaryotic cell comprising the recombinant nucleic acid of claim 17.

25. The method of claim 15, wherein:
(a) the guide RNA is provided by expressing in the cell a recombinant DNA molecule encoding the guide RNA;
(b) the CRISPR enzyme is provided by expressing in the cell a recombinant DNA molecule encoding the CRISPR enzyme; or
(c) both (a) and (b).

26. The method of claim 15, wherein:
(a) the guide RNA is provided by contacting the cell with a composition comprising the guide RNA or a recombinant DNA molecule encoding the guide RNA;
(b) the CRISPR enzyme is provided by contacting the cell with a composition comprising the CRISPR enzyme or a recombinant DNA molecule encoding the CRISPR enzyme; or
(c) the CRISPR enzyme is complexed with the guide RNA and is provided to the cell as a particle.

27. The method of claim 15, wherein the CRISPR enzyme comprises one or more nuclear localization signals.

28. The method of claim 15, wherein the recombinant DNA molecule encoding the CRISPR enzyme comprises a nucleotide sequence having at least 90% identity to SEQ ID NO: 74.

29. The method of claim 15, wherein the target nucleic acid sequence comprises a coding nucleic acid sequence.

30. The method of claim 15, wherein the target nucleic acid sequence comprises (a) an endogenous nuclear gene of the cell or of an organelle in the cell; or (b) an endogenous organellar gene of the cell.

31. The method of claim 15, further comprising providing a donor polynucleotide to the cell.

32. The method of claim 31, wherein the donor polynucleotide comprises a coding nucleic acid sequence.

* * * * *